US007858742B2

(12) United States Patent
Shipp et al.

(10) Patent No.: US 7,858,742 B2
(45) Date of Patent: Dec. 28, 2010

(54) LYMPHOMA ASSOCIATED MOLECULES AND USES THEREFOR

(75) Inventors: Margaret Shipp, Wellesley, MA (US); Ricardo Aguiar, Chestnut Hill, MA (US); Yoshi Yakushijin, Matsuyama (JP)

(73) Assignee: Dana-Farber Cancer Institute, Boston, MA (US)

( * ) Notice: Subject to any disclaimer, the term of this patent is extended or adjusted under 35 U.S.C. 154(b) by 468 days.

(21) Appl. No.: 10/918,877

(22) Filed: Aug. 16, 2004

(65) Prior Publication Data

US 2005/0014186 A1 Jan. 20, 2005

Related U.S. Application Data

(63) Continuation of application No. 09/830,762, filed as application No. PCT/US99/25439 on Oct. 29, 1999, now Pat. No. 6,870,040.

(60) Provisional application No. 60/106,383, filed on Oct. 29, 1998, provisional application No. 60/106,448, filed on Oct. 30, 1998.

(51) Int. Cl.
*C07K 14/00* (2006.01)
*C07H 21/00* (2006.01)
*C12P 21/00* (2006.01)
*C12N 15/63* (2006.01)

(52) U.S. Cl. ........................ 530/350; 536/23.1; 435/7.1; 514/44

(58) Field of Classification Search ........................ None
See application file for complete search history.

(56) References Cited

U.S. PATENT DOCUMENTS

| 7,041,814 | B1 * | 5/2006 | Weinstock et al. | 536/24.1 |
| 7,112,420 | B2 * | 9/2006 | Shipp et al. | 435/69.6 |
| 7,393,663 | B2 * | 7/2008 | Edwards et al. | 435/69.8 |

OTHER PUBLICATIONS

Aguiar et al. The Journal of Biological Chemistry, 2005, vol. 280, p. 33756-33765.*
Aguiar et al., "TEL-AML1 fusion in acute lymphoblastic leukaemia of adults," British Journal of Haematology, 95:673-677 (1996).
Aguiar et al., "Molecular characterization of a tissue-specific protein tyrosine phosphatase (PTP) and putative tumor suppressor which is down-regulated in high risk diffuse large B-cell lymphomas (DLBCLs)," Blood 90 (Suppl. 1):491a, Abstract 2185 (1997).
Aguiar et al., "The commonly deleted region at 9p21-22 in lymphoblastic leukemias spans at least 400 kb and includes p16 but not p15 or the IFN gene cluster," Leukemia, 11:233-238 (1997).
Aguiar et al., "PTPROt: An Alternatively Spliced and Developmentally Regulated B-Lymphoid Phosphatase that Promotes G0/G1 Arrest," Blood 94(7):2403-2413 (Oct. 1, 1999).
Bowie et al., "Deciphering the message in protein sequences: tolerance to amino acid substitutions," Science, 247:1306-1310(1990).
Bretscher et al., "EGF induces recycling membrane to form ruffles," Current Biology, 8:721-724 (1998).
Burgess et al., "Possible Dissociation of the heparin-binding and mitogenic activities of heparin-binding (acidic fibroblast) growth factor-1 from its receptor-binding activities by site-directed mutagenesis of a single lysine residue," Journal of Cell Biol., 111:2129-2138 (1990).
Cabanillas et al., "Frequent Nonrandom Chromosome Abnormalities in 27 Patients with Untreated Large Cell Lymphoma and Immunoblastic Lymphoma," Cancer Research, 48:5557-5564 (Oct. 1, 1988).
Lazar et al., "Transforming growth factor alpha: mutation of aspartic acid 47 and leucine 48 results in different biological activities," Molecular and Cellular Biology, 8(3):1247-1252 (1988).
Liang et al., "Differential Display of Eurkaryotic Messenger RNA by Means of the Polymerase Chain Reaction," Science, 257:967-971 (Aug. 14, 1992).
Mitelman et al., "A breakpoint map of recurrent chromosomal rearrangements in human neoplasia," Nature Genetics, 15:417-474 (Apr. 1997).
Monni et al., "Gain of 3q and Deletion of llq22 Are Frequent Aberrations in Mantle Cell Lymphoma," Genes, Chromosomes & Cancer, 21:298-307 (1998).
Pehrson et al., "Evolutionary conservation of histone macroH2A subtyes and domains," Nucleic Acids Research, 26(12):2837-2842 (1998).
Schouten et al., "Chromosomal Abnormalities in Untreated Patients with Non-Hodgkin's Lymphoma: Associations With Histology, Clinical Characteristics, and Treatment Outcome," Blood, 75(9):1841-1847 (1990).
Shipp et al., "A Predictive Model for Aggressive Non-Hodgkin's Lymphoma," New England Journal of Medicine, 329(14):987-994 (1993).
Warrick et al., "Myosin Structure and Function in Cell Motility," Ann. Rev. Cell Biol., 3:379-421 (1987).
Yakushijin et al., "A Directly Spliced Exon 10-Containing CD44 Variant Promotes the Metastasis and Homotypic Aggregation of Aggressive Non-Hodgkin's Lymphoma," Blood, 91(11):4282-4291 (Jun. 1, 1998).
Adams et al., "Rapid cDNA sequencing (expressed sequence tags) from a directionally cloned human infant brain cDNA library," Nature Genetics, 4(4):373-380 (1993) Abstract.

(Continued)

*Primary Examiner*—Zachariah Lucas
*Assistant Examiner*—Agnieszka Boesen
(74) *Attorney, Agent, or Firm*—Foley Hoag, LLP

(57) ABSTRACT

The invention provides isolated nucleic acids molecules, designated BAL nucleic acid molecules, which are differentially expressed in non-Hodgkin's lymphoma. The invention also provides antisense nucleic acid molecules, recombinant expression vectors containing BAL nucleic acid molecules, host cells into which the expression vectors have been introduced, and nonhuman transgenic animals in which a BAL gene has been introduced or disrupted. The invention still further provides isolated BAL proteins, fusion proteins, antigenic peptides and anti-BAL antibodies. Diagnostic methods using compositions of the invention are also provided.

7 Claims, 23 Drawing Sheets

OTHER PUBLICATIONS

Bonaldo et al., "Normalization and subtraction: two approaches to facilitate gene discovery," Genome Research, 6(9):791-806 (1996) Abstract.

Mercer D.W., "Immunoassays for the detection of tumor associated antigens," In Manual of clinical laboratory immunology, Edited by Rose et al., Washington, D.C. American Society for Microbioloty, 4th Ed., pp. 791-795.

Pharmacia, Overview of molecular biology products. Pharmacia Biotech., pp. 107, 110-117, 139, 163-165 (1996).

Zambrowicz et al., Disruption and sequence identification of 2000 genes in mouse embryonic stem cells, Nature, 392:608-611 (Apr. 9, 1998).

Database EMBL Apr. 25, 1998 "AF046630 Mus musculus 129Sv/Ev Mus musculus genomic clone OST8563, DNA sequence," XP002316474, retrieved from EBI accession No. EM_GSS:AFO46630, Database accession No. AF046630.

Database EMBL Dec. 14, 1996 "mr05c07.r1 Soares mouse 3NbMS Mus musculus cDNA clone Image:596556 5', mRNA sequence," XP002316475, retrieved from EBI accession No. EM_EST:AA146363, Database accession No. AA146363.

Database EMBL Oct. 1, 1998, "ud16c02.r1 Soares 2NbMT Mus musculus cDNA clone Image:1446050 5', mRNA sequence," XP002316476, retrieved from EBI accession No. EM_EST:AI157103, Database accession No. AI157103.

Database EMBL Sep. 22, 1998 "qc34a12.x1 Soares_pregnant_uterus_NbHPU Homo sapiens cDNA clone Image:1711486 3', mRNA sequence," XP002316477, retrieved from EBI accession No. EM_EST:AI129360, Database accession No. AI129360.

Database EMBL Dec. 15, 1996 "z125b01.r1 Soares_pregnant_uterus_NbHPU Homo sapiens cDNA clone Image:502921 5', mRNA sequence," XP002316478, retrieved from EBI accession No. EM_EST:AA151346, Database accession No. AA151346.

Yakushijin et al., "Molecular characterization of a novel gene, bal, which regulates the proliferation of aggressive B-cell lymphomas," Blood, 90(10) Suppl. 1, Part 1, p. 177A, XP008042576.

Hillier et al., "Generation and Analysis of 280,000 Human Expressed Sequence Tags," Genome Res. 6(9):807-828 (1996).

* cited by examiner

BAL human cDNA

5'UTR:
GGGCTTCGTGTTCCTGGGTGCTGACCGTGCACTCCCCGCCGCCCGAGGACTTAGAGCTCTGGAAGT
AGCTCTCCAGCTTCCTTCGTACTCGGGGGCCGGACTTGTACACCCGCACGAGGAGCGGGGACGGC
GGGCGCAGAAGTGGGCCACCATATCTGGAAACTACAGTCTATGCTTTGAAGCGCAAAAGGGAATA
AACATTTAAAGACTCCCCCGGGGACCTGGAGG

Coding: alternatively spliced sequence in bold characters

ATGGACTTTTCCATGGTGGCCGGAGCAGCAGCTTACAATGAAAAATCAG**GTAGGATTACCTCGCT
CTCACTCTTGTTTCAGAAAGTCTTTGCTCAGATCTTTCCTCAGTGGAGAAAGGGGAATACAG
AAGAATGTCTCCCCTACAAGTGCTCAG**AGACTGGTGCTCTTGGAGAAAACTATAGTTGGCAAAT
TCCCATTAACCACAATGACTTCAAAATTTTAAAAAATAATGAGCGTCAGCTGTGTGAAGTCCTCCA
GAATAAGTTTGGCTGTATCTCTACCCTGGTCTCTCCAGTTCAGGAAGGCAACAGCAAATCTCTGCA
AGTGTTCAGAAAAATGCTGACTCCTAGGATAGAGTTATCAGTCTGGAAAGATGACCTCACCACAC
ATGCTGTTGATGCTGTGGTGAATGCAGCCAATGAAGATCTTCTGCATGGGGGAGGCCTGGCCCTGG
CCCTGGTAAAAGCTGGTGGATTTGAAATCCAAGAAGAGAGCAAACAGTTTGTTGCCAGATATGGT
AAAGTGTCAGCTGGTGAGATAGCTGTCACGGGAGCAGGGAGGCTTCCCTGCAAACAGATCATCCA
TGCTGTTGGGCCTCGGTGGATGGAATGGGATAAACAGGGATGTACTGGAAAGCTGCAGAGGGCCA
TTGTAAGTATTCTGAATTATGTCATCTATAAAAATACTCACATTAAGACAGTAGCAATTCCAGCCT
TGAGCTCTGGGATTTTTCAGTTCCCTCTGAATTTGTGTACAAAGACTATTGTAGAGACTATCCGGGT
TAGTTTGCAAGGGAAGCCAATGATGAGTAATTTGAAAGAAATTCACCTGGTGAGCAATGAGGACC
CTACTGTTGCTGCCTTTAAAGCTGCTTCAGAATTCATCCTAGGGAAGAGTGAGCTGGGACAAGAAA
CCACCCCTTCTTTCAATGCAATGGTCGTGAACAACCTGACCCTCCAGATTGTCCAGGGCCACATTG
AATGGCAGACGGCAGATGTAATTGTTAATTCTGTAAACCCACATGATATTACAGTTGGACCTGTGG
CAAAGTCAATTCTACAACAAGCAGGAGTTGAAATGAAATCGGAATTTCTTGCCACAAAGGCTAAA
CAGTTTCAACGGTCCCAGTTGGTACTGGTCACAAAAGGATTTAACTTGTTCTGTAAATATATATAC
CATGTACTGTGGCATTCAGAATTTCCTAAACCTCAGATATTAAAACATGCAATGAAGGAGTGTTTG
GAAAAATGCATTGAGCAAAATATAACTTCCATTTCCTTTCCTGCCCTTGGGACTGGAAACATGGAA
ATAAAGAAGGAAACAGCAGCAGAGATTTTGTTTGATGAAGTTTTAACATTTGCCAAAGACCATGT
AAAACACCAGTTAACTGTAAAATTTGTGATCTTTCCAACAGATTTGGAGATATATAAGGCTTTCAG
TTCTGAAATGGCAAAGAGGTCCAAGATGCTGAGTTTGAACAATTACAGTGTCCCCCAGTCAACCA
GAGAGGAGAAAAGAGAAAATGGGCTTGAAGCTAGATCTCCTGCCATCAATCTGATGGGATTCAAC
GTGGAAGAGATGTAGTGAGGCCCACGCATGGATCCAAAGAATCCTGAGTCTCCAGAACCACCA
TCATTGAGAATAATCATATTCTGTACCTTGGGAGAAAGGAACATGACATTTTGTCTCAGCTTCAGA
AAACTTCAAGTGTCTCCATCACAGAAATTATCAGCCCAGGAAGGACAGAGTTAGAGATTGAAGGA
GCCCGGGCTGACCTCATTGAGGTGGTTATGAACATTGAAGATATGCTTTGTAAAGTACAGGAGGA
AATGGCAAGGAAAAGGAGCGAGGCCTTTGGCGCTCGTTAGGACAGTGGACTATTCAGCAACAAA
AAACCCAAGACGAAATGAAAGAAAATATCATATTTCTGAAATGTCCTGTGCCTCCAACTCAAGAG
CTTCTAGATCAAAAGAAACAGTTTGAAAAATGTGGTTTGCAGGTTCTAAAGGTGGAGAAGATAGA
CAATGAGGTCCTTATGGCTGCCTTTCAAAGAAAGAAGAAAATGATGGAAGAAAAACTGCACAGGC
AACCTGTGAGCCATAGGCTGTTTCAGCAAGTCCCATACCAGTTCTGCAATGTGGTATGCAGAGTTG
GCTTTCAAAGAATGTACTCGACACCTTGCGATCCAAAATACGGAGCTGGCATATACTTCACCAAGA
ACCTCAAAAACCTGGCAGAGAAGGCCAAGAAAATCTCTGCTGCAGATAAGCTGATCTATGTGTTT
GAGGCTGAAGTACTCACAGGCTTCTTCTGCCAGGGACATCCGTTAAATATTGTTCCCCCACCACTG
AGTCCTGGAGCTATAGATGGTCATGACAGTGTGGTTGACAATGTCTCCAGCCCTGAAACCTTTGTT
ATTTTTAGTGGCATGCAGGCTATACCTCAGTATTTGTGGACATGCACCCAGGAATATGTACAGTCA
CAAGATTACTCATCAGGACCAATGAGACCCTTTGCACAGCATCCTTGGAGGGGATTCGCAAGTGG
CAGCCCTGTTGATTAA

Fig. 1

3' UTR
TCTCTACATCATTTTAACAGCTGGTATGGCCTTACCTTGGGTGAACTAACCAAATAATGACCATCG
ATGGCTCAAAGAGTGGCTTGAATATATCCCATGGGTTATCTGTATGGACTGACTGGGTTATTGAAA
GGACTAGCCACATACTAGCATCTTAGTGCCTTTATCTGTCTTTATGTCTTGGGGTTGGGGTAGGTAG
ATACCAAATGAAACACTTTCAGGACCTTCCTTCCTCTTGCAGTTGTTCTTTAATCTCCTTTACTAGA
GGAGATAAATATTTTGCATATAATGAAGAAATTTTTCTAGTATATAACGCAGGCCTTTTATTTTCTA
AAATGATGATAGTATAAAAATGTTAGGATAACAGAATGATTTTAGATTTTCCAGAGAATATTATAA
AGTGCTTTAGGTATGAAAATAAATCATCTTTGTCTGATTAAAAAAAAAAAA

BAL human protein: alternatively spliced (Bold characters)

MDFSMVAGAAAYNEKSGRITSLSLLFQKVFAQIFPQWRKGNTEECLPYKCSETGALGENYSW
QIPINHNDFKILKNNERQLCEVLQNKFGCISTLVSPVQEGNSKSLQVFRKMLTPRIELSVWKDDLTT
HAVDAVVNAANEDLLHGGGLALALVKAGGFEIQEESKQFVARYGKVSAGEIAVTGAGRLPCKQIIHAV
GPRWMEWDKQGCTGKLQRAIVSILNYVIYKNTHIKTVAIPALSSGIFQFPLNLCTKTIVETIRVSLQGKP
MMSNLKEIHLVSNEDPTVAAFKAASEFILGKSELGQETTPSFNAMVVNNLTLQIVQGHIEWQTADVIVN
SVNPHDITVGPVAKSILQQAGVEMKSEFLATKAKQFQRSQLVLVTKGFNLFCKYIYHVLWHSEFPKPQI
LKHAMKECLEKCIEQNITSISFPALGTGNMEIKKETAAEILFDEVLTFAKD
HVKHQLTVKFVIFPTDLEIYKAFSSEMAKRSKMLSLNNYSVPQSTREEKRENGLEARSPAINLMGFNVE
EMYEAHAWIQRILSLQNHHIIENNHILYLGRKEHDILSQLQKTSSVSITEIISPGRTELEIEGARADLIEVV
MNIEDMLCKVQEEMARKKERGLWRSLGQWTIQQQKTQDEMKENIIFLKCPVPPTQELLDQKKQFEKC
GLQVLKVEKIDNEVLMAAFQRKKKMMEEKLHRQPVSHRLFQQVPYQFCNVVCRVGFQRMYSTPCDP
KYGAGIYFTKNLKNLAEKAKKISAADKLIYVFEAEVLTGFFCQGHPLNIVPPPLSPGAIDGHDSVVDNVS
SPETFVIFSGMQAIPQYLWTCTQEYVQSQDYSSGPMRPFAQHPWRGFASGSPVD

Fig. 1 (continued)

BAL mouse cDNA:

5'UTR
AGGAACGGAAGTTTGGCGGGAACCCGGATTCCCAGGTTCAGGCCTCTCAAGGGTGGAGCGGAATA
GAGGGAAACAGGCCACCATCTCCTCGATCTACAGACTACACTTGGAAACACAAACAAATATAAAT
ATCTGAAGACCCACGTGGGACCTGAAGAATGGCCTATTAC

Coding region (shorter form only)
ATGGATACATGGGCGGCAGCTCCCGCCGAAAGACCAGCCAACAATTCTCTTGAAGAACATTATAG
ATGGCAAATTCCCATTAAACACAATGTCTTCGAATTTTAAAGAGCAATGAGAGTCAGCTATGTGA
AGTCCTCCAAAATAAGTTTGGATGCATCTCTACCCTGAGCTGTCCAACTCTAGCAGGGAGCAGCTC
TCCTGCTCAGAGAGTCTTCAGAAGGACCCTGATCCCTGGGATAGAGTTATCTGTCTGGAAGGATGA
CCTTACCAGACACGTTGTTGATGCTGTGGTGAACGCAGCCAATGAAAACCTTTTGCATGGAAGTGG
CCTGGCCGGAAGCTTGGTGAAAACTGGTGGCTTTGAAATCCAAGAAGAGAGCAAAAGAATCATTG
CCAACGTTGGTAAAATCTCAGTTGGTGGAATCGCTATCACCGGTGCGGGGAGACTTCCTTGCCATT
TGATTATCCATGCGGTTGGACCTCGGTGGACAGTTACGAACAGCCAGACAGCTATCGAATTACTGA
AATTTGCCATTAGGAACATTCTAGATTATGTCACCAAATATGATCTACGCATTAAGACAGTAGCAA
TTCCAGCCCTGAGCTCTGGAATTTTCCAGTTCCCTCTGGATTTGTGTACAAGCATAATTTTAGAAAC
TATCCGGCTTTATTTCCAAGACAAGCAAATGTTCGGTAATTTGAGAGAGATTCATCTGGTGAGCAA
TGAGGACCCCACTGTTGCGTCCTTTAAATCCGCCTCAGAAAGCATCCTAGGGAGGGACCTGAGCTC
TTGGGGGGGTCCAGAAACTGACCCTGCTTCCACCATGACTCTTCGCATCGGCCGGGGCCTGACTCT
CCAGATTGTCCAAGGCTGTATTGAAATGCAAACAACAGATGTAATTGGTAATTCTGGATACATGCA
GGATTTTAAATCAGGACGAGTGGCACAGTCGATTCTTAGACAAGCAGGGGTTGAAATGGAAAAGG
AACTTGACAAGGTTAACCTGTCCACAGATTATCAAGAGGTGTGGGTCACAAAAGGATTTAAATTGT
CCTGTCAGTATGTCTTCCATGTGGCATGGCATTCCCAAATCAACAAATACCAGATATTGAAAGATG
CAATGAAGTCCTGTCTAGAAAAATGCCTTAAACCAGATATAAATTCCATTTCCTTTCCTGCTCTCG
GGACAGGATTGATGGATTTGAAGAAGAGTACAGCAGCTCAGATAATGTTTGAGGAAGTTTTTGCA
TTTGCTAAAGAGCACAAGGAAAAAACGCTAACTGTAAAGATTGTGATCTTTCCAGTAGATGTGGA
GACGTACAAGATTTTTTATGCTGAAATGACAAAAAGGTCCAACGAGCTGAATCTCAGCGGTAATA
GTGGTGCTTTAGCCCTGCAGTGGTCCAGTGGGGAGCAAAGAAGAGGCGGCCTTGAAGCTGGATCT
CCTGCCATCAATCTCATGGGTGTAAAAGTGGGAGAGATGTGTGAGGCCCAGGAATGGATTGAAAG
GTTGCTGGTCTCCCTGGACCACCACATCATTGAGAATAATCATATTCTCTATCTTGGGAAAAAGA
GCACGACGTGCTGTCTGAGCTCCAGACCAGCACAAGAGTCTCCATTTCAGAGACTGTCAGTCCAA
GAACGGCCACTTTGGAGATTAAAGGTCCCCAGGCTGACCTCATTGACGCAGTTATGAGGATTGAAT
GTATGCTGTGTGACGTTCAGGAAGAAGTGGCAGGAAAAAGGGAGAAAAATCTTTGGAGCTTGTCA
GGACAGGGGACCAACCAGCAAGAAAAACTGGATAAAATGGAAGAATCGTACACATTTCAACGAT
ACCCAGCATCATTAACTCAGGAACTTCAGGACCGAAAGAAACAGTTTGAAAAGTGTGGCTTGTGG
GTTGTGCAGGTGGAGCAGATAGACAATAAGGTGCTGCTGGCTGCCTTCCAAGAGAAGAAGAAAAT
GATGGAAGAGAGGACGCCAAAGGGATCTGGGAGCCAAAGGTTGTTTCAGCAGGTCCCACATCAGT
TCTGCAATACGGTGTGCAGAGTCGGCTTCCACAGAATGTATTCGACATCCTATAACCCAGTTTATG
GAGCCGGCATATATTTCACCAAGAGCCTCAAAAATCTAGCAGACAAGGTCAAGAAAACCTCAAGC
ACAGACAAGCTAATCTATGTGTTTGAGGCAGAAGTACTCACAGGGTCCTTCTGTCAGGGTAATTCC
TCAAATATCATCCCTCCACCATTGAGTCCTGGGCCTTAGATGTCAATGACAGCGTAGTTGACAAT
GTTTCCAGCCCTGAAACCATTGTTGTTTTAATGGCATGCAGGCCATGCCCCTGTACTTGTGGACTT
GCACACAGGATAGGACATTCTCACAGCATCCGATGTGGTCACAGGACTACTCATCAGGACCAGGA
ATGGTCTCTTCGCTGCAGTCCTGGGAATGGGTCTTAAATGGCAGCTCTGTTTAG 3'UTR:
TGTCTACATCAGTTTAACAAGCAGAAGGGGTTGAGAGAACTGACAAAATGATAAATAACAGGTTA
CCTGTTCAGAATGATGGGGTCACTAAAGGCACCGACCACACACTAGCATCATAGTGCCTTTGTCTT
TACCTCTGGGCTTGACTGGGCAGATGCCAGCTAAAACTTCCTCACTGTCTT

Fig. 2

```
TTCTATTTGAtATCTTTCATCTCCTTTCCTATAGGTGACAGCAAGAATACTTTATATAGAACAAGGA
TATTTTTTTCAAGCCTGTTATTTTCTAAAATGATAGCACAAACTAGGACAACAGGATGATTTCAGG
TTTTCTATATAATTTATAAAGTGCTTTGGATATCCAAATAAATCACCTTTGTCTGAGT
```

BAL mouse protein (shorter form):

```
MDTWAAAPAERPANNSLEEHYRWQIPIKHNVFEILKSNESQLCEVLQNKFGCISTLSCPTLAGSSS
PAQRVFRRTLIPGIELSVWKDDLTRHVVDAVVNAANENLLHGSGLAGSLVKTGGFEIQEESKRIIA
NVGKISVGGIAITGAGRLPCHLIIHAVGPRWTVTNSQTAIELLKFAIRNILDYVTKYDLRIKTVAIPA
LSSGIFQFPLDLCTSIILETIRLYFQDKQMFGNLREIHLVSNEDPTVASFKSASESILGRDLSSWGGP
ETDPASTMTLRIGRGLTLQIVQGCIEMQTTDVIGNSGYMQDFKSGRVAQSILRQAGVEMEKELDK
VNLSTDYQEVWVTKGFKLSCQYVFHVAWHSQINKYQILKDAMKSCLEKCLKPDINSISFPALGT
GLMDLKKSTAAQIMFEEVFAFAKEHKEKTLTVKIVIFPVDVETYKIFYAEMTKRSNELNLSGNSG
ALALQWSSGEQRRGGLEAGSPAINLMGVKVGEMCEAQEWIERLLVSLDHHIIENNHILYLGKKE
HDVLSELQTSTRVSISETVSPRTATLEIKGPQADLIDAVMRIECMLCDVQEEVAGKREKNLWSLS
GQGTNQQEKLDKMEESYTFQRYPASLTQELQDRKKQFEKCGLWVVQVEQIDNKVLLAAFQE K
KKMMEERTPKGSGSQRLFQQVPHQFCNTVCRVGFHRMYSTSYNPVYGAGIYFTKSLKNLADKV
KKTSSTDKLIYVFEAEVLTGSFCQGNSSNIIPPPLSPGALDVNDSVVDNVSSPETIVVFNGMQAMP
LYLWTCTQDRTFSQHPMWSQDYSSGPGMVSSLQSWEWVLNGSSV
```

Fig. 2 (continued)

```
>_ BAL Human protein                              819 aa vs.
>_ BAL Mouse protein                              826 aa
scoring matrix: , gap penalties: -12/-2
61.5% identity;        Global alignment score: 3158

10        20        30        40        50        60
610015  MDFSMVAGAAAYNEKSETGALGENYSWQIPINHNDFKILKNNERQLCEVLQNKFGCISTL
        ::    .  :::  :.   ...:  :.: ::::::.::  :..:::.:: :::::::::::::::::
        MD----TWAAAPAERPANNSLEEHYRWQIPIKHNVFEILKSNESQLCEVLQNKFGCISTL
                  10        20        30        40        50

70        80        90       100       110
610015  VSPVQEGNSKSLQ-VFRKMLTPRIELSVWKDDLTTHAVDAVVNAANEDLLHGGGLALALV
        :.   :::..  :    : :::.  :  : ::::::::::  :..::::::::..::::.:::  .::
        SCPTLAGSSSPAQRVFRRTLIPGIELSVWKDDLTRHVVDAVVNAANENLLHGSGLAGSLV
        60        70        80        90       100       110

120       130       140       150       160       170
610015  KAGGFEIQEESKQFVARYGKVSAGEIAVTGAGRLPCKQIIHAVGPRWMEWDKQGCTGKLQ
        :..::::::::...:    :::.:.:  ::..:::::::::..  ::::::::::.   ...:    :..
        KTGGFEIQEESKRIIANVGKISVGGIAITGAGRLPCHLIIHAVGPRWTVTNSQTAIELLK
             120       130       140       150       160       170

180       190       200       210       220       230
610015  RAIVSILNYVIYKNTHIKTVAIPALSSGIFQFPLNLCTKTIVETIRVSLQGKPMMSNLKE
        ::  .::.::   . .::::::::::::::::.:::.  :.:::::.  ..:  : :..::..:
        FAIRNILDYVTKYDLRIKTVAIPALSSGIFQFPLDLCTSIILETIRLYFQDKQMFGNLRE
             180       190       200       210       220       230

240       250       260       270       280       290
610015  IHLVSNEDPTVAAFKAASEFILGK---SELGQETTP--SFNAMVVNNLTLQIVQGHIEWQ
        ::::::::::::::.:.:::: :::.    :  :: ::    ...   .::::::.  :
        IHLVSNEDPTVASFKSASESILGRDLSSWGGPETDPASTMTLRIGRGLTLQIVQGCIEMQ
             240       250       260       270       280       290

300       310       320       330       340       350
610015  TADVIVNSVNPHDITVGPVAKSILQQAGVEMKSEFLATKAKQFQRSQLVLVTKGFNLFCK
        :..::: ::   .:.    : ::.:::.:::::::.:.   :...    : : :::::.: :.
        TTDVIGNSGYMQDFKSGRVAQSILRQAGVEMEKEL--DKVNLSTDYQEVWVTKGFKLSCQ
        300       310       320       330       340       350

360       370       380       390       400       410
610015  YIYHVLWHSEFPKPQILKHAMKECLEKCIEQNITSISFPALGTGNMEIKKETAAEILFDE
        :...::  :::::.. :  ::::  ::::::::..  .:.:::::::::  :...:::.:..:
        YVFHVAWHSQINKYQILKDAMKSCLEKCLKPDINSISFPALGTGLMDLKKSTAAQIMFEE
             360       370       380       390       400       410

420       430       440       450       460       470
610015  VLTFAKDHVKHQLTVKFVIFPTDLEIYKAFSSEMAKRSKMLSLNNYS---VPQSTREEKR
        :...::.:  .. :::::::.: ::  : .:::.:.: :..... : ...    . :  ..:
        VFAFAKEHKEKTLTVKIVIFPVDVETYKIFYAEMTKRSNELNLSGNSGALALQWSSGEQR
             420       430       440       450       460       470
```

Fig. 3

```
        480        490        500        510        520        530
610015 ENGLEARSPAINLMGFNVEEMYEAHAWIQRILSLQNHHIIENNHILYLGRKEHDILSQLQ
       ..:::  :::::::::  .:  ::  ::.  ::..:.:    .::::::::::::::..:::.::.::
     - RGGLEAGSPAINLMGVKVGEMCEAQEWIERLLVSLDHHIIENNHILYLGKKEHDVLSELQ
        480        490        500        510        520        530

540        550        560        570        580        590
610015 KTSSVSITEIISPGRTELEIEGARADLIEVVMNIEDMLCKVQEEMARKKERGLWRSLGQW
       ..  :::..:  .::   :::.:  .:::::..::  ::  :::  :::::.:  :.:.:::   ::
     - TSTRVSISETVSPRTATLEIKGPQADLIDAVMRIECMLCDVQEEVAGKREKNLWSLSGQG
        540        550        560        570        580        590

600        610        620        630        640        650
610015 TIQQQKTQDEMKENIIFLKCPVPPTQELLDQKKQFEKCGLQVLKVEKIDNEVLMAAFQRK
       :  ::.:  :..:.  :  .  :.  ::::  ::::::::::  :...::.::..:::.:
     - TNQQEKL-DKMEESYTFQRYPASLTQELQDRKKQFEKCGLWVVQVEQIDNKVLLAAFQEK
        600        610        620        630        640        650

660        670        680        690        700        710
610015 KKMMEEKLHRQPVSHRLFQQVPYQFCNVVCRVGFQRMYSTPCDPKYGAGIYFTKNLKNLA
       :::::::.   .   :.::::::::.::::..:::::  .:  ::::::::::.:::::
     - KKMMEERTPKGSGSQRLFQQVPHQFCNTVCRVGFHRMYSTSYNPVYGAGIYFTKSLKNLA
        660        670        680        690        700        710

720        730        740        750        760        770
610015 EKAKKISAADKLIYVFEAEVLTGFFCQGHPLNIVPPPLSPGAIDGHDSVVDNVSSPETFV
       .:..::  :..:::::::::::::::::::  ::::.   ::.::::::::.  .::::::::::.:
     - DKVKKTSSTDKLIYVFEAEVLTGSFCQGNSSNIIPPPLSPGALDVNDSVVDNVSSPETIV
        720        730        740        750        760        770

780        790        800        810
610015 IFSGMQAIPQYLWTCTQE--YVQ----SQDYSSGPMRPFAQHPWRGFASGSPVD
       .::::::..:  :::::::::.   .  :    ::::::::   ..  :.    .::  :
     - VFNGMQAMPLYLWTCTQDRTFSQHPMWSQDYSSGPGMVSSLQSWEWVLNGSSV-
        780        790        800        810        820
```

Fig. 3 (continued)

Comparison of:
(A) 7486572155.52.67.361 >_ BAL Human          3244n
(B) 7486572155.52.67.362 >_ BAL Mouse          3024n
using matrix file: DNA, gap penalties: -16/-4

71.7% identity in 2916 nt overlap; score: 5444

```
        370       380       390       400       410       420
   CCCTACAAGTGCTCAGAGACTGGTGCTCTTGGAGAAAACTATAGTTGGCAAATTCCCATT
   :::  : :   :  :::   :    : :::::: ::::  : :::::  ::::::::::::::
   CCCGCCGAAAGACCAGCCAACAATTCTCTTGAAGAACATTATAGATGGCAAATTCCCATT
        200       210       220       230       240       250

430       440       450       460       470       480
   AACCACAATGACTTCAAAAATTTTAAAAAATAATGAGCGTCAGCTGTGTGAAGTCCTCCAG
   ::  :::::::: ::::  :::::::::::  :   :::::: :::::::   ::::::::::::::
   AAACACAATGTCTTCGAAATTTTAAAGAGCAATGAGAGTCAGCTATGTGAAGTCCTCCAA
        260       270       280       290       300       310

490       500       510       520       530       540
   AATAAGTTTGGCTGTATCTCTACCCTGGTCTCTCCAGTTCAGGAAGGCAACAGCAAATCT
   ::::::::::::  ::  :::::::::::::    ::  ::::  ::    :   :  ::::        ::
   AATAAGTTTGGATGCATCTCTACCCTGAGCTGTCCAACTCTAGCAGGGAGCAGCTCTCCT
        320       330       340       350       360       370

550       560       570       580       590       600
   CTGCA---AGTGTTCAGAAAAATGCTGACTCCTAGGATAGAGTTATCAGTCTGGAAAGAT
    ::    :::  ::::::::  :    ::::   ::: :::::::::::::: ::::::::: :::
   GCTCAGAGAGTCTTCAGAAGGACCCTGATCCCTGGGATAGAGTTATCTGTCTGGAAGGAT
        380       390       400       410       420       430

610       620       630       640       650       660
   GACCTCACCACACATGCTGTTGATGCTGTGGTGAATGCAGCCAATGAAGATCTTCTGCAT
   :::::  ::::  :::  :  ::::::::::::::::::::  :::::::::::::  :  :::  :::::
   GACCTTACCAGACACGTTGTTGATGCTGTGGTGAACGCAGCCAATGAAAACCTTTTGCAT
        440       450       460       470       480       490

670       680       690       700       710       720
   GGGGGAGGCCTGGCCCTGGCCCTGGTAAAAGCTGGTGGATTTGAAATCCAAGAAGAGAGC
   ::  :  :::::::::::   :  :::: :::  :::::::::  ::::::::::::::::::::::::::
   GGAAGTGGCCTGGCCGGAACCTTGGTGAAAACTGGTGGCTTTGAAATCCAAGAAGAGAGC
        500       510       520       530       540       550

730       740       750       760       770       780
   AAACAGTTTGTTGCCAGATATGGTAAAGTGTCAGCTGGTGAGATAGCTGTCACGGGAGCA
   :::   :  :::::::    :::::::: :  ::::  :::::   ::  :::  ::::  ::  ::
   AAAAGAATCATTGCCAACGTTGGTAAAATCTCAGTTGGTGGAATCGCTATCACCGGTGCG
        560       570       580       590       600       610
```

Fig. 4

```
       790        800        810        820        830        840
GGGAGGCTTCCCTGCAAACAGATCATCCATGCTGTTGGGCCTCGGTGGATGGAATGGGAT
::::: :::::  ::: :     ::: :::::::::  :::::  :::::::::::::   :     : :
GGGAGACTTCCTTGCCATTTGATTATCCATGCGGTTGGACCTCGGTGGACAGTTACGAAC
       620        630        640        650        660        670

850        860        870        880        890        900
AAACAGGGATGTACTGGAAAGCTGCAGAGGGCCATTGTAAGTATTCTGAATTATGTCATC
:  ::: :  ::  : :    ::: :      :::::::  : :::::  :::::::::: :
AGCCAGACAGCTATCGAATTACTGAAATTTGCCATTAGGAACATTCTAGATTATGTCACC
       680        690        700        710        720        730

910        920        930        940        950        960
TATAAAAATACTCACATTAAGACAGTAGCAATTCCAGCCTTGAGCTCTGGGATTTTTCAG
 :  : ::     :  :::::::::::::::::::::::::::  :::::::::: ::::: :::
AAATATGATCTACGCATTAAGACAGTAGCAATTCCAGCCCTGAGCTCTGGAATTTTCCAG
       740        750        760        770        780        790

970        980        990       1000       1010       1020
TTCCCTCTGAATTTGTGTACAAAGACTATTGTAGAGACTATCCGGGTTAGTTTGCAAGGG
:::::::::  :::::::::::   :   ::: :::: :::::::::: ::   :::  ::::
TTCCCTCTGGATTTGTGTACAAGCATAATTTTAGAAACTATCCGGCTTTATTTCCAAGAC
       800        810        820        830        840        850

1030       1040       1050       1060       1070       1080
AAGCCAATGATGAGTAATTTGAAAGAAATTCACCTGGTGAGCAATGAGGACCCTACTGTT
::::  :::::  :   :::::::::::  :::::  :::::::::::::::::::::  :::::::
AAGCAAATGTTCGGTAATTTGAGAGAGATTCATCTGGTGAGCAATGAGGACCCCACTGTT
       860        870        880        890        900        910

1090       1100       1110       1120       1130
GCTGCCTTTAAAGCTGCTTCAGAATTCATCCTAGGGAAGAG--TGAGCT-------GGGA
::  :::::::::: : :: ::::::::  :::::::::::::: :     ::::::          :::
GCGTCCTTTAAATCCGCCTCAGAAAGCATCCTAGGGAGGGACCTGAGCTCTTGGGGGGGT
       920        930        940        950        960        970

1140       1150       1160       1170       1180
CAAGAAACCACCCCTTCTTTCA--ATG-CAATGGTCGTGAACAA---CCTGACCCTCCAG
: :::::::     :::: :::  ::   ::: :   :    : :   :     ::::::  ::::::
CCAGAAACTGACCCTGCTTCCACCATGACTCTTCGCATCGGCCGGGGCCTGACTCTCCAG
       980        990       1000       1010       1020       1030

1190       1200       1210       1220       1230       1240
ATTGTCCAGGGCCACATTGAATGGCAGACGGCAGATGTAATTGT[AATTCTGTAAACCCA
:::::::::: :::   ::::::    :::  ::  :::::::::::::: :::::::::::::    : ::
ATTGTCCAAGGCTGTATTGAAATGCAAACAACAGATGTAATTGGTAATTCTGGATACATG
      1040       1050       1060       1070       1080       1090
```

Fig. 4 (continued)

```
      1250       1260       1270       1280       1290       1300
  CATGATATTACAGTTGGACCTGTGGCAAAGTCAATTCTACAACAAGCAGGAGTTGAAATG
  ::  :::  :::  :      ::::    ::::::   ::::  :::::   :::::::::: :::::::::
  CAGGATTTTAAATCAGGACGAGTGGCACAGTCGATTCTTAGACAAGCAGGGGTTGAAATG
      1100       1110       1120       1130       1140       1150

1310       1320       1330       1340       1350       1360
  AAATCGGAATTTCTTGCCACAAAGGCTAAACAGTTTCAACGGTCCCAGTTGGTACTGGTC
  ::    ::::     ::::  ::    :::  :::  :  ::       :    ::   :::     ::::
  GAAAAGGAA---CTTGACA---AGGTTAACCTGTCCACAGATTATCAAGAGGTGTGGGTC
       1160       1170       1180       1190       1200

1370       1380       1390       1400       1410       1420
  ACAAAAGGATTTAACTTGTTCTGTAAATATATATACCATGTACTGTGGCATTCAGAATTT
  ::::::::::::::  ::::  ::::  :  :::  :  ::::::    :::::::::  ::  :
  ACAAAAGGATTTAAAATTGTCCTGTCAGTATGTCTTCCATGTGGCATGGCATTCCCAAATC
      1210       1220       1230       1240       1250       1260

1430       1440       1450       1460       1470       1480
  CCTAAACCTCAGATATTAAAACATGCAATGAAGGAGTGTTTGGAAAAATGCATTGAGCAA
  :::    :::::::::  :::  ::::::::::::   :::  :  :::::::::::  ::  :  :  :
  AACAAATACCAGATATTGAAAGATGCAATGAAGTCCTGTCTAGAAAAATGCCTTAAACCA
      1270       1280       1290       1300       1310       1320

1490       1500       1510       1520       1530       1540
  AATATAACTTCCATTTCCTTTCCTGCCCTTGGGACTGGAAACATGGAAATAAAGAAGGAA
  ::::::   :::::::::::::::::  ::  :::::  :::      :::::   :  ::::::
  GATATAAATTCCATTTCCTTTCCTGCTCTCGGGACAGGATTGATGGATTTGAAGAAGAGT
      1330       1340       1350       1360       1370       1380

1550       1560       1570       1580       1590       1600
  ACAGCAGCAGAGATTTTGTTTGATGAAGTTTTAACATTTGCCAAAGACCATGTAAAACAC
  :::::::   ::::   ::::::::  ::::::::   :::::::  :::::  ::       ::  :
  ACAGCAGCTCAGATAATGTTTGAGGAAGTTTTTGCATTTGCTAAAGAGCACAAGGAAAAA
      1390       1400       1410       1420       1430       1440

1610       1620       1630       1640       1650       1660
  CAGTTAACTGTAAAATTTGTGATCTTTCCAACAGATTTGGAGATATATAAGGCTTTCAGT
  :   :::::::::   :::::::::::::::  ::::  ::::::  ::  :::  :::     :
  ACGCTAACTGTAAAGATTGTGATCTTTCCAGTAGATGTGGAGACGTACAAGATTTTTTAT
      1450       1460       1470       1480       1490       1500

1670       1680       1690       1700       1710
  TCTGAAATGGCAAAGAGGTCCAAGATGCTGAGTTTGAACAATTACAGTGT---------C
  :::::::::  ::::  :::::::::     :::::  :  :::  :  :  ::::      :
  GCTGAAATGACAAAAAGGTCCAACGAGCTGAATCTCAGCGGTAATAGTGGTGCTTTAGCC
      1510       1520       1530       1540       1550       1560
```

Fig. 4 (continued)

```
1720       1730       1740       1750       1760       1770
CCCCAGTCAACCAGAGAGGAGAAAAGAGAAAATGGGCTTGAAGCTAGATCTCCTGCCATC
 :  : ::   : :::  :  : :::  :::::    :   ::  :::::::::: ::::::::::::::
CTGCAGTGGTCCAGTGGGGAGCAAAGAAGAGGCGGCCTTGAAGCTGGATCTCCTGCCATC
   1570       1580       1590       1600       1610       1620

1780       1790       1800       1810       1820       1830
AATCTGATGGGATTCAACGTGGAAGAGATGTAGTGAGGCCCACGCATGGATCCAAAGAAT
::::: :::::  : ::  ::::  ::::::::: :::::::::::: : ::::::  ::::  :
AATCTCATGGGTGTAAAAGTGGGAGAGATGT-GTGAGGCCCAGGAATGGATTGAAAGGTT
   1630       1640       1650       1660       1670       1680

1840       1850       1860       1870       1880       1890
CCTGAGTCTCCAGAACCACCACATCATTGAGAATAATCATATTCTGTACCTTGGGAGAAA
 :::    ::  :  :::::::::::::::::::::::::::::::::::::  ::  :::::::: :::
GCTGGTCTCCCTGGACCACCACATCATTGAGAATAATCATATTCTCTATCTTGCGAAAAA
   1690       1700       1710       1720       1730       1740

1900       1910       1920       1930       1940       1950
GGAACATGACATTTTGTCTCAGCTTCAGAAAACTTCAAGTGTCTCCATCACAGAAATTAT
 :: ::  ::: : ::::: :::: :::: :    :::: :::::::::  ::::  :  :  :
AGAGCACGACGTGCTGTCTGAGCTCCAGACCAGCACAAGAGTCTCCATTTCAGAGACTGT
   1750       1760       1770       1780       1790       1800

1960       1970       1980       1990       2000       2010
CAGCCCAGGAAGGACAGAGTTAGAGATTGAAGGAGCCCGGGCTGACCTCATTGAGGTGGT
:::  :::  ::: : :      ::  ::::::  ::::   ::: :::::::::::::::   :  ::
CAGTCCAAGAACGGCCACTTTGGAGATTAAAGGTCCCCAGGCTGACCTCATTGACGCAGT
   1810       1820       1830       1840       1850       1860

2020       2030       2040       2050       2060       2070
TATGAACATTGAAGATATGCTTTGTAAAGTACAGGAGGAAATGGCAAGGAAAAAGGAGCG
:::::  ::::::  ::::::  ::: : ::  :::::  ::: :::::  :  ::::  ::::
TATGAGGATTGAATGTATGCTGTGTGACGTTCAGGAAGAAGTGGCAGGAAAAAGGGAGAA
   1870       1880       1890       1900       1910       1920

2080       2090       2100       2110       2120       2130
AGGCCTTTGGCGCTCGTTAGGACAGTGGACTATTCAGCAACAAAAAACCCAAGACGAAAT
 :   :::::::  ::: ::  :::::::  :::: :   ::::::  :::::   :  ::  ::::
AAATCTTTGGAGCTTGTCAGGACAGGGGACCAACCAGCAAGAAAAA---CTGGATAAAAT
   1930       1940       1950       1960       1970       1980

2140       2150       2160       2170       2180       2190
GAAAGAAAATATCATATTTCTGAAATGTCCTGTGCCTCCAACTCAAGAGCTTCTAGATCA
 : :::::   ::  ::::::   ::  :: :    :   :      ::::::: :: ::::   :: :
GGAAGAATCGTACACATTTCAACGATACCCAGCATCATTAACTCAGGAACTTCAGGACCG
   1990       2000       2010       2020       2030       2040
```

Fig. 4 (continued)

```
2200      2210      2220      2230      2240      2250
AAAGAAACAGTTTGAAAAATGTGGTTTGCAGGTTCTAAAGGTGGAGAAGATAGACAATGA
::::::::::::::::::  :::::  :::    ::::  :   :::::::  ::::::::::::: :
AAAGAAACAGTTTGAAAAGTGTGGCTTGTGGGTTGTGCAGGTGGAGCAGATAGACAATAA
      2050      2060      2070      2080      2090      2100

2260      2270      2280      2290      2300      2310
GGTCCTTATGGCTGCCTTTCAAAGAAAGAAGAAAATGATGGAAGAAAAACTGCACAGGCA
:::  ::   :::::::::::  :::          ::::::::::::::::::::  :   ::   : :
GGTGCTGCTGGCTGCCTTCCAAGAGAAGAAGAAAATGATGGAAGAGAGGACGCCAAAGGG
      2110      2120      2130      2140      2150      2160

2320      2330      2340      2350      2360      2370
ACCTGTGAGCCATAGGCTGTTTCAGCAAGTCCCATACCAGTTCTGCAATGTGGTATGCAG
: :::  ::::::  :::  :::::::::::   ::::::  :  :::::::::::::  :::   :::::
ATCTGGGAGCCAAAGGTTGTTTCAGCAGGTCCACATCAGTTCTGCAATACGGTGTGCAG
      2170      2180      2190      2200      2210      2220

2380      2390      2400      2410      2420      2430
AGTTGGCTTTCAAAGAATGTACTCGACACCTTGCGATCCAAAATACGGAGCTGGCATATA
:::  :::::  ::  :::::::::  ::::::  : :     :  :::    ::  :::::  :::::::::
AGTCGGCTTCCACAGAATGTATTCGACATCCTATAACCCAGTTTATGGAGCCGGCATATA
      2230      2240      2250      2260      2270      2280

2440      2450      2460      2470      2480      2490
CTTCACCAAGAACCTCAAAAACCTGGCAGAGAAGGCCAAGAAAATCTCTGCTGCAGATAA
:::::::::  :::::::::  ::  :::::  ::::   :::::::::  :::       ::::  ::
TTTCACCAAGAGCCTCAAAAATCTAGCAGACAAGGTCAAGAAAACCTCAAGCACAGACAA
      2290      2300      2310      2320      2330      2340

2500      2510      2520      2530      2540      2550
GCTGATCTATGTGTTTGAGGCTGAAGTACTCACAGGCTTCTTCTGCCAGGGACATCCGTT
:::  :::::::::::::::::  :::::::::::::: :  ::::::  :::::  ::   :   :
GCTAATCTATGTGTTTGAGGCAGAAGTACTCACAGGGTCCTTCTGTCAGGGTAATTCCTC
      2350      2360      2370      2380      2390      2400

2560      2570      2580      2590      2600      2610
AAATATTGTTCCCCCACCACTGAGTCCTGGAGCTATAGATGGTCATGACAGTGTGGTTGA
::::::  :  ::  :::::::::  ::::::::::  ::::::   ::::::::  ::  :::::
AAATATCATCCCTCCACCATTGAGTCCTGGGGCCTTAGATGTCAATGACAGCGTAGTTGA
      2410      2420      2430      2440      2450      2460

2620      2630      2640      2650      2660      2670
CAATGTCTCCAGCCCTGAAACCTTTGTTATTTTTAGTGGCATGCAGGCTATACCTCAGTA
::::::   ::::::::::::::::::  :::::   ::::::::::::::::  ::  ::  :::
CAATGTTTCCAGCCCTGAAACCATTGTTGTTTTTAATGGCATGCAGGCCATGCCCCTGTA
      2470      2480      2490      2500      2510      2520
```

Fig. 4 (continued)

```
2680       2690       2700                      2710       2720
TTTGTGGACATGCACCCAGGA----ATATGTACA-------------GTCACAAGATTA
::::::::: ::::: :::::    : ::    ::             :::::: :: ::
CTTGTGGACTTGCACACAGGATAGGACATTCTCACAGCATCCGATGTGGTCACAGGACTA
     2530       2540       2550       2560       2570       2580

2730       2740       2750       2760       2770       2780
CTCATCAGGACCAATGAGACCCTTTGCACAGCATCCTTGGAGGGGATTCGCAAGTGGCAG
:::::::::::::    :   :: : :  :::   : :::    :  ::   ::  ::::::
CTCATCAGGACCAGGAATGGTCTCTTCGCTGCAGTCCTGGGAATGGGTCTTAAATGGCAG
     2590       2600       2610       2620       2630       2640

2790       2800       2810       2820       2830       2840
CCCTGTTGATTAATCTCTACATCATTTTAACAGCTGGTATGGCCTTACCTTGGGTGAACT
:  ::::     :::  : ::::::::::: ::::::::      :  : ::       ::: :  :::::
CTCTGT---TTAGTGTCTACATCAGTTTAACAAGCAGAAGGGG------TTGAGAGAACT
          2650       2660       2670       2680            2690

2850       2860       2870       2880       2890       2900
AACCAAATAATGACCATCGATGGCTCAAAGAGTGGCTTGAATATATCCCATGGGTTATCT
::  ::::  ::                        :::  :                :   ::::: ::
GACAAAATGAT--------------AAATA-----------------ACAGGTTACCT
     2700                                                  2710

2910       2920       2930       2940       2950       2960
GTATGGACTGACTGGGTTATTGAAAGGACTAGCCACATACTAGCATCTTAGTGCCTTTAT
::    ::   :::    ::::  :  :  ::  ::          :::::   :::::::::::   :::::::::::
GTTCAGAATGATGGGGTCACTAAAGGCACCGACCACACACTAGCATCATAGTGCCTTT--
2720      2730       2740       2750       2760       2770

2970       2980       2990       3000       3010       3020
CTGTCTTTATGTCTTGGGGTTGGGGTAGGTAGATACCAAATGAAACACTTTCAGGACCTT
:::::::  :::   :::  :  :   :  : :   ::::  :::  : ::::   :::   ::  :
--GTCTTTACCTCT--GGGCTTGACTGGGCAGATGCCAGCTAAAAC---TTCCTCACTGT
     2780       2790       2800       2810       2820       2830

3030       3040       3050       3060       3070
CCTTCCTCTTGCAGTTGTTCTTTAATCTCCTTTACTAGAGGAGATA-----AATATTTTG
: ::  :: ::   :    :::::  ::::::::::: :::  ::: :: :           :::: :::
CTTTTCTATTTGACA---TCTTTCATCTCCTTTCCTATAGGTGACAGCAAGAATACTTTA
     2840           2850       2860       2870       2880
```

Fig. 4 (continued)

```
3080      3090      3100      3110      3120      3130
CATATAATGAAGAAATTTTTCTAGTATATAACGCAGGCCTTTTATTTTCTAAAATGATGA
 ::: ::   : ::  ::::::  :             ::  ::::  :::::::::::::::
TATAGAACAAGGATATTTTTTT----------CAAGCCTGTTATTTTCTAAAATGA---
2890      2900                3910      2920      2930

3140      3150      3160      3170      3180      3190
TAGTATAAAAATGTTAGGATAACAGAATGATTTTAGATTTTCCAGAGAATATTATAAAGT
 ::: : :::        :::::  :::::  :::::::  ::   :::::  : : :::  :::::::::
TAGCACAAAC----TAGGACAACAGGATGATTTCAGGTTTTCTATATAAT-TTATAAAGT
   2940          2950      2960      2970      2980

3200      3210      3220      3230
GCTTTAGGTATGAAAATAAATCATCTTTGTCTGATT
::::: : :::  :::::::::::  ::::::::::: :
GCTTTGGATATCCAAATAAATCACCTTTGTCTGAGT
2990      3000      3010      3020
```

Fig. 4 (continued)

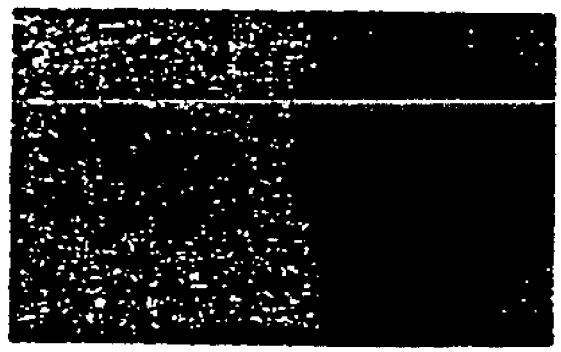
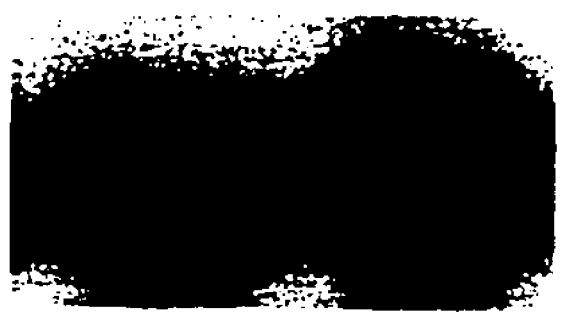
Fig. 6

LYMPHOMA ASSOCIATED MOLECULES AND USES THEREFOR

GOVERNMENT FUNDING

Work described herein was supported, at least in part, under grant 1P01CA66996-01A1 awarded by the NIH. The U.S. government therefore may have certain rights in this invention.

BACKGROUND OF THE INVENTION

The incidence of non-Hodgkin's lymphoma in the United States has increased by 75.1% between 1973 and 1992 (Kosary et al., *SEER Cancer Statistics Review,* 1973-1992: *Tables and Graphs, National Cancer Institute,* NIH Publication No 96-2789, Bethesda, Md.: NIH 1995), a percentage increase exceeded only by that for prostate cancer, lung cancer in women, and melanoma.

Diffuse large B-cell lymphoma (DLB-CL) is the most common non-Hodgkin's lymphoma in adults. Although DLB-CL is curable in approximately 40% of patients, the majority of patients progress and die of their disease (Shipp et al. Non-Hodgkin's Lymphomas. In DeVita (ed): Principles and Practice of Oncology, 5th Edition, Philadelphia, J. B. Lippincott Company. pp. 2165-2220, 1997). Additional advancements in the treatment of this aggressive but potentially curable non-Hodgkin's lymphoma are likely to require a more precise understanding of the disease's cellular and molecular bases.

SUMMARY OF THE INVENTION

To identify genes which contribute to the observed differences in clinical outcome in DLB-CLs, the technique of differential display (Liang P. et al. (1992) *Science,* 257:967) was used in panels of primary tumors from patients with known clinical prognostic characteristics and mature follow-up. A novel 3' cDNA, termed BAL, was found to be significantly more abundant in tumors from patients with "high-risk (HR)" (International Prognostic Index, IPI) fatal disease than in tumors from cured "low risk (LR [IPI])" patients (Shipp M. et al. (1993) *N. Engl. J. Med.,* 329:987-994).

Accordingly, the present invention is based, at least in part, on the discovery of novel molecules which are differentially expressed in tumors from patients with "high risk" fatal DLB-CL disease or "low risk" cured DLB-CL. Their differentially expressed gene products are referred to herein as the "B-aggressive lymphoma" ("BAL") nucleic acid and protein. The BAL molecules of the present invention are useful as modulating agents for regulating a variety of cellular processes. Accordingly, in one aspect, this invention provides isolated nucleic acid molecules encoding BAL proteins or biologically active portions thereof, as well as nucleic acid fragments suitable as primers or hybridization probes for the detection of BAL-encoding nucleic acids.

In one embodiment, a BAL nucleic acid molecule of the invention is at least 50%, 55%, 60%, 65%, 70%, 72%, 75%, 80%, 85%, 90%, 95%, 98%, or more identical to the nucleotide sequence (e.g., to the entire length of the nucleotide sequence) shown in SEQ ID NO:1, 3, 4, or 6.

In a preferred embodiment, the isolated nucleic acid molecule includes the nucleotide sequence shown SEQ ID NO:1 or 3, or a complement thereof. In another embodiment, the nucleic acid molecule includes SEQ ID NO:3 and nucleotides 1-228 of SEQ ID NO:1. In another embodiment, the nucleic acid molecule includes SEQ ID NO:3 and nucleotides 2791- 3243 of SEQ ID NO:1. In another preferred embodiment, the nucleic acid molecule consists of the nucleotide sequence shown in SEQ ID NO:1 or 3. In another preferred embodiment, the nucleic acid molecule includes a fragment of at least 607 nucleotides (e.g., 607 contiguous nucleotides) of the nucleotide sequence of SEQ ID NO:1 or 3, or a complement thereof.

In another preferred embodiment, the isolated nucleic acid molecule includes the nucleotide sequence shown SEQ ID NO:4 or 6, or a complement thereof. In another embodiment, the nucleic acid molecule includes SEQ ID NO:6 and nucleotides 1-170 of SEQ ID NO:4. In another embodiment, the nucleic acid molecule includes SEQ ID NO:6 and nucleotides 2649-3024 of SEQ ID NO:4. In another preferred embodiment, the nucleic acid molecule consists of the nucleotide sequence shown in SEQ ID NO:4 or 6. In another preferred embodiment, the nucleic acid molecule includes a fragment of at least 452 nucleotides (e.g., 452 contiguous nucleotides) of the nucleotide sequence of SEQ ID NO:4, SEQ ID NO:6, or a complement thereof.

In another embodiment, a BAL nucleic acid molecule includes a nucleotide sequence encoding a protein having an amino acid sequence sufficiently homologous to the amino acid sequence of SEQ ID NO:2 or 5. In a preferred embodiment, a BAL nucleic acid molecule includes a nucleotide sequence encoding a protein having an amino acid sequence at least 50%, 55%, 60%, 62%, 65%, 70%, 75%, 80%, 85%, 90%, 95%, 98% or more homologous to the entire length of the amino acid sequence of SEQ ID NO:2 or 5.

In another preferred embodiment, an isolated nucleic acid molecule encodes the amino acid sequence of human BAL. In yet another preferred embodiment, the nucleic acid molecule includes a nucleotide sequence encoding a protein having the amino acid sequence of SEQ ID NO:2 or 5. In yet another preferred embodiment, the nucieic acid molecule is at least 452 or 607 nucleotides in length. In a further preferred embodiment, the nucleic acid molecule is at least 452 or 607 nucleotides in length and encodes a protein having a BAL activity (as described herein).

Another embodiment of the invention features nucleic acid molecules, preferably BAL nucleic acid molecules, which specifically detect BAL nucleic acid molecules relative to nucleic acid molecules encoding non-BAL proteins. For example, in one embodiment, such a nucleic acid molecule is at least 300-350, 350-400, 400-450, 452, 452-500, 500-550, 550-600, 607 or more nucleotides in length and hybridizes under stringent conditions to a nucleic acid molecule comprising the nucleotide sequence shown in SEQ ID NO:1 or 4 or a complement thereof.

In preferred embodiments, the nucleic acid molecules are at least 15 (e.g., contiguous) nucleotides in length and hybridize under stringent conditions to nucleotides 1-333, 351-385, 463-824, 931-1082, or 3232-3244 of SEQ ID NO:1. In other preferred embodiments, the nucleic acid molecules comprise nucleotides 1-333, 351-385, 463-824, 931-1082, or 3232-3244 of SEQ ID NO:1.

In other preferred embodiments, the nucleic acid molecules are at least 15 (e.g., contiguous) nucleotides in length and hybridize under stringent conditions to nucleotides 1-39 or 57-1841 of SEQ ID NO:4. In other preferred embodiments, the nucleic acid molecules comprise nucleotides 1-39 or 57-1841 of SEQ ID NO:4.

In other preferred embodiments, the nucleic acid molecule encodes a naturally occurring allelic variant of a polypeptide comprising the amino acid sequence of SEQ ID NO:2 or 5, wherein the nucleic acid molecule hybridizes to a nucleic acid molecule comprising SEQ ID NO:1, 3, 4, or 6 under stringent conditions.

Another embodiment of the invention provides an isolated nucleic acid molecule which is antisense to a BAL nucleic acid molecule, e.g., the coding strand of a BAL nucleic acid molecule.

Another aspect of the invention provides a vector comprising a BAL nucleic acid molecule. In certain embodiments, the vector is a recombinant expression vector. In another embodiment, the invention provides a host cell containing a vector of the invention. In yet another embodiment, the invention provides a host cell containing a nucleic acid molecule of the invention. The invention also provides a method for producing a protein, preferably a BAL protein, by culturing in a suitable medium, a host cell, e.g., a mammalian host cell such as a non-human mammalian cell, of the invention containing a recombinant expression vector, such that the protein is produced.

Another aspect of this invention features isolated or recombinant BAL proteins and polypeptides. In one embodiment, the isolated protein, preferably a BAL protein, includes at least one proline rich domain. In a preferred embodiment, the isolated protein, preferably a BAL protein, includes at least one proline rich domain and at least one tyrosine phosphorylation site. In a preferred embodiment, the protein, preferably a BAL protein, includes at least one proline rich domain, at least one tyrosine phosphorylation site, and has an amino acid sequence at least about 50%, 55%, 60%, 62%, 65%, 70%, 75%, 80%, 85%, 90%, 95%, 98% or more homologous to the amino acid sequence of SEQ ID NO:2 or 5. In another preferred embodiment, the protein, preferably a BAL protein, includes at least one proline rich domain, at least one tyrosine phosphorylation site, and plays a role in the pathogenesis of non-Hodgkin's lymphoma. In yet another preferred embodiment, the protein, preferably a BAL protein, includes at least one proline rich domain, at least one tyrosine phosphorylation site, and is encoded by a nucleic acid molecule having a nucleotide sequence which hybridizes under stringent hybridization conditions to a nucleic acid molecule comprising the nucleotide sequence of SEQ ID NO:1, 3, 4, or 6.

In another embodiment, the invention features BAL proteins which are produced by recombinant DNA techniques. Alternative to recombinant expression, a BAL protein -or polypeptide can be synthesized chemically using standard peptide synthesis techniques, based on the amino acid sequence of SEQ ID NO:2 or 5.

In another embodiment, the invention features fragments of the protein having the amino acid sequence of SEQ ID NO:2 or 5, wherein the fragment comprises at least 15 amino acids (e.g., contiguous amino acids) of the amino acid sequence of SEQ ID NO:2 or 5. In another embodiment, the protein, preferably a BAL protein, has the amino acid sequence of SEQ ID NO:2 or 5, respectively.

In another embodiment, the invention features an isolated protein, preferably a BAL protein, which is encoded by a nucleic acid molecule consisting of a nucleotide sequence at least about 50%, 55%, 60%, 65%, 70%, 72%, 75%, 80%, 85%, 90%, 95%, 98% or more homologous to a nucleotide sequence of SEQ ID NO:1, 3, 4, or 6, or a complement thereof. This invention further features an isolated protein, preferably a BAL protein, which is encoded by a nucleic acid molecule consisting of a nucleotide sequence which hybridizes under stringent hybridization conditions to a nucleic acid molecule comprising the nucleotide sequence of SEQ ID NO:1, 3, 4, or 6, or a complement thereof.

The proteins of the present invention or portions thereof, e.g., biologically active portions thereof, can be operatively linked to a non-BAL polypeptide (e.g., heterologous amino acid sequences) to form fusion proteins. The invention further features antibodies, such as monoclonal or polyclonal antibodies, that specifically bind proteins of the invention, preferably BAL proteins. In addition, the BAL proteins or biologically active portions thereof can be incorporated into pharmaceutical compositions, which optionally include pharmaceutically acceptable carriers.

In another aspect, the present invention provides a method for detecting the presence of a BAL nucleic acid molecule, protein or polypeptide in a biological sample by contacting the biological sample with an agent capable of detecting a BAL nucleic acid molecule, protein or polypeptide such that the presence of a BAL nucleic acid molecule, protein or polypeptide is detected in the biological sample.

In another aspect, the present invention provides a method for detecting the presence of BAL activity in a biological sample by contacting the biological sample with an agent capable of detecting an indicator of BAL activity such that the presence of BAL activity is detected in the biological sample.

In another aspect, the invention provides a method for modulating BAL activity comprising contacting a cell capable of expressing BAL with an agent that modulates BAL activity such that BAL activity in the cell is modulated. In one embodiment, the agent inhibits BAL activity. In another embodiment, the agent stimulates BAL activity. In one embodiment, the agent is an antibody that specifically binds to a BAL protein. In another embodiment, the agent modulates expression of BAL by modulating transcription of a BAL gene or translation of a BAL mRNA. In yet another embodiment, the agent is a nucleic acid molecule having a nucleotide sequence that is antisense to the coding strand of a BAL mRNA or a BAL gene.

In one embodiment, the methods of the present invention are used to treat a subject having a disorder characterized by aberrant BAL protein or nucleic acid expression or activity, e.g., non-Hodgkin's lymphoma, by administering an agent which is a BAL modulator to the subject. In one embodiment, the BAL modulator is a BAL protein. In another embodiment the BAL modulator is a BAL nucleic acid molecule. In yet another embodiment, the BAL modulator is a peptide, peptidomimetic, or other small molecule. In a preferred embodiment, the disorder characterized by aberrant BAL protein or nucleic acid expression is a proliferative disorder, e.g., non-Hodgkin's lymphoma.

The present invention also provides a diagnostic assay for identifying the presence or absence of a genetic alteration characterized by at least one of (i) aberrant modification or mutation of a gene encoding a BAL protein; (ii) mis-regulation of the gene; and (iii) aberrant post-translational modification of a BAL protein, wherein a wild-type form of the gene encodes a protein with a BAL activity.

In another aspect the invention provides a method for producing or identifying a compound that binds to or modulates the activity of a BAL protein, by providing an indicator composition comprising a BAL protein having BAL activity, contacting the indicator composition with a test compound and determining the effect of the test compound on BAL activity in the indicator composition to produce or identify a compound that modulates the activity of a BAL protein.

Other features and advantages of the invention will be apparent from the following detailed description and claims.

BRIEF DESCRIPTION OF THE DRAWINGS

FIG. 1 depicts the cDNA sequence and predicted amino acid sequence of human BAL. The nucleotide sequence corresponds to nucleic acids 1 to 3243 of SEQ ID NO:1. The amino acid sequence corresponds to amino acids 1 to 826 of SEQ ID NO: 2. The coding region without the 5' and 3' untranslated regions of the human BAL gene is shown in SEQ ID NO:3.

FIG. 2 depicts the cDNA sequence and predicted amino acid sequence of murine BAL. The nucleotide sequence corresponds to nucleic acids 1 to 3024 of SEQ ID NO:4. The amino acid sequence corresponds to amino acids 1 to 826 of SEQ ID NO: 5. The coding region without the 5' and 3' untranslated regions of the murine BAL gene is shown in SEQ ID NO:6.

FIG. 3 depicts an alignment of the human BAL protein with the murine BAL protein using the ALIGN program (version 2.0), a PAM120 weight residue table, a gap length penalty of 12 and a gap penalty of 2.

FIG. 4 depicts an alignment of the human BAL nucleic acid molecule with the murine BAL nucleic acid molecule using the ALIGN program (version 2.0), a PAM120 weight residue table, a gap length penalty of 16 and a gap penalty of 4.

FIG. 6 depicts a northern blot comparing BAL transcripts in a tumor derived from a DLB-CL cell line grown in SCID mouse and the parental suspension cells. BAL is expressed at significantly higher levels in the tumor derived RNA than in the parental cell line. The β-actin blot demonstrates that loading does not account for the observed differences.

DETAILED DESCRIPTION OF THE INVENTION

Figure 5:
FIG. 5 depicts a northern blot analysis of total RNA from 5 DLB-CL cell lines, 4 "high-risk" and 5 "low-risk" primary tumors, and 2 pairs of normal B-splenocytes, with or without Ig-activation. A band of ~3.2 kb (arrow), corresponding to the BAL message, is detected at high levels in only one of the cell lines (DHL-7), in the "high-risk" tumors and Ig-activated splenocytes. BAL transcripts are less abundant in the "low-risk" primary tumors. Likewise, BAL is expressed at lower levels in the non-activated B-cells. The β-actin blot demonstrates that loading does not account for the differences in BAL expression.

The present invention is based, at least in part, on the discovery of novel molecules, referred to herein as BAL nucleic acid and protein molecules which are differentially expressed in malignancies such as lymphoma, e.g., non-Hodgkin's lymphoma. The newly identified BAL nucleic acid and protein molecules can be used to identify cells exhibiting or predisposed to a malignancy such as lymphoma, e.g., non-Hodgkin's lymphoma, thereby diagnosing subjects having, or prone to developing such disorders.

As used herein, a "malignancy" includes a cancerous uncontrolled growth of cells in an area of the body. Malignant cancers are typically classified by their microscopic appearance and the type of tissue from which they arise. Examples of malignancies include carcinomas, sarcomas, myelomas, chondrosarcomas, adenosarcomas, angiosarcomas, neuroblastomas, gliomas, medulloblastomas, erythroleukemias, and myelogenous leukemias.

As used herein, a "lymphoma" includes a malignant neoplastic disorder of lymphoreticular tissue which produces a distinct tumor mass. Lymphomas include tumors derived from the lymphoid lineage. Lymphomas usually arise in lymph nodes, the spleen, or other areas rich in lymphoid tissue. Lymphomas are typically subclassified as Hodgkin's disease and Non-Hodgkin's lymphomas, e.g., Burkitt's lymphoma, large-cell lymphoma, and follicular lymphoma.

As used herein, "differential expression" or "differentially expressed" includes both quantitative as well as qualitative differences in the temporal and/or cellular expression pattern of a gene, e.g., the BAL gene, among, for example, normal cells and cells from patients with "high risk" fatal DLB-CL disease or "low risk" cured DLB-CL. Genes which are differentially expressed can be used as part of a prognostic or diagnostic marker for the evaluation of subjects at risk for developing a malignancy such as a lymphoma, e.g., non-Hodgkin's lymphoma. Depending on the expression level of the gene, the progression state or the aggressiveness of the disorder can be evaluated. Methods for detecting the differential expression of a gene are described herein.

The BAL molecules comprise a family of molecules having certain conserved structural and functional features. The term "family" when referring to the protein and nucleic acid molecules of the invention is intended to mean two or more proteins or nucleic acid molecules having a common structural domain or motif and having sufficient amino acid or nucleotide sequence homology as defined herein. Such family members can be naturally or non-naturally occurring and can be from either the same or different species. For example, a family can contain a first protein of human origin, as well as other, distinct proteins of human origin or alternatively, can contain homologues of non-human origin. Members of a family may also have common functional characteristics.

For example, the family of BAL proteins comprise at least one "proline rich domain." As used herein, the term "proline rich domain" includes an amino acid sequence of about 4-6 amino acid residues in length having the general sequence X-Pro-X-X-Pro-X (where X can be any amino acid). Proline rich domains are usually located in a helical structure and bind through hydrophobic interactions to SH3 domains. SH3 domains recognize proline rich domains in both forward and reverse orientations. Proline rich domains are described in, for example, Sattler M. et al., *Leukemia* (1998) 12:637-644, the contents of which are incorporated herein by reference. BAL proteins of the invention preferably include at least one proline rich domain, but may contain two or more. Amino acid residues 781-786 of the human BAL and amino acid residues 748-753 of the murine BAL comprise proline rich domains.

In another embodiment, a BAL protein of the present invention is identified based on the presence of at least one "tyrosine phosphorylation site" in the protein or corresponding nucleic acid molecule. As used herein, the term "tyrosine phosphorylation site" includes an amino acid sequence of about 4 amino acid residues in length having the general sequence Tyr-X-X-X (where X can be any amino acid). The tyrosine in this domain is phosphorylated in response to a cellular stimulus, for example, in response to a hematopoietic growth factor (e.g., thrombopoietin, erythropoietin, or steel factor) stimulation. Tyrosine phosphorylation of cellular proteins plays a major role in cell signaling, e.g., hematopoietic cell signaling. Tyrosine phosphorylation sites are described in, for example, Sattler M. et al., *Leukemia* (1998) 12:637-644, the contents of which are incorporated herein by reference. BAL proteins of the invention include at least one or two tyrosine phosphorylation sites, but may contain three or more. Amino acid residues 392-395 and 495-498 of the human BAL comprise tyrosine phosphorylation sites.

In another embodiment, a BAL protein of the present invention is identified based on the presence of at least one "rod domain" in the protein or corresponding nucleic acid molecule. As used herein, the term "rod domain" includes an α-helical, filament forming structure that is made up of smaller repeating structures. The smallest repeating structure may contain seven amino acids in which small, generally hydrophobic amino acids are typically found in the first and fourth positions of the repeat. The seven amino acids form two turns of an α-helix and the first and fourth positions fall in the hydrophobic interior of the α-helix. Rod domains in alpha and beta cardiac myosin are described in, for example, Warrick et al. (1987) *Annual Rev. Cell Biol.* 3:379-421.

In another embodiment, a BAL protein of the present invention is identified based on the presence of at least one "α-helical region" in the protein or corresponding nucleic acid molecule that is homologous to the α-helical region of moesin, the most abundant ezrin-radixin-moesin (ERM) protein in lymphocytes. As used herein, the term "α-helical region" includes an amino acid sequence of about 10 to about 20 amino acids in length that forms an α-helix. The α-helical region of ezrin-radixin-moesin (ERM) proteins is described in, for example, Bretscher (1999) *Current Biology* 8(12):721-4.

Due to their homology to protein families such as myosin heavy chain and cytoskeleton linkers ezrin-radixin-moesin, the human BAL molecules may also be involved in cellular functions such as cell migration, motility, and shape, as well as in cell/cell and cell/extra-cellular matrix interactions through adhesion molecules.

Isolated proteins of the present invention, preferably BAL proteins, have an amino acid sequence sufficiently homologous to the amino acid sequence of SEQ ID NO:2 or 5 or are encoded by a nucleotide sequence sufficiently homologous to SEQ ID NO:1, 3, 4, or 6. As used herein, the term "sufficiently homologous" refers to a first amino acid or nucleotide sequence which contains a sufficient or minimum number of identical or equivalent (e.g., an amino acid residue which has a similar side chain) amino acid residues or nucleotides to a second amino acid or nucleotide sequence such that the first and second amino acid or nucleotide sequences share common structural domains or motifs and/or a common functional activity. For example, amino acid or nucleotide sequences which share common structural domains have at least 30%, 40%, or 50% homology, preferably 60% homology, more preferably 70%-80%, and even more preferably 90-95% homology across the amino acid sequences of the domains and contain at least one and preferably two structural domains or motifs, are defined herein as sufficiently homologous. Furthermore, amino acid or nucleotide sequences which share at least 30%, 40%, or 50%, preferably 60%, more preferably 70-80%, or 90-95% homology and share a common functional activity are defined herein as sufficiently homologous.

As used interchangeably herein, "BAL activity", "biological activity of BAL" or "functional activity of BAL", refers to an activity exerted by a BAL protein, polypeptide or nucleic acid molecule on a BAL responsive cell or on a BAL protein substrate, as determined in vivo, ex vivo, or in vitro, according to standard techniques. In one embodiment, a BAL activity is a direct activity, such as an association with a BAL-target molecule. As used herein, a "target molecule" or "binding partner" is a molecule with which a BAL protein binds or interacts in nature, such that BAL-mediated function is achieved. A BAL target molecule can be a non-BAL molecule or a BAL protein or polypeptide of the present invention. In an exemplary embodiment, a BAL target molecule is a BAL ligand. Alternatively, a BAL activity is an indirect activity, such as a cellular signaling activity mediated by interaction of the BAL protein with a BAL ligand. BAL activities include modulation of cellular adhesion and modulation of the aggressiveness or severity of a malignancy such as DLB-CL. BAL activities are described herein.

Accordingly, another embodiment of the invention features isolated BAL proteins and polypeptides having a BAL activity. Preferred proteins are BAL proteins having at least one tyrosine phosphorylation site and, preferably, a BAL activity. Other preferred proteins are BAL proteins having at least one proline rich domain and, preferably, a BAL activity. Other preferred proteins are BAL proteins having at least one tyrosine phosphorylation site and/or at least one proline rich domain, and are, preferably, encoded by a nucleic acid molecule having a nucleotide sequence which hybridizes under stringent hybridization conditions to a nucleic acid molecule comprising the nucleotide sequence of SEQ ID NO:1, 3, 4, or 6.

The nucleotide sequence of the isolated human BAL cDNA and the predicted amino acid sequence of the human BAL polypeptide are shown in FIG. 1 and in SEQ ID NOs:1 and 2, respectively.

The human BAL gene, which is approximately 3244 nucleotides in length, encodes a protein having a molecular weight of approximately 95 kD and which is approximately 826 amino acid residues in length. On a multiple tissue northern blot, BAL transcripts were most abundant in lymphoid organs (spleen, lymph node, fetal liver, and peripheral blood) and several additional non-hematopoietic organs (heart, skeletal muscle and colon).

The nucleotide sequence of the isolated murine BAL cDNA and the predicted amino acid sequence of the murine polypeptide are shown in FIG. 2 and in SEQ ID NOs:4 and 5, respectively.

The murine BAL gene, which is approximately 3024 nucleotides in length, encodes a protein having a molecular weight of approximately 95 kD and which is approximately 826 amino acid residues in length.

Various aspects of the invention are described in further detail in the following subsections:

I. Isolated Nucleic Acid Molecules

One aspect of the invention pertains to isolated nucleic acid molecules that encode BAL proteins or biologically active portions thereof, as well as nucleic acid fragments sufficient for use as hybridization probes to identify BAL-encoding nucleic acid molecules (e.g., BAL mRNA) and fragments for use as PCR primers for the amplification or mutation of BAL nucleic acid molecules. As used herein, the term "nucleic acid molecule" is intended to include DNA molecules (e.g., cDNA or genomic DNA) and RNA molecules (e.g., mRNA) and analogs of the DNA or RNA generated using nucleotide analogs. The nucleic acid molecule can be single-stranded or double-stranded, but preferably is double-stranded DNA.

The term "isolated nucleic acid molecule" includes nucleic acid molecules which are separated from other nucleic acid molecules which are present in the natural source of the nucleic acid. For example, with regards to genomic DNA, the term "isolated" includes nucleic acid molecules which are separated from the chromosome with which the genomic DNA is naturally associated. Preferably, an "isolated" nucleic acid is free of sequences which naturally flank the nucleic acid (i.e., sequences located at the 5' and 3' ends of the nucleic acid) in the genomic DNA of the organism from which the nucleic acid is derived. For example, in various embodiments, the isolated BAL nucleic acid molecule can contain less than about 5 kb, 4 kb, 3 kb, 2 kb, 1 kb, 0.5 kb or 0.1 kb of nucleotide sequences which naturally flank the nucleic acid molecule in genomic DNA of the cell from which the nucleic acid is derived. Moreover, an "isolated" nucleic acid molecule, such as a cDNA molecule, can be substantially free of other cellular material, or culture medium when produced by recombinant techniques, or substantially free of chemical precursors or other chemicals when chemically synthesized.

A nucleic acid molecule of the present invention, e.g., a nucleic acid molecule having the nucleotide sequence of SEQ ID NO:1, 3, 4, or 6 or a portion thereof, can be isolated using standard molecular biology techniques and the sequence information provided herein. Using all or portion of the nucleic acid sequence of SEQ ID NO:1, 3, 4, or 6, as a hybridization probe, BAL nucleic acid molecules can be isolated using standard hybridization and cloning techniques (e.g., as described in Sambrook, J., Fritsh, E. F., and Maniatis, T. *Molecular Cloning: A Laboratory Manual. 2nd, ed., Cold Spring Harbor Laboratory*, Cold Spring Harbor Laboratory Press, Cold Spring Harbor, N.Y., 1989).

Moreover, a nucleic acid molecule encompassing all or a portion of SEQ ID NO:1, 3, 4, or 6 can be isolated by the polymerase chain reaction (PCR) using synthetic oligonucleotide primers designed based upon the sequence of SEQ ID NO:1, 3, 4, or 6.

A nucleic acid of the invention can be amplified using cDNA, mRNA or alternatively, genomic DNA, as a template and appropriate oligonucleotide primers according to standard PCR amplification techniques. The nucleic acid so amplified can be cloned into an appropriate vector and characterized by DNA sequence analysis. Furthermore, oligonucleotides corresponding to BAL nucleotide sequences can be prepared by standard synthetic techniques, e.g., using an automated DNA synthesizer.

In a preferred embodiment, an isolated nucleic acid molecule of the invention comprises the nucleotide sequence shown in SEQ ID NO:1. The sequence of SEQ ID NO:1 corresponds to the human BAL cDNA. This cDNA comprises sequences encoding the human BAL protein (i.e., "the coding region", from nucleotides 229-2790), as well as 5' untranslated sequences (nucleotides 1-228) and 3' untranslated sequences (nucleotides 2791-3243). Alternatively, the nucleic acid molecule can comprise only the coding region of SEQ ID NO:1 (e.g., nucleotides 229-2790, corresponding to SEQ ID NO:3).

In a preferred embodiment, an isolated nucleic acid molecule of the invention comprises the nucleotide sequence shown in SEQ ID NO:4. The sequence of SEQ ID NO:4 corresponds to the murine BAL cDNA. This cDNA comprises sequences encoding the murine BAL protein (i.e., "the coding region", from nucleotides 171-2648), as well as 5' untranslated sequences (nucleotides 1-170) and 3' untranslated sequences (nucleotides 2649-3024). Alternatively, the nucleic acid molecule can comprise only the coding region of SEQ ID NO:4 (e.g., nucleotides 171-2648, corresponding to SEQ ID NO:6).

In another preferred embodiment, an isolated nucleic acid molecule of the invention comprises a nucleic acid molecule which is a complement of the nucleotide sequence shown in SEQ ID NO:1, 3, 4, or 6, or a portion of any of these nucleotide sequences. A nucleic acid molecule which is complementary to the nucleotide sequence shown in SEQ ID NO:1, 3, 4, or 6, is one which is sufficiently complementary to the nucleotide sequence shown in SEQ ID NO:1, 3, 4, or 6, such that it can hybridize to the nucleotide sequence shown in SEQ ID NO:1, 3, 4, or 6.

In still another preferred embodiment, an isolated nucleic acid molecule of the present invention comprises a nucleotide sequence which is at least about 50%, 55%, 60%, 65%, 70%, 72%, 75%, 80%, 85%, 90%, 95%, 98% or more homologous to the entire length of the nucleotide sequence shown in SEQ ID NO:1, 3, 4, or 6 or a portion of any of these nucleotide sequences.

Moreover, the nucleic acid molecule of the invention can comprise only a portion of the nucleic acid sequence of SEQ ID NO:1, 3, 4, or 6, for example, a fragment which can be used as a probe or primer or a fragment encoding a portion of a BAL protein, e.g., a biologically active portion of a BAL protein. The nucleotide sequence determined from the cloning of the BAL gene allows for the generation of probes and primers designed for use in identifying and/or cloning other BAL family members, as well as BAL homologues from other species. The probe/primer typically comprises substantially purified oligonucleotide. The oligonucleotide typically comprises a region of nucleotide sequence that hybridizes under stringent conditions to at least about 12 or 15, preferably about 20 or 25, more preferably about 30, 35, 40, 45, 50, 55, 60, 65, or 75 consecutive nucleotides of a sense sequence of SEQ ID NO:1, 3, 4, or 6, of an anti-sense sequence of SEQ ID NO:1, 3, 4, or 6, or of a naturally occurring allelic variant or mutant of SEQ ID NO:1, 3, 4, or 6. In an exemplary embodiment, a nucleic acid molecule of the present invention comprises a nucleotide sequence which is greater than 300-350, 350-400, 400-450, 452, 452-500, 500-550, 550-600, 607, 607-650, 650-700, 700-750, 750-800, 800-850, 850-900, 900-950, 950-1000, or more nucleotides in length and hybridizes under stringent hybridization conditions to a nucleic acid molecule of SEQ ID NO:1, 3, 4, or 6.

Probes based on the BAL nucleotide sequences can be used to detect transcripts or genomic sequences encoding the same or homologous proteins. In preferred embodiments, the probe farther comprises a label group attached thereto, e.g., the label group can be a radioisotope, a fluorescent compound, an enzyme, or an enzyme co-factor. Such probes can be used as a part of a diagnostic test kit for identifying cells or tissue which misexpress a BAL protein, such as by measuring a level of a BAL-encoding nucleic acid in a sample of cells from a subject e.g., detecting BAL mRNA levels or determining whether a genomic BAL gene has been mutated or deleted.

A nucleic acid fragment encoding a "biologically active portion of a BAL protein" can be prepared by isolating a portion of the nucleotide sequence of SEQ ID NO:1, 3, 4, or 6, which encodes a polypeptide having a BAL biological activity (the biological activities of the BAL proteins are described herein), expressing the encoded portion of the BAL protein (e.g., by recombinant expression in vitro) and assessing the activity of the encoded portion of the BAL protein.

The invention further encompasses nucleic acid molecules that differ from the nucleotide sequence shown in SEQ ID NO:1, 3, 4, or 6, due to degeneracy of the genetic code and thus encode the same BAL proteins as those encoded by the nucleotide sequence shown in SEQ ID NO:1, 3, 4, or 6. In another embodiment, an isolated nucleic acid molecule of the invention has a nucleotide sequence encoding a protein having an amino acid sequence shown in SEQ ID NO:2 or 5.

In addition to the BAL nucleotide sequences shown in SEQ ID NO:1, 3, 4, or 6, it will be appreciated by those skilled in the art that DNA sequence polymorphisms that lead to changes in the amino acid sequences of the BAL proteins may exist within a population (e.g., the human population). Such genetic polymorphism in the BAL genes may exist among individuals within a population due to natural allelic variation. As used herein, the terms "gene" and "recombinant gene" refer to nucleic acid molecules which include an open reading frame encoding a BAL protein, preferably a mammalian BAL protein, and can further include non-coding regulatory sequences, and introns.

Allelic variants of human BAL include both functional and non-functional BAL proteins. Functional allelic variants are naturally occurring amino acid sequence variants of the human BAL protein that maintain the ability to bind a BAL ligand and/or modulate the occurrence or severity of a malignancy such as a lymphoma, e.g., non-Hodgkin's lymphoma. Functional allelic variants will typically contain only conservative substitution of one or more amino acids of SEQ ID NO:2 or 5 or substitution, deletion or insertion of non-critical residues in non-critical regions of the protein.

Non-functional allelic variants are naturally occurring amino acid sequence variants of the human BAL protein that do not have the ability to either bind a BAL ligand and/or modulate occurrence or severity of a malignancy such as a lymphoma, e.g., non-Hodgkin's lymphoma. Non-functional allelic variants will typically contain a non-conservative substitution, a deletion, or insertion or premature truncation of the amino acid sequence of SEQ ID NO:2 or 5 or a substitution, insertion or deletion in critical residues or critical regions.

The present invention further provides non-human orthologues of the human BAL protein. Orthologues of the human BAL protein are proteins that are isolated from non-human organisms and possess the same BAL ligand binding and/or modulation of the occurrence or severity of a malignancy such as a lymphoma, e.g., non-Hodgkin's lymphoma capabilities of the human BAL protein. Orthologues of the human BAL protein can readily be identified as comprising an amino acid sequence that is substantially homologous to SEQ ID NO:2 or 5.

Moreover, nucleic acid molecules encoding other BAL family members and, thus, which have a nucleotide sequence which differs from the BAL sequences of SEQ ID NO:1, 3, 4, or 6 are intended to be within the scope of the invention. For example, another BAL cDNA can be identified based on the nucleotide sequence of human BAL. Moreover, nucleic acid molecules encoding BAL proteins from different species, and which, thus, have a nucleotide sequence which differs from the BAL sequences of SEQ ID NO:1, 3, 4, or 6 are intended to be within the scope of the invention. For example, a monkey BAL cDNA can be identified based on the nucleotide sequence of a human or murine BAL.

Nucleic acid molecules corresponding to natural allelic variants and homologues of the BAL cDNAs of the invention can be isolated based on their homology to the BAL nucleic acids disclosed herein using the cDNAs disclosed herein, or a portion thereof, as a hybridization probe according to standard hybridization techniques under stringent hybridization conditions. Nucleic acid molecules corresponding to natural allelic variants and homologues of the BAL cDNAs of the invention can further be isolated by mapping to the same chromosome or locus as the BAL gene.

Accordingly, in another embodiment, an isolated nucleic acid molecule of the invention is at least 15, 20, 25, 30 or more nucleotides in length and hybridizes under stringent conditions to the nucleic acid molecule comprising the nucleotide sequence of SEQ ID NO:1, 3,4, or 6. In other embodiment, the nucleic acid is at least 30, 50, 100, 150, 200, 250, 300, 350, 400, 450, 452, 500, 550, 607, 600, 650, 700, 750, 800, 850, 900, or 950 nucleotides in length. As used herein, the term "hybridizes under stringent conditions" is intended to describe conditions for hybridization and washing under which nucleotide sequences at least 60% homologous to each other typically remain hybridized to each other. Preferably, the conditions are such that sequences at least about 70%, more preferably at least about 80%, even more preferably at least about 85% or 90% homologous to each other typically remain hybridized to each other. Such stringent conditions are known to those skilled in the art and can be found in *Current Protocols in Molecular Biology*, John Wiley & Sons, N.Y. (1989), 6.3.1-6.3.6. A preferred, non-limiting example of stringent hybridization conditions are hybridization in 6× sodium chloride/sodium citrate (SSC) at about 45° C., followed by one or more washes in 0.2×SSC, 0.1 % SDS at 50° C., preferably at 55° C., more preferably at 60° C., and even more preferably at 65° C. Preferably, an isolated nucleic acid molecule of the invention that hybridizes under stringent conditions to the sequence of SEQ ID NO:1, 3, 4, or 6 corresponds to a naturally-occurring nucleic acid molecule. As used herein, a "naturally-occurring" nucleic acid molecule refers to an RNA or DNA molecule having a nucleotide sequence that occurs in nature (e.g., encodes a natural protein).

In addition to naturally-occurring allelic variants of the BAL sequences that may exist in the population, the skilled artisan will further appreciate that changes can be introduced by mutation into the nucleotide sequences of SEQ ID NO:1, 3, 4, or 6 thereby leading to changes in the amino acid sequence of the encoded BAL proteins, without altering the functional ability of the BAL proteins. For example, nucleotide substitutions leading to amino acid substitutions at "non-essential" amino acid residues can be made in the sequence of SEQ ID NO:1, 3, 4, or 6. A "non-essential" amino acid residue is a residue that can be altered from the wild-type sequence of BAL (e.g., the sequence of SEQ ID NO:2 or 5) without altering the biological activity, whereas an "essential" amino acid residue is required for biological activity. For example, amino acid residues that are conserved among the BAL proteins of the present invention, are predicted to be particularly unamenable to alteration. Furthermore, additional amino acid residues that are conserved between the BAL proteins of the present invention and other members of the BAL family are not likely to be amenable to alteration.

Accordingly, another aspect of the invention pertains to nucleic acid molecules encoding BAL proteins that contain changes in amino acid residues that are not essential for activity. Such BAL proteins differ in amino acid sequence from SEQ ID NO:2 or 5, yet retain biological activity. In one embodiment, the isolated nucleic acid molecule comprises a nucleotide sequence encoding a protein, wherein the protein comprises an amino acid sequence at least about 50%, 55%, 60%, 62%, 65%, 70%, 75%, 80%, 85%, 90%, 95%, 98% or more homologous to SEQ ID NO:2 or 5.

An isolated nucleic acid molecule encoding a BAL protein homologous to the protein of SEQ ID NO:2 or 5 can be created by introducing one or more nucleotide substitutions, additions or deletions into the nucleotide sequence of SEQ ID NO:1, 3, 4, or 6, such that one or more amino acid substitutions, additions or deletions are introduced into the encoded protein. Mutations can be introduced intd SEQ ID NO:1, 3, 4, or 6, by standard techniques, such as site-directed mutagenesis and PCR-mediated mutagenesis. Preferably, conservative amino acid substitutions are made at one or more predicted non-essential amino acid residues. A "conservative amino acid substitution" is one in which the amino acid residue is replaced with an amino acid residue having a similar side chain. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a BAL protein is preferably replaced with another amino acid residue from the same side chain family. Alternatively, in another embodiment, mutations can be introduced randomly along all or part of a BAL coding sequence, such as by saturation mutagenesis, and the resultant mutants can be screened for BAL biological activity to identify mutants that retain activity. Following mutagenesis of SEQ ID NO:1, 3, 4, or 6, the encoded protein can be expressed recombinantly and the activity of the protein can be determined.

In a preferred embodiment, a mutant BAL protein can be assayed for the ability to (1) interact with a non-BAL protein molecule, e.g., CRK, CRK-L, SHP-2, PBK, or ZAP70; (2) activate a BAL-dependent signal transduction pathway; or (3) modulate the occurrence or severity of a lymphoma, e.g., non Hodgkin's lymphoma.

In addition to the nucleic acid molecules encoding BAL proteins described above, another aspect of the invention pertains to isolated nucleic acid molecules which are antisense thereto. An "antisense" nucleic acid comprises a nucleotide sequence which is complementary to a "sense" nucleic acid encoding a protein, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire BAL coding strand, or to only a portion thereof. In one embodiment, an antisense nucleic acid molecule is antisense to a "coding region" of the coding strand of a nucleotide sequence encoding BAL. The term "coding region" refers to the region of the nucleotide sequence comprising codons which are translated into amino acid residues (e.g., the coding region of human and murine BAL corresponds to SEQ ID NO:3 and 6, respectively). In another embodiment, the antisense nucleic acid molecule is antisense to a "noncoding region" of the coding strand of a nucleotide sequence encoding BAL. The term "noncoding region" refers to 5' and 3' sequences which flank the coding region that are not translated into amino acids (i.e., also referred to as 5' and 3' untranslated regions).

Given the coding strand sequences encoding BAL disclosed herein (e.g., SEQ ID NO:3 and 6), antisense nucleic acids of the invention can be designed according to the rules of Watson and Crick base pairing. The antisense nucleic acid molecule can be complementary to the entire coding region of BAL mRNA, but more preferably is an oligonucleotide which is antisense to only a portion of the coding or noncoding region of BAL mRNA. For example, the antisense oligonucleotide can be complementary to the region surrounding the translation start site of BAL mRNA. An antisense oligonucleotide can be, for example, about 5, 10, 15, 20, 25, 30, 35, 40, 45 or 50 nucleotides in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xantine. 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection).

The antisense nucleic acid molecules of the invention are typically administered to a subject or generated in situ such that they hybridize with or bind to cellular mRNA and/or genomic DNA encoding a BAL protein to thereby inhibit expression of the protein, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention include direct injection at a tissue site. Alternatively, antisense nucleic acid molecules can be modified to target selected cells and then administered systemically. For example, for systemic administration, antisense molecules can be modified such that they specifically bind to receptors or antigens expressed on a selected cell surface, e.g., by linking the antisense nucleic acid molecules to peptides or antibodies which bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are preferred.

In yet another embodiment, the antisense nucleic acid molecule of the invention is an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-o-methylribonucleotide (Inoue et al. (1987) *Nucleic Acids Res.* 15:6131-6148) or a chimeric RNA-DNA analogue (Inoue et al. (1987) *FEBS Lett.* 215:327-330).

In still another embodiment, an antisense nucleic acid of the invention is a ribozyme. Ribozymes are catalytic RNA molecules with ribonuclease activity which are capable of cleaving a single-stranded nucleic acid, such as an mRNA, to which they have a complementary region. Thus, ribozymes (e.g., hammerhead ribozymes (described in Haselhoff and Gerlach (1988) *Nature* 334:585-591)) can be used to catalytically cleave BAL mRNA transcripts to thereby inhibit translation of BAL mRNA. A ribozyme having specificity for a BAL-encoding nucleic acid can be designed based upon the nucleotide sequence of a BAL cDNA disclosed herein (i.e., SEQ ID NO:1, 3, 4, or 6). For example, a derivative of a *Tetrahymena* L-19 IVS RNA can be constructed in which the nucleotide sequence of the active site is complementary to the nucleotide sequence to be cleaved in a BAL-encoding mRNA. See, e.g., Cech et al. U.S. Pat. No. 4,987,071; and Cech et al. U.S. Pat. No. 5,116,742. Alternatively, BAL mRNA can be used to select a catalytic RNA having a specific ribonuclease activity from a pool of RNA molecules. See, e.g., Bartel, D. and Szostak, J. W. (1993) *Science* 261:1411-1418.

Alternatively, BAL gene expression can be inhibited by targeting nucleotide sequences complementary to the regulatory region of the BAL (e.g., the BAL promoter and/or enhancers) to form triple helical structures that prevent transcription of the BAL gene in target cells. See generally, Helene, C. (1991) *Anticancer Drug Des.* 6(6):569-84; Helene, C. et al. (1992) *Ann. N.Y. Acad. Sci.* 660:27-36; and Maher, L. J. (1992) *Bioassays* 14(12):807-15.

In yet another embodiment, the BAL nucleic acid molecules of the present invention can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup B. et al. (1996) *Bioorganic & Medicinal Chemistry* 4 (1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup B. et al. (1996) supra; Perry-O'Keefe et al. *Proc. Natl. Acad. Sci.* 93: 14670-675.

PNAs of BAL nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of BAL nucleic acid molecules can also be used in the analysis of single base pair mutations in a gene, (e.g., by PNA-directed PCR clamping); as 'artificial restriction enzymes' when used in combination with other enzymes, (e.g., S1 nucleases (Hyrup B. (1996) supra)); or as probes or primers for DNA sequencing or hybridization (Hyrup B. et al. (1996) supra; Perry-O'Keefe supra).

In another embodiment, PNAs of BAL can be modified, (e.g., to enhance their stability or cellular uptake), by attaching lipophilic or other helper groups to PNA, by the formation of PNA-DNA chimeras, or by the use of liposomes or other techniques of drug delivery known in the art. For example, PNA-DNA chimeras of BAL nucleic acid molecules can be generated which may combine the advantageous properties of PNA and DNA. Such chimeras allow DNA recognition enzymes, (e.g., RNAse H and DNA polymerases), to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup B. (1996) supra). The synthesis of PNA-DNA chimeras can be performed as described in Hyrup B. (1996) supra and Finn P. J. et al. (1996) *Nucleic Acids Res.* 24 (17): 3357-63. For example, a DNA chain can be synthesized on a solid support using standard phosphoramidite coupling chemistry and modified nucleoside analogs, e.g., 5'-(4-methoxytrityl)amino-5'-deoxy-thymidine phosphoramidite, can be used as a between the PNA and the 5' end of DNA (Mag, M. et al. (1989) *Nucleic Acid Res.* 17: 5973-88). PNA monomers are then coupled in a stepwise manner to produce a chimeric molecule with a 5' PNA segment and a 3' DNA segment (Finn P. J. et al. (1996) supra). Alternatively, chimeric molecules can be synthesized with a 5' DNA segment and a 3' PNA segment (Peterser, K. H. et al. (1975) *Bioorganic Med. Chem. Lett.* 5: 1119-11124).

In other embodiments, the oligonucleotide may include other appended groups such as peptides (e.g., for targeting host cell receptors in vivo), or agents facilitating transport across the cell membrane (see, e.g., Letsinger et al. (1989) *Proc. Natl. Acad. Sci. USA* 86:6553-6556; Lemaitre et al. (1987) *Proc. Natl. Acad. Sci. USA* 84:648-652; PCT Publication No. WO88/09810) or the blood-brain barrier (see, e.g., PCT Publication No. WO89/10134). In addition, oligonucleotides can be modified with hybridization-triggered cleavage agents (See, e.g., Krol et al. (1988) *Bio-Techniques* 6:958-976) or intercalating agents. (See, e.g., Zon (1988) *Pharm. Res.* 5:539-549). To this end, the oligonucleotide may be conjugated to another molecule, (e.g., a peptide, hybridization triggered cross-linking agent, transport agent, or hybridization-triggered cleavage agent).

II. Isolated BAL Proteins and Anti-BAL Antibodies

One aspect of the invention pertains to isolated BAL proteins, and biologically active portions thereof, as well as polypeptide fragments suitable for use as immunogens to raise anti-BAL antibodies. In one embodiment, native BAL proteins can be isolated from cells or tissue sources by an appropriate purification scheme using standard protein purification techniques. In another embodiment, BAL proteins are produced by recombinant DNA techniques. Alternative to recombinant expression, a BAL protein or polypeptide can be synthesized chemically using standard peptide synthesis techniques.

An "isolated" or "purified" protein or biologically active portion thereof is substantially free of cellular material or other contaminating proteins from the cell or tissue source from which the BAL protein is derived, or substantially free from chemical precursors or other chemicals when chemically synthesized. The language "substantially free of cellular material" includes preparations of BAL protein in which the protein is separated from cellular components of the cells from which it is isolated or recombinantly produced. In one embodiment, the language "substantially free of cellular material" includes preparations of BAL protein having less than about 30% (by dry weight) of non-BAL protein (also referred to herein as a "contaminating protein"), more preferably less than about 20% of non-BAL protein, still more preferably less than about 10% of non-BAL protein, and most preferably less than about 5% non-BAL protein. When the BAL protein or biologically active portion thereof is recombinantly produced, it is also preferably substantially free of culture medium, i.e., culture medium represents less than about 20%, more preferably less than about 10%, and most preferably less than about 5% of the volume of the protein preparation.

The language "substantially free of chemical precursors or other chemicals" includes preparations of BAL protein in which the protein is separated from chemical precursors or other chemicals which are involved in the synthesis of the protein. In one embodiment, the language "substantially free of chemical precursors or other chemicals" includes preparations of BAL protein having less than about 30% (by dry weight) of chemical precursors or non-BAL chemicals, more preferably less than about 20% chemical precursors or non-BAL chemicals, still more preferably less than about 10% chemical precursors or non-BAL chemicals, and most preferably less than about 5% chemical precursors or non-BAL chemicals.

As used herein, a "biologically active portion" of a BAL protein includes a fragment of a BAL protein which participates in an interaction between a BAL molecule and a non-BAL molecule. Biologically active portions of a BAL protein include peptides comprising amino acid sequences sufficiently homologous to or derived from the amino acid sequence of the BAL protein, e.g., the amino acid sequence shown in SEQ ID NO:2 or 5, which include less amino acids than the full length BAL proteins, and exhibit at least one activity of a BAL protein. Typically, biologically active portions comprise a domain or motif with at least one activity of the BAL protein, e.g., modulating cellular adhesion. A biologically active portion of a BAL protein can be a polypeptide which is, for example, 10, 25, 50, 100, 200 or more amino acids in length. Biologically active portions of a BAL protein can be used as targets for developing agents which modulate a BAL mediated activity, e.g., the occurrence or severity of a lymphoma, e.g., non-Hodgkin's lymphoma.

In one embodiment, a biologically active portion of a BAL protein comprises at least one proline rich domain and/or at least one tyrosine phosphorylation site. It is to be understood that a preferred biologically active portion of a BAL protein of the present invention may contain at least one of the above-identified structural domains. A more preferred biologically active portion of a BAL protein may contain at least two of the above-identified structural domains. Moreover, other biologically active portions, in which other regions of the protein are deleted, can be prepared by recombinant techniques and evaluated for one or more of the functional activities of a native BAL protein.

In a preferred embodiment, the BAL protein has an amino acid sequence shown in SEQ ID NO:2 or 5. In other embodiments, the BAL protein is substantially homologous to SEQ ID NO:2 or 5, and retains the functional activity of the protein of SEQ ID NO:2 or 5, yet differs in amino acid sequence due to natural allelic variation or mutagenesis, as described in detail in subsection I above. Accordingly, in another embodiment, the BAL protein is a protein which comprises an amino acid sequence at least about 50%, 55%, 60%, 62%, 65%, 70%, 75%, 80%, 85%, 90%, 95%, 98% or more homologous to SEQ ID NO:2 or 5.

To determine the percent identity of two amino acid sequences or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, the length of a reference sequence aligned for comparison purposes is at least 30%, preferably at least 40%, more preferably at least 50%, even more preferably at least 60%, and even more preferably at least 70%, 80%, or 90% of the length of the reference sequence (e.g., when aligning a second sequence to the BAL amino acid sequence of SEQ ID NO:2 or 5 having 177 amino acid residues, at least 80, preferably at least 100, more preferably at least 120, even more preferably at least 140, and even more preferably at least 150, 160 or 170 amino acid residues are aligned). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity between two sequences can be accomplished using a mathematical algorithm. In a preferred embodiment, the percent identity between two amino acid sequences is determined using the Needleman and Wunsch (*J. Mol. Biol.* (48): 444-453 (1970)) algorithm which has been incorporated into the GAP program in the GCG software package (available at http://www.gcg.com), using either a Blosum 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (available at http://www.gcg.com), using a NWSgapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Meyers and W. Miller (CABIOS, 4:11-17

(1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against public databases to, for example, identify other family members or related sequences. Such searches can be performed using the NBLAST and XBLAST programs (version 2.0) of Altschul, et al. (1990) *J. Mol. Biol.* 215:403-10. BLAST nucleotide searches can be performed with the NBLAST program, score=100, wordlength=12 to obtain nucleotide sequences homologous to BAL nucleic acid molecules of the invention. BLAST protein searches can be performed with the XBLAST program, score=50, wordlength=3 to obtain amino acid sequences homologous to BAL protein molecules of the invention. To obtain gapped alignments for comparison purposes, Gapped BLAST can be utilized as described in Altschul et al., (1997) *Nucleic Acids Res.* 25(17):3389-3402. When utilizing BLAST and Gapped BLAST programs, the default parameters of the respective programs (e.g., XBLAST and NBLAST) can be used. See http://www.ncbi.nlm.nih.gov.

The invention also provides BAL chimeric or fusion proteins. As used herein, a BAL "chimeric protein" or "fusion protein" comprises a BAL polypeptide operatively linked to a non-BAL polypeptide. An "BAL polypeptide" refers to a polypeptide having an amino acid sequence corresponding to BAL, whereas a "non-BAL polypeptide" refers to a polypeptide having an amino acid sequence corresponding to a protein which is not substantially homologous to the BAL protein, e.g., a protein which is different from the BAL protein and which is derived from the same or a different organism. Within a BAL fusion protein the BAL polypeptide can correspond to all or a portion of a BAL protein. In a preferred embodiment, a BAL fusion protein comprises at least one biologically active portion of a BAL protein. In another preferred embodiment, a BAL fusion protein comprises at least two biologically active portions of a BAL protein. Within the fusion protein, the term "operatively linked" is intended to indicate that the BAL polypeptide and the non-BAL polypeptide are fused in-frame to each other. The non-BAL polypeptide can be fused to the N-terminus or C-terminus of the BAL polypeptide.

For example, in one embodiment, the fusion protein is a GST-BAL fusion protein in which the BAL sequences are fused to the C-terminus of the GST sequences. Such fusion proteins can facilitate the purification of recombinant BAL.

In another embodiment, the fusion protein is a BAL protein containing a heterologous signal sequence at its N-terminus. In certain host cells (e.g., mammalian host cells), expression and/or secretion of BAL can be increased through use of a heterologous signal sequence.

The BAL fusion proteins of the invention can be incorporated into pharmaceutical compositions and administered to a subject in vivo. The BAL fusion proteins can be used to affect the bioavailability of a BAL substrate. Use of BAL fusion proteins may be useful therapeutically for the treatment of disorders caused by, for example, (i) aberrant modification or mutation of a gene encoding a BAL protein; (ii) mis-regulation of the BAL gene; and (iii) aberrant post-translational modification of a BAL protein.

Moreover, the BAL-fusion proteins of the invention can be used as immunogens to produce anti-BAL antibodies in a subject, to purify BAL ligands and in screening assays to identify molecules which inhibit the interaction of BAL with a BAL substrate.

Preferably, a BAL chimeric or fusion protein of the invention is produced by standard recombinant DNA techniques. For example, DNA fragments coding for the different polypeptide sequences are ligated together in-frame in accordance with conventional techniques, for example by employing blunt-ended or stagger-ended termini for ligation, restriction enzyme digestion to provide for appropriate termini, filling-in of cohesive ends as appropriate, alkaline phosphatase treatment to avoid undesirable joining, and enzymatic ligation. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and reamplified to generate a chimeric gene sequence (see, for example, *Current Protocols in Molecular Biology*, eds. Ausubel et al. John Wiley & Sons: 1992). Moreover, many expression vectors are commercially available that already encode a fusion moiety (e.g., a GST polypeptide). An BAL-encoding nucleic acid can be cloned into such an expression vector such that the fusion moiety is linked in-frame to the BAL protein.

The present invention also pertains to variants of the BAL proteins which function as either BAL agonists (mimetics) or as BAL antagonists. Variants of the BAL proteins can be generated by mutagenesis, e.g., discrete point mutation or truncation of a BAL protein. An agonist of the BAL proteins can retain substantially the same, or a subset, of the biological activities of the naturally occurring form of a BAL protein. An antagonist of a BAL protein can inhibit one or more of the activities of the naturally occurring form of the BAL protein by, for example, competitively modulating a BAL-mediated activity of a BAL protein. Thus, specific biological effects can be elicited by treatment with a variant of limited function. In one embodiment, treatment of a subject with a variant having a subset of the biological activities of the naturally occurring form of the protein has fewer side effects in a subject relative to treatment with the naturally occurring form of the BAL protein.

In one embodiment, variants of a BAL protein which function as either BAL agonists (mimetics) or as BAL antagonists can be identified by screening combinatorial libraries of mutants, e.g., truncation mutants, of a BAL protein for BAL protein agonist or antagonist activity. In one embodiment, a variegated library of BAL variants is generated by combinatorial mutagenesis at the nucleic acid level and is encoded by a variegated gene library. A variegated library of BAL variants can be produced by, for example, enzymatically ligating a mixture of synthetic oligonucleotides into gene sequences such that a degenerate set of potential BAL sequences is expressible as individual polypeptides, or alternatively, as a set of larger fusion proteins (e.g., for phage display) containing the set of BAL sequences therein. There are a variety of methods which can be used to produce libraries of potential BAL variants from a degenerate oligonucleotide sequence. Chemical synthesis of a degenerate gene sequence can be performed in an automatic DNA synthesizer, and the synthetic gene then ligated into an appropriate expression vector. Use of a degenerate set of genes allows for the provision, in one mixture, of all of the sequences encoding the desired set of potential BAL sequences. Methods for synthesizing degenerate oligonucleotides are known in the art (see, e.g., Narang, S. A. (1983) *Tetrahedron* 39:3; Itakura et al. (1984) *Annu. Rev. Biochem.* 53:323; Itakura et al. (1984) *Science* 198:1056; Ike et al. (1983) *Nucleic Acid Res.* 11:477.

In addition, libraries of fragments of a BAL protein coding sequence can be used to generate a variegated population of BAL fragments for screening and subsequent selection of variants of a BAL protein. In one embodiment, a library of coding sequence fragments can be generated by treating a double stranded PCR fragment of a BAL coding sequence with a nuclease under conditions wherein nicking occurs only about once per molecule, denaturing the double stranded DNA, renaturing the DNA to form double stranded DNA which can include sense/antisense pairs from different nicked products, removing single stranded portions from reformed duplexes by treatment with SI nuclease, and ligating the resulting fragment library into an expression vector. By this method, an expression library can be derived which encodes N-terminal, C-terminal and internal fragments of various sizes of the BAL protein.

Several techniques are known in the art for screening gene products of combinatorial libraries made by point mutations or truncation, and for screening cDNA libraries for gene products having a selected property. Such techniques are adaptable for rapid screening of the gene libraries generated by the combinatorial mutagenesis of BAL proteins. The most widely used techniques, which are amenable to high throughput analysis, for screening large gene libraries typically include cloning the gene library into replicable expression vectors, transforming appropriate cells with the resulting library of vectors, and expressing the combinatorial genes under conditions in which detection of a desired activity facilitates isolation of the vector encoding the gene whose product was detected. Recrusive ensemble mutagenesis (REM), a new technique which enhances the frequency of functional mutants in the libraries, can be used in combination with the screening assays to identify BAL variants (Arkin and Yourvan (1992) *Proc. Natl. Acad Sci. USA* 89:7811-7815; Delgrave et al. (1993) *Protein Engineering* 6(3):327-331).

In one embodiment, cell based assays can be exploited to analyze a variegated BAL library. For example, a library of expression vectors can be transfected into a cell line which ordinarily responds to a particular ligand in a BAL-dependent manner. The transfected cells are then contacted with the ligand and the effect of expression of the mutant on signaling by the ligand can be detected, e.g., by measuring cell survival or the activity of a BAL-regulated transcription factor. Plasmid DNA can then be recovered from the cells which score for inhibition, or alternatively, potentiation of signaling by the ligand, and the individual clones further characterized.

An isolated BAL protein, or a portion or fragment thereof, can be used as an immunogen to generate antibodies that bind BAL using standard techniques for polyclonal and monoclonal antibody preparation. A full-length BAL protein can be used or, alternatively, the invention provides antigenic peptide fragments of BAL for use as immunogens. The antigenic peptide of BAL comprises at least 8 amino acid residues of the amino acid sequence shown in SEQ ID NO:2 or 5 and encompasses an epitope of BAL such that an antibody raised against the peptide forms a specific immune complex with BAL. Preferably, the antigenic peptide comprises at least 10 amino acid residues, more preferably at least 15 amino acid residues, even more preferably at least 20 amino acid residues, and most preferably at least 30 amino acid residues.

Preferred epitopes encompassed by the antigenic peptide are regions of BAL that are located on the surface of the protein, e.g., hydrophilic regions, as well as regions with high antigenicity.

A BAL immunogen typically is used to prepare antibodies by immunizing a suitable subject, (e.g., rabbit, goat, mouse or other mammal) with the immunogen. An appropriate immunogenic preparation can contain, for example, recombinantly expressed BAL protein or a chemically synthesized BAL polypeptide. The preparation can further include an adjuvant, such as Freund's complete or incomplete adjuvant, or similar immunostimulatory agent. Immunization of a suitable subject with an immunogenic BAL preparation induces a polyclonal anti-BAL antibody response.

Accordingly, another aspect of the invention pertains to anti-BAL antibodies. The term "antibody" as used herein refers to immunoglobulin molecules and immunologically active portions of immunoglobulin molecules, i.e., molecules that contain an antigen binding site which specifically binds (immunoreacts with) an antigen, such as BAL. Examples of immunologically active portions of immunoglobulin molecules include F(ab) and F(ab')$_2$ fragments which can be generated by treating the antibody with an enzyme such as pepsin. The invention provides polyclonal and monoclonal antibodies that bind BAL. The term "monoclonal antibody" or "monoclonal antibody composition", as used herein, refers to a population of antibody molecules that contain only one species of an antigen binding site capable of immunoreacting with a particular epitope of BAL. A monoclonal antibody composition thus typically displays a single binding affinity for a particular BAL protein with which it immunoreacts.

Polyclonal anti-BAL antibodies can be prepared as described above by immunizing a suitable subject with a BAL immunogen. The anti-BAL antibody titer in the immunized subject can be monitored over time by standard techniques, such as with an enzyme linked immunosorbent assay (ELISA) using immobilized BAL. If desired, the antibody molecules directed against BAL can be isolated from the mammal (e.g., from the blood) and further purified by well known techniques, such as protein A chromatography to obtain the IgG fraction. At an appropriate time after immunization, e.g., when the anti-BAL antibody titers are highest, antibody-producing cells can be obtained from the subject and used to prepare monoclonal antibodies by standard techniques, such as the hybridoma technique originally described by Kohler and Milstein (1975) *Nature* 256:495-497) (see also, Brown et al. (1981) *J. Immunol.* 127:539-46; Brown et al. (1980) *J. Biol. Chem.* 255:4980-83; Yeh et al. (1976) *Proc. Natl. Acad. Sci. USA* 76:2927-31; and Yeh et al. (1982) *Int. J. Cancer* 29:269-75), the more recent human B cell hybridoma technique (Kozbor et al. (1983) *Immunol Today* 4:72), the EBV-hybridoma technique (Cole et al. (1985), *Monoclonal Antibodies and Cancer Therapy*, Alan R. Liss, Inc., pp. 77-96) or trioma techniques. The technology for producing monoclonal antibody hybridomas is well known (see generally R. H. Kenneth, in *Monoclonal Antibodies: A New Dimension In Biological Analyses*, Plenum Publishing Corp., New York, N.Y. (1980); E. A. Lerner (1981) *Yale J. Biol. Med.*, 54:387-402; M. L. Gefter et al. (1977) *Somatic Cell Genet.* 3:231-36). Briefly, an immortal cell line (typically a myeloma) is fused to lymphocytes (typically splenocytes) from a mammal immunized with a BAL immunogen as described above, and the culture supernatants of the resulting hybridoma cells are screened to identify a hybridoma producing a monoclonal antibody that binds BAL.

Any of the many well known protocols used for fusing lymphocytes and immortalized cell lines can be applied for the purpose of generating an anti-BAL monoclonal antibody (see, e.g., G. Galfre et al. (1977) *Nature* 266:55052; Gefter et al. *Somatic Cell Genet.*, cited supra; Lerner, *Yale J. Biol. Med.*, cited supra; Kenneth, *Monoclonal Antibodies*, cited supra). Moreover, the ordinarily skilled worker will appreciate that there are many variations of such methods which also would be useful. Typically, the immortal cell line (e.g., a myeloma cell line) is derived from the same mammalian species as the lymphocytes. For example, murine hybridomas can be made by fusing lymphocytes from a mouse immunized with an immunogenic preparation of the present invention with an immortalized mouse cell line. Preferred immortal cell lines are mouse myeloma cell lines that are sensitive to culture medium containing hypoxanthine, aminopterin and thymidine ("HAT medium"). Any of a number of myeloma cell lines can be used as a fusion partner according to standard techniques, e.g., the P3-NS1/1-Ag4-1, P3-x63-Ag8.653 or Sp2/O-Ag14 myeloma lines. These myeloma lines are available from ATCC. Typically, HAT-sensitive mouse myeloma cells are fused to mouse splenocytes using polyethylene glycol ("PEG"). Hybridoma cells resulting from the fusion are then selected using HAT medium, which kills unfused and unproductively fused myeloma cells (unfused splenocytes die after several days because they are not transformed). Hybridoma cells producing a monoclonal antibody of the invention are detected by screening the hybridoma culture supernatants for antibodies that bind BAL, e.g., using a standard ELISA assay.

Alternative to preparing monoclonal antibody-secreting hybridomas, a monoclonal anti-BAL antibody can be identified and isolated by screening a recombinant combinatorial immunoglobulin library (eg., an antibody phage display library) with BAL to thereby isolate immunoglobulin library members that bind BAL. Kits for generating and screening phage display libraries are commercially available (e.g., the Pharmacia *Recombinant Phage Antibody System*, Catalog No. 27-9400-01; and the Stratagene *SurfZAP™ Phage Display Kit*, Catalog No. 240612). Additionally, examples of methods and reagents particularly amenable for use in generating and screening antibody display library can be found in, for example, Ladner et al. U.S. Pat. No. 5,223,409; Kang et al. PCT International Publication No. WO 92/18619; Dower et al. PCT International Publication No. WO 91/17271; Winter et al. PCT International Publication WO 92/20791; Markland et al. PCT International Publication No. WO 92/15679; Breitling et al. PCT International Publication WO 93/01288; McCafferty et al. PCT International Publication No. WO 92/01047; Garrard et al. PCT International Publication No. WO 92/09690; Ladner et al. PCT International Publication No. WO 90/02809; Fuchs et al. (1991) *Bio/Technology* 9:1370-1372; Hay et al. (1992) *Hum. Antibod. Hybridomas* 3:81-85; Huse et al. (1989) *Science* 246: 1275-1281; Griffiths et al. (1993) *EMBO J* 12:725-734; Hawkins et al. (1992) *J. Mol. Biol.* 226:889-896; Clarkson et al. (1991) *Nature* 352:624-628; Gram el al. (1992) *Proc. Natl. Acad. Sci. USA* 89:3576-3580; Garrad et al. (1991) *Bio/Technology* 9:1373-1377; Hoogenboom et al. (1991) *Nuc. Acid Res.* 19:4133-4137; Barbas et al. (1991) *Proc. Natl. Acad. Sci. USA* 88:7978-7982; and McCafferty et al. *Nature* (1990) 348:552-554.

Additionally, recombinant anti-BAL antibodies, such as chimeric and humanized monoclonal antibodies, comprising both human and non-human portions, which can be made using standard recombinant DNA techniques, are within the scope of the invention. Such chimeric and humanized monoclonal antibodies can be produced by recombinant DNA techniques known in the art, for example using methods described in Robinson et al. International Application No. PCT/US86/02269; Akira, et al. European Patent Application 184,187; Taniguchi, M., European Patent Application 171,496; Morrison el al. European Patent Application 173,494; Neuberger et al. PCT International Publication No. WO 86/01533; Cabilly et al. U.S. Pat. No. 4,816,567; Cabilly et al. European Patent Application 125,023; Better et al. (1988) *Science* 240:1041-1043; Liu et al. (1987) *Proc. Natl. Acad. Sci. USA* 84:3439-3443; Liu et al. (1987) *J. Immunol.* 139:3521-3526; Sun et al. (1987) *Proc. Natl. Acad. Sci. USA* 84:214-218; Nishimura el al. (1987) *Canc. Res.* 47:999-1005; Wood et al. (1985) *Nature* 314:446-449; and Shaw et al. (1988) *J. Natl. Cancer Inst.* 80:1553-1559); Morrison, S. L. (1985) *Science* 229:1202-1207; Oi et al. (1986) *BioTechniques* 4:214; Winter U.S. Pat. No. 5,225,539; Jones et al. (1986) *Nature* 321:552-525; Verhoeyan el al. (1988) *Science* 239:1534; and Beidler et al. (1988) *J. Immunol.* 141:4053-4060.

An anti-BAL antibody (e.g., monoclonal antibody) can be used to isolate BAL by standard techniques, such as affinity chromatography or immunoprecipitation. An anti-BAL antibody can facilitate the purification of natural BAL from cells and of recombinantly produced BAL expressed in host cells. Moreover, an anti-BAL antibody can be used to detect BAL protein (e.g., in a cellular lysate or cell supernatant) in order to evaluate the abundance and pattern of expression of the BAL protein. Anti-BAL antibodies can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, -galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

III. Recombinant Expression Vectors and Host Cells

Another aspect of the invention pertains to vectors, preferably expression vectors, containing a nucleic acid encoding a BAL protein (or a portion thereof). As used herein, the term "vector" refers to a nucleic acid molecule capable of transporting another nucleic acid to which it has been linked. One type of vector is a "plasmid", which refers to a circular double stranded DNA loop into which additional DNA segments can be ligated. Another type of vector is a viral vector, wherein additional DNA segments can be ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Moreover, certain vectors are capable of directing the expression of genes to which they are operatively linked. Such vectors are referred to herein as "expression vectors". In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The recombinant expression vectors of the invention comprise CL nucleic acid of the invention in a form suitable for expression of the nucleic acid in a host cell, which means that the recombinant expression vectors include one or more regulatory sequences, selected on the basis of the host cells to be used for expression, which is operatively linked to the nucleic acid sequence to be expressed. Within a recombinant expression vector, "operably linked" is intended to mean that the nucleotide sequence of interest is linked to the regulatory sequence(s) in a manner which allows for expression of the nucleotide sequence (e.g., in an in vitro transcription/translation system or in a host cell when the vector is introduced into the host cell). The term "regulatory sequence" is intended to include promoters, enhancers and other expression control elements (e.g., polyadenylation signals). Such regulatory sequences are described, for example, in Goeddel; *Gene Expression Technology: Methods in Enzymology* 185, Academic Press, San Diego, Calif. (1990). Regulatory sequences include those which direct constitutive expression of a nucleotide sequence in many types of host cells and those which direct expression of the nucleotide sequence only in certain host cells (e.g., tissue-specific regulatory sequences). It will be appreciated by those skilled in the art that the design of the expression vector can depend on such factors as the choice of the host cell to be transformed, the level of expression of protein desired, and the like. The expression vectors of the invention can be introduced into host cells to thereby produce proteins or peptides, including fusion proteins or peptides, encoded by nucleic acids as described herein (e.g., BAL proteins, mutant forms of BAL proteins, fusion proteins, and the like).

The recombinant expression vectors of the invention can be designed for expression of BAL proteins in prokaryotic or eukaryotic cells. For example, BAL proteins can be expressed in bacterial cells such as *E. coli*, insect cells (using baculovirus expression vectors) yeast cells or mammalian cells. Suitable host cells are discussed further in Goeddel, *Gene Expression Technology: Methods in Enzymology* 185, Academic Press, San Diego, Calif. (1990). Alternatively, the recombinant expression vector can be transcribed and translated in vitro, for example using T7 promoter regulatory sequences and T7 polymerase.

Expression of proteins in prokaryotes is most often carried out in *E. coli* with vectors containing constitutive or inducible promoters directing the expression of either fusion or non-fusion proteins. Fusion vectors add a number of amino acids to a protein encoded therein, usually to the amino terminus of the recombinant protein. Such fusion vectors typically serve three purposes: 1) to increase expression of recombinant protein; 2) to increase the solubility of the recombinant protein; and 3) to aid in the purification of the recombinant protein by acting as a ligand in affinity purification. Often, in fusion expression vectors, a proteolytic cleavage site is introduced at the junction of the fusion moiety and the recombinant protein to enable separation of the recombinant protein from the fusion moiety subsequent to purification of the fusion protein. Such enzymes, and their cognate recognition sequences, include Factor Xa, thrombin and enterokinase. Typical fusion expression vectors include pGEX (Pharmacia Biotech Inc; Smith, D. B. and Johnson, K. S. (1988) *Gene* 67:31-40), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein.

Purified fusion proteins can be utilized in BAL activity assays, (e.g., direct assays or competitive assays described in detail below), or to generate antibodies specific for BAL proteins, for example. In a preferred embodiment, a BAL fusion protein expressed in a retroviral expression vector of the present invention can be utilized to infect bone marrow cells which are subsequently transplanted into irradiated recipients. The pathology of the subject recipient is then examined after sufficient time has passed (e.g., six (6) weeks).

Examples of suitable inducible non-fusion *E. coli* expression vectors include pTrc (Amann et al., (1988) *Gene* 69:301-315) and pET 11d (Studier et al., *Gene Expression Technology. Methods in Enzymology* 185, Academic Press, San Diego, Calif. (1990) 60-89). Target gene expression from the pTrc vector relies on host RNA polymerase transcription from a hybrid trp-lac fusion promoter. Target gene expression from the pET 11d vector relies on transcription from a T7 gn10-lac fusion promoter mediated by a coexpressed viral RNA polymerase (T7 gn1). This viral polymerase is supplied by host strains BL21(DE3) or HMS 174(DE3) from a resident prophage harboring a T7 gn1 gene under the transcriptional control of the lacUV 5 promoter.

One strategy to maximize recombinant protein expression in *E. coli* is to express the protein in a host bacteria with an impaired capacity to proteolytically cleave the recombinant protein (Gottesman, S., *Gene Expression Technology: Methods in Enzymology* 185, Academic Press, San Diego, Calif. (1990) 119-128). Another strategy is to alter the nucleic acid sequence of the nucleic acid to be inserted into an expression vector so that the individual codons for each amino acid are those preferentially utilized in *E. coli* (Wada et al., (1992) *Nucleic Acids Res.* 20:2111-2118). Such alteration of nucleic acid sequences of the invention can be carried out by standard DNA synthesis techniques.

In another embodiment, the BAL expression vector is a yeast expression vector. Examples of vectors for expression in yeast *S. cerivisae* include pYepSec1 (Baldari, et al., (1987) *Embo J.* 6:229-234), pMFa (Kurjan and Herskowitz, (1982) *Cell* 30:933-943), pJRY88 (Schultz et al., (1987) *Gene* 54:113-123), pYES2 (Invitrogen Corporation, San Diego, Calif.), and picZ (InVitrogen Corp, San Diego, Calif.).

Alternatively, BAL proteins can be expressed in insect cells using baculovirus expression vectors. Baculovirus vectors available for expression of proteins in cultured insect cells (e.g., Sf 9 cells) include the pAc series (Smith et al. (1983) *Mol. Cell Biol.* 3:2156-2165) and the pVL series (Lucklow and Summers (1989) *Virology* 170:31-39).

In yet another embodiment, a nucleic acid of the invention is expressed in mammalian cells using a mammalian expression vector. Examples of mammalian expression vectors include pCDM8 (Seed, B. (1987) *Nature* 329:840) and pMT2PC (Kaufman et al. (1987) *EMBO J.* 6:187-195). When used in mammalian cells, the expression vector's control functions are often provided by viral regulatory elements. For example, commonly used promoters are derived from polyoma, Adenovirus 2, cytomegalovirus and Simian Virus 40. For other suitable expression systems for both prokaryotic and eukaryotic cells see chapters 16 and 17 of Sambrook, J., Fritsh, E. F., and Maniatis, T. *Molecular Cloning. A Laboratory Manual. 2nd, ed., Cold Spring Harbor Laboratory*, Cold Spring Harbor Laboratory Press, Cold Spring Harbor, N.Y., 1989.

In another embodiment, the recombinant mammalian expression vector is capable of directing expression of the nucleic acid preferentially in a particular cell type (e.g., tissue-specific regulatory elements are used to express the nucleic acid). Tissue-specific regulatory elements are known in the art. Non-limiting examples of suitable tissue-specific promoters include the albumin promoter (liver-specific; Pinkert et al. (1987) *Genes Dev.* 1:268-277), lymphoid-specific promoters (Calame and Eaton (1988) *Adv. Immunol.* 43:235-275), in particular promoters of T cell receptors (Winoto and Baltimore (1989) *EMBO J.* 8:729-733) and immunoglobulins (Banerji et al. (1983) *Cell* 33:729-740; Queen and Baltimore (1983) *Cell* 33:741-748), neuron-specific promoters (e.g., the neurofilament promoter; Byrne and Ruddle (1989) *Proc. Natl. Acad. Sci. USA* 86:5473-5477), pancreas-specific promoters (Edlund et al. (1985) *Science* 230:912-916), and mammary gland-specific promoters (e.g., milk whey promoter; U.S. Pat. No. 4,873,316 and European Application Publication No. 264,166). Developmentally-regulated promoters are also encompassed, for example the murine hox promoters (Kessel and Gruss (1990) *Science* 249:374-379) and the α-fetoprotein promoter (Campes and Tilghman (1989) *Genes Dev.* 3:537-546).

The invention further provides a recombinant expression vector comprising a DNA molecule of the invention cloned into the expression vector in an antisense orientation. That is, the DNA molecule is operatively linked to a regulatory sequence in a manner which allows for expression (by transcription of the DNA molecule) of an RNA molecule which is antisense to BAL mRNA. Regulatory sequences operatively linked to a nucleic acid cloned in the antisense orientation can be chosen which direct the continuous expression of the antisense RNA molecule in a variety of cell types, for instance viral promoters and/or enhancers, or regulatory sequences can be chosen which direct constitutive, tissue specific or cell type specific expression of antisense RNA. The antisense expression vector can be in the form of a recombinant plasmid, phagemid or attenuated virus in which antisense nucleic acids are produced under the control of a high efficiency regulatory region, the activity of which can be determined by the cell type into which the vector is introduced. For a discussion of the regulation of gene expression using antisense genes see Weintraub, H. et al., Antisense RNA as a molecular tool for genetic analysis, *Reviews—Trends in Genetics*, Vol. 1(1) 1986.

Another aspect of the invention pertains to host cells into which a BAL nucleic acid molecule of the invention is introduced, e.g., a BAL nucleic acid molecule within a recombinant expression vector or a BAL nucleic acid molecule containing sequences which allow it to homologously recombine into a specific site of the host cell's genome. The terms "host cell" and "recombinant host cell" are used interchangeably herein. It is understood that such terms refer not only to the particular subject cell but to the progeny or potential progeny of such a cell. Because certain modifications may occur in succeeding generations due to either mutation or environmental influences, such progeny may not, in fact, be identical to the parent cell, but are still included within the scope of the term as used herein.

A host cell can be any prokaryotic or eukaryotic cell. For example, a BAL protein can be expressed in bacterial cells such as *E. coli*, insect cells, yeast or mammalian cells (such as Chinese hamster ovary cells (CHO) or COS cells). Other suitable host cells are known to those skilled in the art.

Vector DNA can be introduced into prokaryotic or eukaryotic cells via conventional transformation or transfection techniques. As used herein, the terms "transformation" and "transfection" are intended to refer to a variety of art-recognized techniques for introducing foreign nucleic acid (e.g., DNA) into a host cell, including calcium phosphate or calcium chloride co-precipitation, DEAE-dextran-mediated transfection, lipofection, or electroporation. Suitable methods for transforming or transfecting host cells can be found in Sambrook, et al. (*Molecular Cloning: A Laboratory Manual.* 2nd, ed, *Cold Spring Harbor Laboratory*, Cold Spring Harbor Laboratory Press, Cold Spring Harbor, N.Y., 1989), and other laboratory manuals.

For stable transfection of mammalian cells, it is known that, depending upon the expression vector and transfection technique used, only a small fraction of cells may integrate the foreign DNA into their genome. In order to identify and select these integrants, a gene that encodes a selectable marker (e.g., resistance to antibiotics) is generally introduced into the host cells along with the gene of interest. Preferred selectable markers include those which confer resistance to drugs, such as G418, hygromycin and methotrexate. Nucleic acid encoding a selectable marker can be introduced into a host cell on the same vector as that encoding a BAL protein or can be introduced on a separate vector. Cells stably transfected with the introduced nucleic acid can be identified by drug selection (e.g., cells that have incorporated the selectable marker gene will survive, while the other cells die).

A host cell of the invention, such as a prokaryotic or eukaryotic host cell in culture, can be used to produce (i.e., express) a BAL protein. Accordingly, the invention further provides methods for producing a BAL protein using the host cells of the invention. In one embodiment, the method comprises culturing the host cell of invention (into which a recombinant expression vector encoding a BAL protein has been introduced) in a suitable medium such that a BAL protein is produced. In another embodiment, the method further comprises isolating a BAL protein from the medium or the host cell.

The host cells of the invention can also be used to produce non-human transgenic animals. For example, in one embodiment, a host cell of the invention is a fertilized oocyte or an embryonic stem cell into which BAL-coding sequences have been introduced. Such host cells can then be used to create non-human transgenic animals in which exogenous BAL sequences have been introduced into their genome or homologous recombinant animals in which endogenous BAL sequences have been altered. Such animals are useful for studying the function and/or activity of a BAL and for identifying and/or evaluating modulators of BAL activity. As used herein, a "transgenic animal" is a non-human animal, preferably a mammal, more preferably a rodent such as a rat or mouse, in which one or more of the cells of the animal includes a transgene. Other examples of transgenic animals include non-human primates, sheep, dogs, cows, goats, chickens, amphibians, and the like. A transgene is exogenous DNA which is integrated into the genome of a cell from which a transgenic animal develops and which remains in the genome of the mature animal, thereby directing the expression of an encoded gene product in one or more cell types or tissues of the transgenic animal. As used herein, a "homologous recombinant animal" is a non-human animal, preferably a mammal, more preferably a mouse, in which an endogenous BAL gene has been altered by homologous recombination between the endogenous gene and an exogenous DNA molecule introduced into a cell of the animal, e.g., an embryonic cell of the animal, prior to development of the animal.

A transgenic animal of the invention can be created by introducing a BAL-encoding nucleic acid into the male pronuclei of a fertilized oocyte, e.g., by microinjection, retroviral infection, and allowing the oocyte to develop in a pseudopregnant female foster animal. The BAL cDNA sequence of SEQ ID NO:1 or 4 can be introduced as a transgene into the genome of a non-human animal. Alternatively, a nonhuman homologue of a human BAL gene, such as a mouse or rat BAL gene, can be used as a transgene. Alternatively, a BAL gene homologue, can be isolated based on hybridization to the BAL cDNA sequences of SEQ ID NO:1, 3, 4, or 6 (described further in subsection I above) and used as a transgene. Intronic sequences and polyadenylation signals can also be included in the transgene to increase the efficiency of expression of the transgene. A tissue-specific regulatory sequence(s) can be operably linked to a BAL transgene to direct expression of a BAL protein to particular cells. Methods for generating transgenic animals via embryo manipulation and microinjection, particularly animals such as mice, have become conventional in the art and are described, for example, in U.S. Pat. Nos. 4,736,866 and 4,870,009, both by Leder el al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of a BAL transgene in its genome and/or expression of BAL mRNA in tissues or cells of the animals. A transgenic founder animal can then be used to breed additional animals carrying the transgene. Moreover, transgenic animals carrying a transgene encoding a BAL protein can further be bred to other transgenic animals carrying other transgenes.

To create a homologous recombinant animal, a vector is prepared which contains at least a portion of a BAL gene into which a deletion, addition or substitution has been introduced to thereby alter, e.g., functionally disrupt, the BAL gene. The BAL gene can be a human gene (e.g., the cDNA of SEQ ID NO:3), but more preferably, is a non-human homologue of a human BAL gene (e.g., the cDNA of SEQ ID NO:6). For example, a mouse BAL gene can be used to construct a homologous recombination nucleic acid molecule, e.g., a vector, suitable for altering an endogenous BAL gene in the mouse genome. In a preferred embodiment, the homologous recombination nucleic acid molecule is designed such that, upon homologous recombination, the endogenous BAL gene is functionally disrupted (i.e., no longer encodes a functional protein; also referred to as a "knock out" vector). Alternatively, the homologous recombination nucleic acid molecule can be designed such that, upon homologous recombination, the endogenous BAL gene is mutated or otherwise altered but still encodes functional protein (e.g., the upstream regulatory region can be altered to thereby alter the expression of the endogenous BAL protein). In the homologous recombination nucleic acid molecule, the altered portion of the BAL gene is flanked at its 5' and 3' ends by additional nucleic acid sequence of the BAL gene to allow for homologous recombination to occur between the exogenous BAL gene carried by the homologous recombination nucleic acid molecule and an endogenous BAL gene in a cell, e.g., an embryonic stem cell. The additional flanking BAL nucleic acid sequence is of sufficient length for successful homologous recombination with the endogenous gene. Typically, several kilobases of flanking DNA (both at the 5' and 3' ends) are included in the homologous recombination nucleic acid molecule (see, e.g., Thomas, K. R. and Capecchi, M. R. (1987) *Cell* 51:503 for a description of homologous recombination vectors). The homologous recombination nucleic acid molecule is introduced into a cell, e.g., an embryonic stem cell line (e.g., by electroporation) and cells in which the introduced BAL gene has homologously recombined with the endogenous BAL gene are selected (see e.g., Li, E. et al. (1992) *Cell* 69:915). The selected cells can then injected into a blastocyst of an animal (e.g., a mouse) to form aggregation chimeras (see e.g., Bradley, A. in *Teratocarcinomas and Embryonic Stem Cells: A Practical Approach*, E. J. Robertson, ed. (IRL, Oxford, 1987) pp. 113-152). A chimeric embryo can then be implanted into a suitable pseudopregnant female foster animal and the embryo brought to term. Progeny harboring the homologously recombined DNA in their germ cells can be used to breed animals in which all cells of the animal contain the homologously recombined DNA by germline transmission of the transgene. Methods for constructing homologous recombination nucleic acid molecules, e.g., vectors, or homologous recombinant animals are described further in Bradley, A. (1991) *Current Opinion in Biotechnology* 2:823-829 and in PCT International Publication Nos.: WO 90/11354 by Le Mouellec et al.; WO 91/01140 by Smithies et al.; WO 92/0968 by Zijlstra et al.; and WO 93/04169 by Bems et al.

In another embodiment, transgenic non-humans animals can be produced which contain selected systems which allow for regulated expression of the transgene. One example of such a system is the cre/loxP recombinase system of bacteriophage P1. For a description of the cre/loxP recombinase system, see, e.g., Lakso et al. (1992) *Proc. Natl. Acad. Sci. USA* 89:6232-6236. Another example of a recombinase system is the FLP recombinase system of *Saccharomyces cerevisiae* (O'Gorman et al. (1991) *Science* 251:1351-1355. If a cre/loxP recombinase system is used to regulate expression of the transgene, animals containing transgenes encoding both the Cre recombinase and a selected protein are required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. (1997) *Nature* 385:810-813 and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The recontructed oocyte is then cultured such that it develops to morula or blastocyte and then transferred to pseudopregnant female foster animal. The offspring borne of this female foster animal will be a clone of the animal from which the cell, e.g., the somatic cell, is isolated.

IV. Pharmaceutical Compositions

The BAL nucleic acid molecules, fragments of BAL proteins, and anti-BAL antibodies (also referred to herein as "active compounds") of the invention can be incorporated into pharmaceutical compositions suitable for administration. Such compositions typically comprise the nucleic acid molecule, protein, or antibody and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a fragment of a BAL protein or an anti-BAL antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules, oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of such compounds can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

The nucleic acid molecules of the invention can be inserted into vectors and used as gene therapy vectors. Gene therapy vectors can be delivered to a subject by, for example, intravenous injection, local administration (see U.S. Pat. No. 5,328,470) or by stereotactic injection (see e.g., Chen et al. (1994) *Proc. Natl. Acad. Sci. USA* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

V. Uses and Methods of the Invention

The nucleic acid molecules, proteins, protein homologues, and antibodies described herein can be used in one or more of the following methods: a) screening assays; b) predictive medicine (e.g., diagnostic assays, prognostic assays, monitoring clinical trials, and pharmacogenetics); and c) methods of treatment (e.g., therapeutic and prophylactic). As described herein, a BAL protein of the invention has one or more of the following activities: (1) it interacts with a non-BAL protein molecule, e.g., CRK, CRK-L, SHP-2, P13K, or ZAP70; (2) it activates a BAL-dependent signal transduction pathway; (3) it modulates the occurrence and severity of a malignancy such as a lymphoma, e.g., non-Hodgkin's lymphoma; and (4) it modulates cell migration, motility, and shape, as well as cell/cell and cell/extra-cellular matrix interactions, and, thus, can be used to, for example, (1) modulate the interaction with a non-BAL protein molecule; (2) activate a BAL-dependent signal transduction pathway; (3) modulate the occurrence and severity of a malignancy such as a lymphoma, e.g., non-Hodgkin's lymphoma; and (4) modulate cell migration, motility, and shape, as well as cell/cell and cell/extra-cellular matrix interactions.

The isolated nucleic acid molecules of the invention can be used, for example, to express BAL protein (e.g., via a recombinant expression vector in a host cell in gene therapy applications), to detect BAL mRNA (e.g., in a biological sample) or a genetic alteration in a BAL gene, and to modulate BAL activity, as described further below. The BAL proteins can be used to treat disorders characterized by insufficient or excessive production of a BAL substrate or production of BAL inhibitors. In addition, the BAL proteins can be used to screen for naturally occurring BAL substrates, to screen for drugs or compounds which modulate BAL activity, as well as to treat disorders characterized by insufficient or excessive production of BAL protein or production of BAL protein forms which have decreased or aberrant activity compared to BAL wild type protein (e.g., Non-Hodgkin's lymphoma). Moreover, the anti-BAL antibodies of the invention can be used to detect and isolate BAL proteins, regulate the bioavailability of BAL proteins, and modulate BAL activity.

A. Screening Assays:

The invention provides a method (also referred to herein as a "screening assay") for identifying and/or producing modulators, i.e., candidate or test compounds or agents (e.g., peptides, peptidomimetics, small molecules or other drugs) which bind to BAL proteins, have a stimulatory or inhibitory effect on, for example, BAL expression or BAL activity, or have a stimulatory or inhibitory effect on, for example, the expression or activity of a BAL substrate.

In one embodiment, the invention provides assays for screening candidate or test compounds which are substrates of a BAL protein or polypeptide or biologically active portion thereof. In another embodiment, the invention provides assays for screening candidate or test compounds which bind to or modulate the activity of a BAL protein or polypeptide or biologically active portion thereof. The test compounds of the present invention can be obtained using any of the numerous approaches in combinatorial library methods known in the art, including: biological libraries; spatially addressable parallel solid phase or solution phase libraries; synthetic library methods requiring deconvolution; the 'one-bead one-compound' library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

Examples of methods for the synthesis of molecular libraries can be found in the art, for example in: DeWitt et al. (1993) *Proc. Natl. Acad. Sci. U.S.A.* 90:6909; Erb et al. (1994) *Proc. Natl. Acad. Sci. USA* 91:11422; Zuckermann et al. (1994). *J. Med. Chem.* 37:2678; Cho et al. (1993) *Science* 261:1303; Carrell et al. (1994) *Angew. Chem. Int. Ed. Engl.* 33:2059; Carell et al. (1994) *Angew. Chem. Int. Ed. Engl.* 33:2061; and in Gallop et al. (1994) *J. Med. Chem.* 37:1233.

Libraries of compounds may be presented in solution (e.g., Houghten (1992) *Biotechniques* 13:412-421), or on beads (Lam (1991) *Nature* 354:82-84), chips (Fodor (1993) *Nature* 364:555-556), bacteria (Ladner U.S. Pat. No. 5,223,409), spores (Ladner USP '409), plasmids (Cull et al. (1992) *Proc Natl Acad Sci USA* 89:1865-1869) or on phage (Scott and Smith (1990) *Science* 249:386-390); (Devlin (1990) *Science* 249:404-406); (Cwirla et al. (1990) *Proc. Natl. Acad. Sci.* 87:6378-6382); (Felici (1991) *J. Mol. Biol.* 222:301-310); (Ladner supra.).

In one embodiment, an assay is a cell-based assay in which a cell which expresses a BAL protein or biologically active portion thereof is contacted with a test compound and the ability of the test compound to modulate BAL activity is determined. Determining the ability of the test compound to modulate BAL activity can be accomplished by monitoring, for example, the survival of a cell which expresses BAL or the activity of a BAL-regulated transcription factor. The cell, for example, can be of mammalian origin, e.g., a peripheral blood cell.

The ability of the test compound to modulate BAL binding to a substrate or to bind to BAL can also be determined. Determining the ability of the test compound to modulate BAL binding to a substrate can be accomplished, for example, by coupling the BAL substrate with a radioisotope or enzymatic label such that binding of the BAL substrate to BAL can be determined by detecting the labeled BAL substrate in a complex. Determining the ability of the test compound to bind BAL can be accomplished, for example, by coupling the compound with a radioisotope or enzymatic label such that binding of the compound to BAL can be determined by detecting the labeled BAL compound in a complex. For example, compounds (e.g., BAL substrates) can be labeled with $^{125}$I, $^{35}$S, $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product.

It is also within the scope of this invention to determine the ability of a compound (e.g., a BAL substrate) to interact with BAL without the labeling of any of the interactants. For example, a microphysiometer can be used to detect the interaction of a compound with BAL without the labeling of either the compound or the BAL. McConnell, H. M. et al. (1992) Science 257:1906-1912. As used herein, a "microphysiometer" (e.g., Cytosensor) is an analytical instrument that measures the rate at which a cell acidifies its environment using a light-addressable potentiometric sensor (LAPS). Changes in this acidification rate can be used as an indicator of the interaction between a compound and BAL.

In another embodiment, an assay is a cell-based assay comprising contacting a cell expressing a BAL target molecule (e.g., a BAL substrate) with a test compound and determining the ability of the test compound to modulate (e.g. stimulate or inhibit) the activity of the BAL target molecule. Determining the ability of the test compound to modulate the activity of a BAL target molecule can be accomplished, for example, by determining the ability of the BAL protein to bind to or interact with the BAL target molecule.

Determining the ability of the BAL protein or a biologically active fragment thereof, to bind to or interact with a BAL target molecule can be accomplished by one of the methods described above for determining direct binding. In a preferred embodiment, determining the ability of the BAL protein to bind to or interact with a BAL target molecule can be accomplished by determining the activity of the target molecule. For example, the activity of the target molecule can be determined by detecting induction of a cellular second messenger of the target (i.e., intracellular $Ca^{2+}$, diacylglycerol, $IP_3$, and the like), detecting catalytic/enzymatic activity of the target an appropriate substrate, detecting the induction of a reporter gene (comprising a target-responsive regulatory element operatively linked to a nucleic acid encoding a detectable marker, e.g., luciferase), or detecting a target-regulated cellular response.

In yet another embodiment, an assay of the present invention is a cell-free assay in which a BAL protein or biologically active portion thereof is contacted with a test compound and the ability of the test compound to bind to the BAL protein or biologically active portion thereof is determined. Preferred biologically active portions of the BAL proteins to be used in assays of the present invention include fragments which participate in interactions with non-BAL molecules, e.g., fragments with high surface probability scores. Binding of the test compound to the BAL protein can be determined either directly or indirectly as described above. In a preferred embodiment, the assay includes contacting the BAL protein or biologically active portion thereof with a known compound which binds BAL to form an assay mixture, contacting the assay mixture with a test compound, and determining the ability of the test compound to interact with a BAL protein, wherein determining the ability of the test compound to interact with a BAL protein comprises determining the ability of the test compound to preferentially bind to BAL or biologically active portion thereof as compared to the known compound.

In another embodiment, the assay is a cell-free assay in which a BAL protein or biologically active portion thereof is contacted with a test compound and the ability of the test compound to modulate (e.g., stimulate or inhibit) the activity of the BAL protein or biologically active portion thereof is determined. Determining the ability of the test compound to modulate the activity of a BAL protein can be accomplished, for example, by determining the ability of the BAL protein to bind to a BAL target molecule by one of the methods described above for determining direct binding. Determining the ability of the BAL protein to bind to a BAL target molecule can also be accomplished using a technology such as real-time Biomolecular Interaction Analysis (BIA). Sjolander, S. and Urbaniczky, C. (1991) Anal. Chem. 63:2338-2345 and Szabo et al. (1995) Curr. Opin. Struct. Biol. 5:699-705. As used herein, "BIA" is a technology for studying biospecific interactions in real time, without labeling any of the interactants (e.g., BIAcore). Changes in the optical phenomenon of surface plasmon resonance (SPR) can be used as an indication of real-time reactions between biological molecules.

In an alternative embodiment, determining the ability of the test compound to modulate the activity of a BAL protein can be accomplished by determining the ability of the BAL protein to further modulate the activity of a downstream effector of a BAL target molecule. For example, the activity of the effector molecule on an appropriate target can be determined or the binding of the effector to an appropriate target can be determined as previously described.

The cell-free assays of the present invention are amenable to use of both soluble and/or membrane-bound forms of isolated proteins (e.g., BAL proteins or biologically active portions thereof). In the case of cell-free assays in which a membrane-bound form of an isolated protein is used it may be desirable to utilize a solubilizing agent such that the membrane-bound form of the isolated protein is maintained in solution. Examples of such solubilizing agents include nonionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylamminio]-1-propane sulfonate (CHAPS), 3-[(3-cholamidopropyl)dimethylamminio]-2-hydroxy-1-propane sulfonate (CHAPSO), or N-dodecyl=N,N-dimethyl-3-ammonio-1-propane sulfonate.

In more than one embodiment of the above assay methods of the present invention, it may be desirable to immobilize either BAL or its target molecule to facilitate separation of complexed from uncomplexed forms of one or both of the proteins, as well as to accommodate automation of the assay. Binding of a test compound to a BAL protein, or interaction of a BAL protein with a target molecule in the presence and absence of a candidate compound, can be accomplished in any vessel suitable for containing the reactants. Examples of such vessels include microtitre plates, test tubes, and microcentrifuge tubes. In one embodiment, a fusion protein can be provided which adds a domain that allows one or both of the proteins to be bound to a matrix. For example, glutathione-S-transferase/ BAL fusion proteins or glutathione-S-transferase/target fusion proteins can be adsorbed onto glutathione sepharose beads (Sigma Chemical, St. Louis, Mo.) or glutathione derivatized microtitre plates, which are then combined with the test compound or the test compound and either the non-adsorbed target protein or BAL protein, and the mixture incubated under conditions conducive to complex formation (e.g., at physiological conditions for salt and pH). Following incubation, the beads or microtitre plate wells are washed to remove any unbound components, the matrix immobilized in the case of beads, complex determined either directly or indirectly, for example, as described above. Alternatively, the complexes can be dissociated from the matrix, and the level of BAL binding or activity determined using standard techniques.

Other techniques for immobilizing proteins on matrices can also be used in the screening assays of the invention. For example, either a BAL protein or a BAL target molecule can be immobilized utilizing conjugation of biotin and streptavidin. Biotinylated BAL protein or target molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). Alternatively, antibodies reactive with BAL protein or target molecules but which do not interfere with binding of the BAL protein to its target molecule can be derivatized to the wells of the plate, and unbound target or BAL protein trapped in the wells by antibody conjugation. Methods for detecting such complexes, in addition to those described above for the GST-immobilized complexes, include immunodetection of complexes using antibodies reactive with the BAL protein or target molecule, as well as enzyme-linked assays which rely on detecting an enzymatic activity associated with the BAL protein or target molecule.

In another embodiment, modulators of BAL expression are produced or identified in a method wherein a cell is contacted with a candidate compound and the expression of BAL mRNA or protein in the cell is determined. The level of expression of BAL mRNA or protein in the presence of the candidate compound is compared to the level of expression of BAL mRNA or protein in the absence of the candidate compound. The candidate compound can then be produced or identified as a modulator of BAL expression based on this comparison. For example, when expression of BAL mRNA or protein is greater (statistically significantly greater) in the presence of the candidate compound than in its absence, the candidate compound is identified as a stimulator of BAL mRNA or protein expression (i.e. a stimulator of BAL mRNA or protein expression is produced). Alternatively, when expression of BAL mRNA or protein is less (statistically significantly less) in the presence of the candidate compound than in its absence, the candidate compound is produced or identified as an inhibitor of BAL mRNA or protein expression (i.e. an inhibitor of BAL mRNA or protein expression is produced). The level of BAL mRNA or protein expression in the cells can be determined by methods described herein for detecting BAL mRNA or protein.

In yet another aspect of the invention, the BAL proteins can be used as "bait proteins" in a two-hybrid assay or three-hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Biotechniques 14:920-924; Iwabuchi et al. (1993) Oncogene 8:1693-1696; and Brent WO94/10300), to identify other proteins, which bind to or interact with BAL ("BAL-binding proteins" or "BAL-bp") and are involved in BAL activity. Such BAL-binding proteins are also likely to be involved in the propagation of signals by the BAL proteins or BAL targets as, for example, downstream elements of a BAL-mediated signaling pathway. Alternatively, such BAL-binding proteins are likely to be BAL inhibitors.

The two-hybrid system is based on the modular nature of most transcription factors, which consist of separable DNA-binding and activation domains. Briefly, the assay utilizes two different DNA constructs. In one construct, the gene that codes for a BAL protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a BAL-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the BAL protein.

This invention further pertains to novel agents identified by the above-described screening assays. Accordingly, it is within the scope of this invention to further use an agent identified and/or produced as described herein in an appropriate animal model. For example, an agent identified and/or produced as described herein (e.g., a BAL modulating agent, an antisense BAL nucleic acid molecule, a BAL-specific antibody, or a BAL-binding partner) can be used in an animal model to determine the efficacy, toxicity, or side effects of treatment with such an agent. Alternatively, an agent identified and/or produced as described herein can be used in an animal model to determine the mechanism of action of such an agent. Furthermore, this invention pertains to uses of novel agents identified and/or produced by the above-described screening assays for treatments as described herein.

B. Detection Assays

Portions or fragments of the cDNA sequences identified herein (and the corresponding complete gene sequences) can be used in numerous ways as polynucleotide reagents. For example, these sequences can be used to: (i) map their respective genes on a chromosome; and, thus, locate gene regions associated with genetic disease; (ii) identify an individual from a minute biological sample (tissue typing); and (iii) aid in forensic identification of a biological sample. These applications are described in the subsections below.

1. Chromosome Mapping

Once the sequence (or a portion of the sequence) of a gene has been isolated, this sequence can be used to map the location of the gene on a chromosome. This process is called chromosome mapping. Accordingly, portions or fragments of the BAL nucleotide sequences, described herein, can be used to map the location of the BAL genes on a chromosome (further described in Example 1, below). The mapping of the BAL sequences to chromosomes is an important first step in correlating these sequences with genes associated with disease.

Briefly, BAL genes can be mapped to chromosomes by preparing PCR primers (preferably 15-25 bp in length) from the BAL nucleotide sequences. Computer analysis of the BAL sequences can be used to predict primers that do not span more than one exon in the genomic DNA, thus complicating the amplification process. These primers can then be used for PCR screening of somatic cell hybrids containing individual human chromosomes. Only those hybrids containing the human gene corresponding to the BAL sequences will yield an amplified fragment.

Somatic cell hybrids are prepared by fusing somatic cells from different mammals (e.g., human and mouse cells). As hybrids of human and mouse cells grow and divide, they gradually lose human chromosomes in random order, but retain the mouse chromosomes. By using media in which mouse cells cannot grow, because they lack a particular enzyme, but human cells can, the one human chromosome that contains the gene encoding the needed enzyme, will be retained. By using various media, panels of hybrid cell lines can be established. Each cell line in a panel contains either a single human chromosome or a small number of human chromosomes, and a full set of mouse chromosomes, allowing easy mapping of individual genes to specific human chromosomes. (D'Eustachio P. et al. (1983) *Science* 220:919-924). Somatic cell hybrids containing only fragments of human chromosomes can also be produced by using human chromosomes with translocations and deletions.

PCR mapping of somatic cell hybrids is a rapid procedure for assigning a particular sequence to a particular chromosome. Three or more sequences can be assigned per day using a single thermal cycler. Using the BAL nucleotide sequences to design oligonucleotide primers, sublocalization can be achieved with panels of fragments from specific chromosomes. Other mapping strategies which can similarly be used to map a BAL sequence to its chromosome include in situ hybridization (described in Fan, Y. et al. (1990) *Proc. Natl. Acad. Sci. US,*4, 87:6223-27), pre-screening with labeled flow-sorted chromosomes, and pre-selection by hybridization to chromosome specific cDNA libraries.

Fluorescence in situ hybridization (FISH) of a DNA sequence to a metaphase chromosomal spread can further be used to provide a precise chromosomal location in one step. Chromosome spreads can be made using cells whose division has been blocked in metaphase by a chemical such as colcemid that disrupts the mitotic spindle. The chromosomes can be treated briefly with trypsin, and then stained with Giemsa. A pattern of light and dark bands develops on each chromosome, so that the chromosomes can be identified individually. The FISH technique can be used with a DNA sequence as short as 500 or 600 bases. However, clones larger than 1,000 bases have a higher likelihood of binding to a unique chromosomal location with sufficient signal intensity for simple detection. Preferably 1,000 bases, and more preferably 2,000 bases will suffice to get good results at a reasonable amount of time. For a review of this technique, see Verma et al., Human Chromosomes: A Manual of Basic Techniques (Pergamon Press, New York 1988).

Reagents for chromosome mapping can be used individually to mark a single chromosome or a single site on that chromosome, or panels of reagents can be used for marking multiple sites and/or multiple chromosomes. Reagents corresponding to noncoding regions of the genes actually are preferred for mapping purposes. Coding sequences are more likely to be conserved within gene families, thus increasing the chance of cross hybridizations during chromosomal mapping.

Once a sequence has been mapped to a precise chromosomal location, the physical position of the sequence on the chromosome can be correlated with genetic map data. (Such data are found, for example, in V. McKusick, Mendelian Inheritance in Man, available on-line through Johns Hopkins University Welch Medical Library). The relationship between a gene and a disease, mapped to the same chromosomal region, can then be identified through linkage analysis (co-inheritance of physically adjacent genes), described in, for example, Egeland, J. et al. (1987) *Nature*, 325:783-787.

Moreover, differences in the DNA sequences between individuals affected and unaffected with a disease associated with the BAL gene, can be determined. If a mutation is observed in some or all of the affected individuals but not in any unaffected individuals, then the mutation is likely to be the causative agent of the particular disease. Comparison of affected and unaffected individuals generally involves first looking for structural alterations in the chromosomes, such as deletions or translocations that are visible from chromosome spreads or detectable using PCR based on that DNA sequence. Ultimately, complete sequencing of genes from several individuals can be performed to confirm the presence of a mutation and to distinguish mutations from polymorphisms.

2. Tissue Typing

The BAL sequences of the present invention can also be used to identify individuals from minute biological samples. The United States military, for example, is considering the use of restriction fragment length polymorphism (RFLP) for identification of its personnel. In this technique, an individual's genomic DNA is digested with one or more restriction enzymes, and probed on a Southern blot to yield unique bands for identification. This method does not suffer from the current limitations of "Dog Tags" which can be lost, switched, or stolen, making positive identification difficult. The sequences of the present invention are useful as additional DNA markers for RFLP (described in U.S. Pat. No. 5,272,057).

Furthermore, the sequences of the present invention can be used to provide an alternative technique which determines the actual base-by-base DNA sequence of selected portions of an individual's genome. Thus, the BAL nucleotide sequences described herein can be used to prepare two PCR primers from the 5' and 3' ends of the sequences. These primers can then be used to amplify an individual's DNA and subsequently sequence it.

Panels of corresponding DNA sequences from individuals, prepared in this manner, can provide unique individual identifications, as each individual will have a unique set of such DNA sequences due to allelic differences. The sequences of the present invention can be used to obtain such identification sequences from individuals and from tissue. The BAL nucleotide sequences of the invention uniquely represent portions of the human genome. Allelic variation occurs to some degree in the coding regions of these sequences, and to a greater degree in the noncoding regions. It is estimated that allelic variation between individual humans occurs with a frequency of about once per each 500 bases. Each of the sequences described herein can, to some degree, be used as a standard against which DNA from an individual can be compared for identification purposes. Because greater numbers of polymorphisms occur in the noncoding regions, fewer sequences are necessary to differentiate individuals. The noncoding sequences of SEQ ID NO:1 or 4 can comfortably provide positive individual identification with a panel of perhaps 10 to 1,000 primers which each yield a noncoding amplified sequence of 100 bases. If predicted coding sequences, such as those in SEQ ID NO:3 or 6 are used, a more appropriate number of primers for positive individual identification would be 500-2,000.

If a panel of reagents from BAL nucleotide sequences described herein is used to generate a unique identification database for an individual, those same reagents can later be used to identify tissue from that individual. Using the unique identification database, positive identification of the individual, living or dead, can be made from extremely small tissue samples.

3. Use of Partial BAL Sequences in Forensic Biology

DNA-based identification techniques can also be used in forensic biology. Forensic biology is a scientific field employing genetic typing of biological evidence found at a crime scene as a means for positively identifying, for example, a perpetrator of a crime. To make such an identification, PCR technology can be used to amplify DNA sequences taken from very small biological samples such as tissues, e.g., hair or skin, or body fluids, e.g., blood, saliva, or semen found at a crime scene. The amplified sequence can then be compared to a standard, thereby allowing identification of the origin of the biological sample.

The sequences of the present invention can be used to provide polynucleotide reagents, e.g., PCR primers, targeted to specific loci in the human genome, which can enhance the reliability of DNA-based forensic identifications by, for example, providing another "identification marker" (i.e. another DNA sequence that is unique to a particular individual). As mentioned above, actual base sequence information can be used for identification as an accurate alternative to patterns formed by restriction enzyme generated fragments. Sequences targeted to noncoding regions of SEQ ID NO:1 or 4 are particularly appropriate for this use as greater numbers of polymorphisms occur in the noncoding regions, making it easier to differentiate individuals using this technique. Examples of polynucleotide reagents include the BAL nucleotide sequences or portions thereof, e.g., fragments derived from the noncoding regions of SEQ ID NO:1 or 4 having a length of at least 20 bases, preferably at least 30 bases.

The BAL nucleotide sequences described herein can further be used to provide polynucleotide reagents, e.g., labeled or labelable probes which can be used in, for example, an in situ hybridization technique, to identify a specific tissue, e.g., brain tissue. This can be very useful in cases where a forensic pathologist is presented with a tissue of unknown origin. Panels of such BAL probes can be used to identify tissue by species and/or by organ type.

In a similar fashion, these reagents, e.g., BAL primers or probes can be used to screen tissue culture for contamination (i.e. screen for the presence of a mixture of different types of cells in a culture).

C. Predictive Medicine:

The present invention also pertains to the field of predictive medicine in which diagnostic assays, prognostic assays, and monitoring clinical trials are used for prognostic (predictive) purposes to thereby treat an individual prophylactically. Accordingly, one aspect of the present invention relates to diagnostic assays for determining BAL protein and/or nucleic acid expression as well as BAL activity, in the context of a biological sample (e.g., blood, serum, cells, tissue) to thereby determine whether an individual is afflicted with a disease or disorder, or is at risk of developing a disorder, associated with aberrant BAL expression or activity, e.g., a malignancy such as a lymphoma, e.g., non-Hodgkin's lymphoma. The invention also provides for prognostic (or predictive) assays for determining whether an individual is at risk of developing a disorder associated with BAL protein, nucleic acid expression or activity. For example, mutations in a BAL gene can be assayed in a biological sample. Such assays can be used for prognostic or predictive purpose to thereby phophylactically treat an individual prior to the onset of a disorder characterized by or associated with BAL protein, nucleic acid expression or activity e.g., a malignancy such as a lymphoma, e.g., non-Hodgkin's lymphoma.

Another aspect of the invention pertains to monitoring the influence of agents (e.g., drugs, compounds) on the expression or activity of BAL in clinical trials.

These and other agents are described in further detail in the following sections.

1. Diagnostic Assays An exemplary method for detecting the presence or absence of BAL protein or nucleic acid in a biological sample involves obtaining a biological sample from a test subject and contacting the biological sample with a compound or an agent capable of detecting BAL protein or nucleic acid (e.g., mRNA or genomic DNA) that encodes BAL protein such that the presence of BAL protein or nucleic acid is detected in the biological sample. A preferred agent for detecting BAL mRNA or genomic DNA is a labeled nucleic acid probe capable of hybridizing to BAL mRNA or genomic DNA. The nucleic acid probe can be, for example, a full-length BAL nucleic acid, such as the nucleic acid of SEQ ID NO:1, 3, 4, or 6, or a portion thereof, such as an oligonucleotide of at least 15, 30, 50, 100, 250 or 500 nucleotides in length and sufficient to specifically hybridize under stringent conditions to BAL mRNA or genomic DNA. Other suitable probes for use in the diagnostic assays of the invention are described herein.

A preferred agent for detecting BAL protein is an antibody capable of binding to BAL protein, preferably an antibody with a detectable label. Antibodies can be polyclonal, or more preferably, monoclonal. An intact antibody, or a fragment thereof (e.g., Fab or $F(ab')_2$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently labeled streptavidin. The term "biological sample" is intended to include tissues, cells and biological fluids isolated from a subject, as well as tissues, cells and fluids present within a subject. That is, the detection method of the invention can be used to detect BAL mRNA, protein, or genomic DNA in a biological sample in vitro as well as in vivo. For example, in vitro techniques for detection of BAL mRNA include Northern hybridizations and in situ hybridizations. In vitro techniques for detection of BAL protein include enzyme linked immunosorbent assays (ELISAs), Western blots, immunoprecipitations and immunofluorescence. In vitro techniques for detection of BAL genomic DNA include Southern hybridizations. Furthermore, in vivo techniques for detection of BAL protein include introducing into a subject a labeled anti-BAL antibody. For example, the antibody can be labeled with a radioactive marker whose presence and location in a subject can be detected by standard imaging techniques.

In one embodiment, the biological sample contains protein molecules from the test subject. Alternatively, the biological sample can contain mRNA molecules from the test subject or genomic DNA molecules from the test subject. A preferred biological sample is a serum sample isolated by conventional means from a subject.

In another embodiment, the methods further involve obtaining a control biological sample from a control subject, contacting the control sample with a compound or agent capable of detecting BAL protein, mRNA, or genomic DNA, such that the presence of BAL protein, mRNA or genomic DNA is detected in the biological sample, and comparing the presence of BAL protein, mRNA or genomic DNA in the control sample with the presence of BAL protein, mRNA or genomic DNA in the test sample.

The invention also encompasses kits for detecting the presence of BAL in a biological sample. For example, the kit can comprise a labeled compound or agent capable of detecting BAL protein or mRNA in a biological sample; means for determining the amount of BAL in the sample; and means for comparing the amount of BAL in the sample with a standard. The compound or agent can be packaged in a suitable container. The kit can further comprise instructions for using the kit to detect BAL protein or nucleic acid.

2. Prognostic Assays

The diagnostic methods described herein can furthermore be utilized to identify subjects having or at risk of developing a disease or disorder associated with aberrant BAL expression or activity e.g., a malignancy such as a lymphoma, e.g., non-Hodgkin's lymphoma. As used herein, the term "aberrant" includes a BAL expression or activity which deviates from the wild type BAL expression or activity. Aberrant expression or activity includes increased or decreased expression or activity, as well as expression or activity which does not follow the wild type developmental pattern of expression or the subcellular pattern of expression. For example, aberrant BAL expression or activity is intended to include the cases in which a mutation in the BAL gene causes the BAL gene to be under-expressed or over-expressed and situations in which such mutations result in a non-functional BAL protein or a protein which does not function in a wild-type fashion, e.g., a protein which does not interact with a BAL ligand or one which interacts with a non-BAL ligand.

The assays described herein, such as the preceding diagnostic assays or the following assays, can be utilized to identify a subject having or at risk of developing a disorder associated with a misregulation in BAL protein activity or nucleic acid expression, e.g., a malignancy such as a lymphoma, e.g., non-Hodgkin's lymphoma. Alternatively, the prognostic assays can be utilized to identify a subject having or at risk for developing a disorder associated with a misregulation in BAL protein activity or nucleic acid expression, such as a e.g., a malignancy such as a lymphoma, e.g., non-Hodgkin's lymphoma. Thus, the present invention provides a method for identifying a disease or disorder associated with aberrant BAL expression or activity in which a test sample is obtained from a subject and BAL protein or nucleic acid (e.g., mRNA or genomic DNA) is detected, wherein the presence of BAL protein or nucleic acid is diagnostic for a subject having or at risk of developing a disease or disorder associated with aberrant BAL expression or activity. As used herein, a "test sample" refers to a biological sample obtained from a subject of interest. For example, a test sample can be a biological fluid (e.g., serum), cell sample, or tissue.

Furthermore, the prognostic assays described herein can be used to determine whether a subject can be administered an agent (e.g., an agonist, antagonist, peptidomimetic, protein, peptide, nucleic acid, small molecule, or other drug candidate) to treat a disease or disorder associated with aberrant BAL expression or activity. For example, such methods can be used to determine whether a subject can be effectively treated with an agent for a e.g., a malignancy such as a lymphoma, e.g., non-Hodgkin's lymphoma. Thus, the present invention provides methods for determining whether a subject can be effectively treated with an agent for a disorder associated with aberrant BAL expression or activity in which a test sample is obtained and BAL protein or nucleic acid expression or activity is detected (e.g., wherein the abundance of BAL protein or nucleic acid expression or activity is diagnostic for a subject that can be administered the agent to treat a disorder associated with aberrant BAL expression or activity).

The methods of the invention can also be used to detect genetic alterations in a BAL gene, thereby determining if a subject with the altered gene is at risk for a disorder characterized by misregulation in BAL protein activity or nucleic acid expression, such as a e.g., a malignancy such as a lymphoma, e.g., non-Hodgkin's lymphoma. In preferred embodiments, the methods include detecting, in a sample of cells from the subject, the presence or absence of a genetic alteration characterized by at least one of an alteration affecting the integrity of a gene encoding a BAL-protein, or the misexpression of the BAL gene. For example, such genetic alterations can be detected by ascertaining the existence of at least one of 1) a deletion of one or more nucleotides from a BAL gene; 2) an addition of one or more nucleotides to a BAL gene; 3) a substitution of one or more nucleotides of a BAL gene, 4) a chromosomal rearrangement of a BAL gene; 5) an alteration in the level of a messenger RNA transcript of a BAL gene, 6) aberrant modification of a BAL gene, such as of the methylation pattern of the genomic DNA, 7) the presence of a non-wild type splicing pattern of a messenger RNA transcript of a BAL gene, 8) a non-wild type level of a BAL-protein, 9) allelic loss of a BAL gene, and 10) inappropriate post-translational modification of a BAL-protein. As described herein, there are a large number of assays known in the art which can be used for detecting alterations in a BAL gene. A preferred biological sample is a tissue or serum sample isolated by conventional means from a subject.

In certain embodiments, detection of the alteration involves the use of a probe/primer in a polymerase chain reaction (PCR) (see, e.g., U.S. Pat. Nos. 4,683,195 and 4,683,202), such as anchor PCR or RACE PCR, or, alternatively, in a ligation chain reaction (LCR) (see, e.g., Landegran et al. (1988) *Science* 241:1077-1080; and Nakazawa et al. (1994) *Proc. Natl. Acad. Sci. USA* 91:360-364), the latter of which can be particularly useful for detecting point mutations in the BAL-gene (see Abravaya el al. (1995) *Nucleic Acids Res* .23:675-682). This method can include the steps of collecting a sample of cells from a subject, isolating nucleic acid (e.g., genomic DNA or mRNA) from the cells of the sample, contacting the nucleic acid sample with one or more primers which specifically hybridize to a BAL gene under conditions such that hybridization and amplification of the BAL-gene (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication (Guatelli, J. C. et al., (1990) *Proc. Natl. Acad. Sci. USA* 87:1874-1878), transcriptional amplification system (Kwoh, D. Y. et al., (1989) *Proc. Natl. Acad. Sci. USA* 86:1173-1177), Q-Beta Replicase (Lizardi, P. M. et al. (1988) *Bio-Technology* 6:1197), or any other nucleic acid amplification method, followed by the detection of the amplified molecules using techniques well known to those of skill in the art. These detection schemes are especially useful for the detection of nucleic acid molecules if such molecules are present in very low numbers.

In an alternative embodiment, mutations in a BAL gene from a sample cell can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes (see, for example, U.S. Pat. No. 5,498,531) can be used to score for the presence of specific mutations by development or loss of a ribozyme cleavage site.

In other embodiments, genetic mutations in BAL can be identified by hybridizing a sample and control nucleic acids, e.g., DNA or RNA, to high density arrays containing hundreds or thousands of oligonucleotides probes (Cronin, M. T. et al. (1996) *Human Mutation* 7: 244-255; Kozal, M. J. et al. (1996) *Nature Medicine* 2: 753-759). For example, genetic mutations in BAL can be identified in two dimensional arrays containing light-generated DNA probes as described in Cronin, M. T. et al. supra. Briefly, a first hybridization array of probes can be used to scan through long stretches of DNA in a sample and control to identify base changes between the sequences by making linear arrays of sequential overlapping probes. This step allows the identification of point mutations. This step is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the BAL gene and detect mutations by comparing the sequence of the sample BAL with the corresponding wild-type (control) sequence. Examples of sequencing reactions include those based on techniques developed by Maxam and Gilbert ((1977) *Proc. Natl Acad. Sci. USA* 74:560) or Sanger ((1977) *Proc. Natl. Acad. Sci. USA* 74:5463). It is also contemplated that any of a variety of automated sequencing procedures can be used when performing the diagnostic assays ((1995) *Biotechniques* 19:448), including sequencing by mass spectrometry (see, e.g., PCT International Publication No. WO 94/16101; Cohen et al. (1996) *Adv. Chromatogr.* 36:127-162; and Griffin et al. (1993) *Appl. Biochem. Biotechnol.* 38:147-159).

Other methods for detecting mutations in the BAL gene include methods in which protection from cleavage agents is used to detect mismatched bases in RNA/RNA or RNA/DNA heteroduplexes (Myers et al. (1985) *Science* 230:1242). In general, the art technique of "mismatch cleavage" starts by providing heteroduplexes of formed by hybridizing (labeled) RNA or DNA containing the wild-type BAL sequence with potentially mutant RNA or DNA obtained from a tissue sample. The double-stranded duplexes are treated with an agent which cleaves single-stranded regions of the duplex such as which will exist due to basepair mismatches between the control and sample strands. For instance, RNA/DNA duplexes can be treated with RNase and DNA/DNA hybrids treated with S1 nuclease to enzymatically digesting the mismatched regions. In other embodiments, either DNA/DNA or RNA/DNA duplexes can be treated with hydroxylamine or osmium tetroxide and with piperidine in order to digest mismatched regions. After digestion of the mismatched regions, the resulting material is then separated by size on denaturing polyacrylamide gels to determine the site of mutation. See, for example, Cotton el al. (1988) *Proc. Natl. Acad. Sci. USA* 85:4397; Saleeba et al. (1992) *Methods Enzymol.* 217:286-295. In a preferred embodiment, the control DNA or RNA can be labeled for detection.

In still another embodiment, the mismatch cleavage reaction employs one or more proteins that recognize mismatched base pairs in double-stranded DNA (so called "DNA mismatch repair" enzymes) in defined systems for detecting and mapping point mutations in BAL cDNAs obtained from samples of cells. For example, the mutY enzyme of *E. coli* cleaves A at G/A mismatches and the thymidine DNA glycosylase from HeLa cells cleaves T at G/T mismatches (Hsu et al. (1994) *Carcinogenesis* 15:1657-1662). According to an exemplary embodiment, a probe based on a BAL sequence, e.g., a wild-type BAL sequence, is hybridized to a cDNA or other DNA product from a test cell(s). The duplex is treated with a DNA mismatch repair enzyme, and the cleavage products, if any, can be detected from electrophoresis protocols or the like. See, for example, U.S. Pat. No. 5,459,039.

In other embodiments, alterations in electrophoretic mobility will be used to identify mutations in BAL genes. For example, single strand conformation polymorphism (SSCP) may be used to detect differences in electrophoretic mobility between mutant and wild type nucleic acids (orita et al. (1989) *Proc Natl. Acad. Sci USA:* 86:2766, see also Cotton (1993) *Mutat. Res.* 285:125-144; and Hayashi (1992) *Genet. Anal. Tech. Appl.* 9:73-79). Single-stranded DNA fragments of sample and control BAL nucleic acids will be denatured and allowed to renature. The secondary structure of single-stranded nucleic acids varies according to sequence, the resulting alteration in electrophoretic mobility enables the detection of even a single base change. The DNA fragments may be labeled or detected with labeled probes. The sensitivity of the assay may be enhanced by using RNA (rather than DNA), in which the secondary structure is more sensitive to a change in sequence. In a preferred embodiment, the subject method uses heteroduplex analysis to separate double stranded heteroduplex molecules on the basis of changes in electrophoretic mobility (Keen et al. (1991) *Trends Genet.* 7:5).

In yet another embodiment the movement of mutant or wild-type fragments in polyacrylamide gels containing a gradient of denaturant is assayed using denaturing gradient gel electrophoresis (DGGE) (Myers et al. (1985) *Nature* 313: 495). When DGGE is used as the method of analysis, DNA will be modified to insure that it does not completely denature, for example by adding a GC clamp of approximately 40 bp of high-melting GC-rich DNA by PCR. In a further embodiment, a temperature gradient is used in place of a denaturing gradient to identify differences in the mobility of control, and sample DNA (Rosenbaum and Reissner (1987) *Biophys. Chem.* 265:12753).

Examples of other techniques for detecting point mutations include but are not limited to, selective oligonucleotide hybridization, selective amplification, or selective primer extension. For example, oligonucleotide primers may be prepared in which the known mutation is placed centrally and then hybridized to target DNA under conditions which permit hybridization only if a perfect match is found (Saiki et al. (1986) *Nature* 324:163); Saiki et al. (1989) *Proc. Natl Acad. Sci. USA* 86:6230). Such allele specific oligonucleotides are hybridized to PCR amplified target DNA or a number of different mutations when the oligonucleotides are attached to the hybridizing membrane and hybridized with labeled, target DNA.

Alternatively, allele specific amplification technology which depends on selective PCR amplification may be used in conjunction with the instant invention. Oligonucleotides used as primers for specific amplification may carry the mutation of interest in the center of the molecule (so that amplification depends on differential hybridization) (Gibbs et al. (1989) *Nucleic Acids Res.* 17:2437-2448) or at the extreme 3' end of one primer where, under appropriate conditions, mismatch can prevent, or reduce polymerase extension (Prossner (1993) *Tibtech* 11:238). In addition it may be desirable to introduce a novel restriction site in the region of the mutation to create cleavage-based detection (Gasparini et al. (1992) *Mol. Cell Probes* 6:1). It is anticipated that in certain embodiments amplification may also be performed using Taq ligase for amplification (Barany (1991) *Proc. Natl. Acad. Sci USA* 88:189). In such cases, ligation will occur only if there is a perfect match at the 3' end of the 5' sequence making it possible to detect the presence of a known mutation at a specific site by looking for the presence or absence of amplification.

The methods described herein may be performed, for example, by the use of pre-packaged diagnostic kits which include at least one probe nucleic acid or antibody reagent described herein, which may be conveniently used, e.g., in clinical settings to diagnose patients exhibiting symptoms or family history of a disease or illness involving a BAL gene such as non-Hodgkin's lymphoma. Such kits can optionally include instructions for use.

Furthermore, any cell type or tissue in which BAL is expressed may be used in the prognostic assays described herein.

3. Monitoring of Effects During Clinical Trials

Monitoring the influence of agents (e.g., drugs) on the expression or activity of a BAL protein can be applied not only in basic drug screening, but also in clinical trials. For example, the effectiveness of an agent determined by a screening assay as described herein to increase BAL gene expression, protein levels, or upregulate BAL activity, can be monitored in clinical trials of subjects exhibiting decreased BAL gene expression, protein levels, or downregulated BAL activity. Alternatively, the effectiveness of an agent determined by a screening assay to decrease BAL gene expression, protein levels, or downregulate BAL activity, can be monitored in clinical trials of subjects exhibiting increased BAL gene expression, protein levels, or upregulated BAL activity. In such clinical trials, the expression or activity of a BAL gene, and preferably, other genes that have been implicated in, for example, a BAL-associated disorder can be used as a "read out" or markers of the phenotype of a particular cell.

For example, and not by way of limitation, genes, including BAL, that are modulated in cells by treatment with an agent (e.g., compound, drug or small molecule) which modulates BAL activity (e.g., identified in a screening assay as described herein) can be identified. Thus, to study the effect of agents on BAL-associated disorders (e.g., malignancies such as non-Hodgkin's lymphoma), for example, in a clinical trial, cells can be isolated and RNA prepared and analyzed for the levels of expression of BAL and other genes implicated in the BAL-associated disorder, respectively. The levels of gene expression (e.g., a gene expression pattern) can be quantified by northern blot analysis or RT-PCR, as described herein, or alternatively by measuring the amount of protein produced, by one of the methods described herein, or by measuring the levels of activity of BAL or other genes. In this way, the gene expression pattern can serve as a marker, indicative of the physiological response of the cells to the agent. Accordingly, this response state may be determined before, and at various points during treatment of the individual with the agent.

In a preferred embodiment, the present invention provides a method for monitoring the effectiveness of treatment of a subject with an agent (e.g., an agonist, antagonist, peptidomimetic, protein, peptide, nucleic acid, small molecule, or other drug candidate identified by the screening assays described herein) including the steps of (i) obtaining a pre-administration sample from a subject prior to administration of the agent; (ii) detecting the level of expression of a BAL protein, mRNA, or genomic DNA in the preadministration sample; (iii) obtaining one or more post-administration samples from the subject; (iv) detecting the level of expression or activity of the BAL protein, mRNA, or genomic DNA in the post-administration samples; (v) comparing the level of expression or activity of the BAL protein, mRNA, or genomic DNA in the pre-administration sample with the BAL protein, mRNA, or genomic DNA in the post administration sample or samples; and (vi) altering the administration of the agent to the subject accordingly. For example, increased administration of the agent may be desirable to increase expression or activity of BAL to lower levels than detected, i.e. to decrease the effectiveness of the agent. According to such an embodiment, BAL expression or activity may be used as an indicator of the effectiveness of an agent, even in the absence of an observable phenotypic response.

D. Methods of Treatment:

The present invention provides for both prophylactic and therapeutic methods of treating a subject at risk of (or susceptible to) a disorder or having a disorder associated with aberrant BAL expression or activity e.g., a malignancy such as a lymphoma, e.g., non-Hodgkin's lymphoma. With regards to both prophylactic and therapeutic methods of treatment, such treatments may be specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype") Thus, another aspect of the invention provides methods for tailoring an individual's prophylactic or therapeutic treatment with either the BAL molecules of the present invention or BAL modulators according to that individual's drug response genotype. Pharmacogenomics allows a clinician or physician to target prophylactic or therapeutic treatments to patients who will most benefit from the treatment and to avoid treatment of patients who will experience toxic drug-related side effects.

1. Prophylactic Methods

In one aspect, the invention provides a method for preventing in a subject, a disease or condition associated with an aberrant BAL expression or activity, by administering to the subject a BAL molecule or an agent which modulates BAL expression or at least one BAL activity. Subjects at risk for a disease which is caused or contributed to by aberrant BAL expression or activity can be identified by, for example, any or a combination of diagnostic or prognostic assays as described herein. Administration of a prophylactic agent can occur prior to the manifestation of symptoms characteristic of the BAL aberrancy, such that a disease or disorder is prevented or, alternatively, delayed in its progression. Depending on the type of BAL aberrancy, for example, a BAL molecule, BAL agonist, or BAL antagonist can be used to treat the subject. The appropriate agent can be determined based on, for example, the screening assays described herein.

2. Therapeutic Methods

Another aspect of the invention pertains to methods of modulating BAL expression or activity for therapeutic purposes. Accordingly, in an exemplary embodiment, the modulatory method of the invention involves contacting a cell with a BAL or agent that modulates one or more of the activities of BAL protein activity associated with the cell. An agent that modulates BAL protein activity can be an agent as described herein, such as a nucleic acid or a protein, a naturally-occurring target molecule of a BAL protein (e.g., a BAL substrate), a BAL antibody, a BAL agonist or antagonist, a peptidomimetic of a BAL agonist or antagonist, or other small molecule. In one embodiment, the agent stimulates one or more BAL activities. Examples of such stimulatory agents include active BAL protein and a nucleic acid molecule encoding BAL that has been introduced into the cell. In another embodiment, the agent inhibits one or more BAL activities. Examples of such inhibitory agents include antisense BAL nucleic acid molecules, anti-BAL antibodies, and BAL inhibitors. These modulatory methods can be performed in vitro (e.g., by culturing the cell with the agent) or, alternatively, in vivo (e.g., by administering the agent to a subject). As such, the present invention provides methods of treating an individual afflicted with a disease or disorder characterized by aberrant expression or activity of a BAL protein or nucleic acid molecule. In one embodiment, the method involves administering an agent (e.g., an agent identified by a screening assay described herein), or combination of agents that modulate (e.g., upregulate or downregulate) BAL expression or activity. In another embodiment, the method involves administering a BAL protein or nucleic acid molecule as therapy to compensate for reduced or aberrant BAL expression or activity.

Stimulation of BAL activity is desirable in situations in which BAL is abnormally downregulated and/or in which increased BAL activity is likely to have a beneficial effect. For example, stimulation of BAL activity is desirable in situations in which a BAL molecule is downregulated and/or in which increased BAL activity is likely to have a beneficial effect. Likewise, inhibition of BAL activity is desirable in situations in which BAL is abnormally upregulated and/or in which decreased BAL activity is likely to have a beneficial effect.

3. Pharmacogenomics

The BAL molecules of the present invention, as well as agents, or modulators which have a stimulatory or inhibitory effect on BAL activity (e.g., BAL gene expression) as identified by a screening assay described herein can be administered to individuals to treat (prophylactically or therapeutically) BAL-associated disorders (e.g., e.g., malignancies such as non-Hodgkin's lymphoma). In conjunction with such treatment, pharmacogenomics (i.e., the study of the relationship between an individual's genotype and that individual's response to a foreign compound or drug) may be considered. Differences in metabolism of therapeutics can lead to severe toxicity or therapeutic failure by altering the relation between dose and blood concentration of the pharmacologically active drug. Thus, a physician or clinician may consider applying knowledge obtained in relevant pharmacogenomics studies in determining whether to administer a BAL molecule or BAL modulator as well as tailoring the dosage and/or therapeutic regimen of treatment with a BAL molecule or BAL modulator.

Pharmacogenomics deals with clinically significant hereditary variations in the response to drugs due to altered drug disposition and abnormal action in affected persons. See, for example, Eichelbaum, M. et al. (1996) *Clin. Exp. Pharmacol. Physiol.* 23(10-11):983-985 and Linder, M. W. et al. (1997) *Clin. Chem.* 43(2):254-266. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (antimalarials, sulfonamides, analgesics, nitrofurans) and consumption of fava beans.

One pharmacogenomics approach to identifying genes that predict drug response, known as "a genome-wide association", relies primarily on a high-resolution map of the human genome consisting of already known gene-related markers (e.g., a "bi-allelic" gene marker map which consists of 60,000-100,000 polymorphic or variable sites on the human genome, each of which has two variants.) Such a high-resolution genetic map can be compared to a map of the genome of each of a statistically significant number of patients taking part in a Phase II/III drug trial to identify markers associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process, however, the vast majority may not be disease-associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals.

Alternatively, a method termed the "candidate gene approach", can be utilized to identify genes that predict drug response. According to this method, if a gene that encodes a drugs target is known (e.g., a BAL protein of the present invention), all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some patients do not obtain the expected drug effects or show exaggerated drug response and serious toxicity after taking the standard and safe dose of a drug. These polymorphisms are expressed in two phenotypes in the population, the extensive metabolizer (EM) and poor metabolizer (PM). The prevalence of PM is different among different populations. For example, the gene coding for CYP2D6 is highly polymorphic and several mutations have been identified in PM, which all lead to the absence of functional CYP2D6. Poor metabolizers of CYP2D6 and CYP2C19 quite frequently experience exaggerated drug response and side effects when they receive standard doses.

If a metabolite is the active therapeutic moiety, PM show no therapeutic response, as O demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification.

Alternatively, a method termed the "gene expression profiling", can be utilized to identify genes that predict drug response. For example, the gene expression of an animal dosed with a drug (e.g., a BAL molecule or BAL modulator of the present invention) can give an indication whether gene pathways related to toxicity have been turned on.

Information generated from more than one of the above pharmacogenomics approaches can be used to determine appropriate dosage and treatment regimens for prophylactic or therapeutic treatment an individual. This knowledge, when applied to dosing or drug selection, can avoid adverse reactions or therapeutic failure and thus enhance therapeutic or prophylactic efficiency when treating a subject with a BAL molecule or BAL modulator, such as a modulator identified by one of the exemplary screening assays described herein.

This invention is further illustrated by the following examples which should not be construed as limiting. The contents of all references, patents and published patent applications cited throughout this application, as well as the Figures and the Sequence Listing are incorporated herein by reference.

EXAMPLES

The following Materials and Methods were used in the Examples Described herein.

Cell Lines and Primary Tumor Specimens

Human DLB-CL cell lines DHL-4, DHL-7, DHL-8, DHL-10, HT, and the Burkitt's cell line Namalwa, were cultured in RPMI 1640 supplemented with 10% heat-inactivated fetal calf serum, 2 mM glutamine, 1 mM sodium pyruvate, 10 mM Herpes buffer and penicillin/streptomycin. Cryopreserved primary tumor specimens were obtained from DLB-CL patients with known clinical prognostic characteristics and long-term follow-up. Total RNA was isolated from the cell lines and primary tumors as described in Agular (1999) *Blood* 94(7):2403-13.

Differential Display, cDNA Cloning and Sequencing

Differential display was performed as described in Liang (1992) *Science* 257(5072):967-71, and Aguiar, *Blood* (supra). The relevant differential display product was used as a probe to screen a size-selected anti-Ig activated normal B-cell cDNA library. BAL full length cloning was completed with 5' and 3' RACE PCR, performed as described in Aguiar, *Blood* (supra). All DNA sequencing was performed and analyzed on an Applied Biosystems model 373A automated sequencer (Perkin-Elmer Corporation, Norwalk, Conn.).

Northern Blot Analysis

Total RNA from DLB-CL cell lines and primary tumors was isolated, size-fractionated in 1% Agarose/formaldehyde gels and transferred to nylon membranes as described in Aguiar, *Blood* (supra). These membranes and additional multiple tissue northern blots (Clontech, Palo Alto, Calif.) were hybridized according to standard protocols with either a differential display fragment probe, an 800 bp BAL probe (nucleotides 900 to 1700) or B-actin.

PAC Library Screening, FISH and Somatic Cell Hybrid Mapping

The human PAC library RPC11 (UK HGMP Resource Centre, Cambridge UK) was screened with a BAL cDNA probe according to standard protocols. DNA from positive clones was Southern blotted and re-probed with a distinct BAL probe to confirm the specificity of the clones. PAC DNAs were Biotin labeled, and hybridization of human normal metaphases performed as described in Fletcher (1998) *Nature Generics* 18(1):84-7. Image analysis was performed with a cooled CCD camera (Photometrics) in conjunction with an image analysis system (Oncor). A human monochromosomal somatic cell hybrid DNA panel (UK HGMP Resource Centre, Cambridge UK) was screened by PCR according to the manufacturer's instructions.

Semi-Quantitative Duplex RT-PCR cDNAs from DLB-CLs patients with known clinical prognostic characteristics and long-term follow-up and from DLB-CL cell lines were synthesized as described in Aguiar (1996) *British J. Haematol.* 95(4):673-7. To control for the quantity and quality of input cDNA and the amplification efficiency in individual test tubes, BAL cDNA was co-amplified with the constitutively expressed ABL gene. Duplex RT-PCR products were electrophoresed in 2% agarose gels, blotted and hybridized to internal BAL and ABL oligonucleotide probes. The abundance of BAL in a given sample was determined by comparing the intensity of the co-amplified PCR products with scanning densitometry. The sensitivity of the duplex RT-PCR was determined by constructing and analyzing a standard dilutional curve. In brief, fixed amounts of BAL negative and BAL positive cell line cDNAs were added to mimic BAL losses of 10%-100%. Upon co-amplification, the ratio of the intensity of the two bands plotted against the percentage of BAL "loss" yields a straight line and r2 value of 0.967, indicating the power of this system in detecting reduced BAL expression in the patient samples.

Transfections, Western Blot and Fluorescence Microscopy

Full length BAL cDNA was cloned into the green fluorescent protein (GFP) expression vector pEGFP-C (Clontech, Polo Alto, Calif.) and into the untagged expression vector pRc/CMV (Invitrogen, Carlsbad, Calif.). Linearized DNA from BAL-GFP and BAL-pRc/CMV constructs were transfected by electroporation into the Namalwa B-cell lymphoma line and selected with G418 (Sigma, St Louis, Mo.). Thereafter, the stable BAL-GFP or GFP-only bulk transfectants were sorted to select high GFP expressing cells. The pRc-CMV transfectants were cloned by limiting dilution as described in Aguiar, *Blood* (supra). Total cell lysates, membrane, cytoplasm, and nuclear fractions from multiple BAL-GFP or GFP-only transfectants were obtained and western blots performed as described in Aguiar, *Blood* (supra). Rabbit polyclonal anti-GFP anti-sera (Clontech) was used for immunological detection of BAL fusion proteins. The mouse fibroblast NIH3T3 cells were seeded on glass coverslides and transfected with BAL-GFP or GFP-alone constructs by using lipofectin (Gibco). Forty-eight hours after transfection, the slides were rinsed with ice-cold phosphate-buffered saline (PBS)-0.1% $NaN_3$, cells were fixed with 3% paraformaldehyde and analyzed by fluorescence microscopy.

Cell Migration Assays

Multiple BAL expressing stable transfectants (BAL-GFP and BAL into pRc-CMV, selected on the basis of protein expression) and vector-only controls (pEGFP and pRcCMV, respectively) were seeded overnight at $1\times10^6$ cells/ml in RPMI 10% FBS. Then, $2\times10^6$/ml cells were starved in serum-free AIM-V medium (Gibco BRL, Gaithersburg, Md.), for 1 hour at 37° C. in 5% $CO_2$. Migration assays were performed using 8μ pore filters (6.5 mm Transwell, polycarbonate membrane, Costar, Cambridge Mass.). Cell suspensions ($2\times10^5$ in 100 μL) were plated into the upper chamber, whereas 600 μL of medium with or without recombinant human SDFl-α (100 ng/mL) (R & D Systems, Minneapolis, Minn.) was added to the lower compartment. The transwells were incubated for 4 hours at 37 ° C. in 5% $CO_2$. Thereafter, cells in the lower chamber were recovered and counted (Coulter automatic cell and particle counter). All clones (with and without SDF1-α) were analyzed in duplicate and the entire assay repeated three times.

Example 1

Identification and Characterization of BAL cDNA

In this example, the identification and characterization of the genes encoding human and murine BAL is described. To identify genes which contribute to the observed differences in clinical outcome in DLB-CLs, the technique of differential display (Liang P. et al. (1992) *Science*, 257:967) was used in panels of primary tumors from patients with known clinical prognostic characteristics and mature follow-up. BAL was found to be significantly more abundant in tumors from patients with "high-risk (HR)" (International Prognostic Index, IPI) fatal disease than in tumors from cured "low risk (LR [IPI])" patients (Shipp M. et al. (1993) *N. Engl. J. Med.*, 329:987-994).

In confirmatory northern analyses, primary tumors from cured "LR" patients consistently expressed low levels of BAL whereas tumors from "HR" patients with fatal disease consistently expressed high levels of BAL (see FIG. 5). However, only 1 of 5 DLB-CL cell lines (DHL-7) expressed high levels of BAL. This observation was of particular interest because DHL-7 grows as a semi-adherent monolayer whereas BAL-negative DLB-CL cell lines grow in suspension. These findings suggest that BAL can be upregulated when DLB-CL cells interact with other cellular or extracellular components in vivo. Consistent with this hypothesis, tumors derived from a DLB-CL cell line grown in SCID mice express significantly higher levels of BAL than the parental suspension cells (see FIG. 6).

In addition to being differentially expressed in high-risk and low-risk primary DLB-CLs, BAL was expressed at higher levels in normal anti-Ig-activated splenic B-cells than in non-activated splenic B-cells (see FIG. 5). For this reason, the full length BAL cDNA was cloned by probing an Ig-activated B-cell cDNA library with the 3' BAL differential display product. Several overlapping cDNA clones were identified and 5' RACE PCR (described in, for example, Ishimaru F. et al. (1995) *Blood* 85:3199-3207) was used to complete the full length BAL cDNA sequence. Two alternatively spliced BAL cDNAs of 3243 bp (BALL) and 3138 bp (BALS) were identified. These cDNAs encode previously uncharacterized 854 aa and 819 aa proteins. In vitro translation experiments confirmed that BAL cDNAs encode ~85-87 kd proteins.

For the Bal human cDNA, two human cDNA libraries derived from anti-immunoglobulin activated splenocytes and the Raji Burkitts lymphoma cell line cloned into pCDM8 were screened to obtain additional full length Bal cDNAs.

For the Bal murine cDNAs, the BAL human sequence was used to search the mouse EST database. A 418 bp clone (Accession Number AA475710, Soares mouse mammary gland) homologous to the human sequence was identified. This sequence was used as "anchor" to several rounds of 5' and 3' RACE assays performed with mouse (Balb-c) spleen cDNA. (The sequences obtained from the EST database were used as primers).

The nucleotide sequence encoding the human BAL protein is shown in FIG. 1 and is set forth as SEQ ID NO:1. The full length protein encoded by this nucleic acid comprises about 866 amino acids and has the amino acid sequence shown in FIG. 1 and set forth as SEQ ID NO:2. The coding region (open reading frame) of SEQ ID NO:1 is set forth as SEQ ID NO:3.

The nucleotide sequence encoding the mouse BAL protein is shown in FIG. 2 and is set forth as SEQ ID NO:4. The full length protein encoded by this nucleic acid comprises about 866 amino acids and has the amino acid sequence shown in FIG. 2 and set forth as SEQ ID NO:5. The coding region (open reading frame) of SEQ ID NO:4 is set forth as SEQ ID NO:6.

Tissue Distribution of BAL

Figure 8:
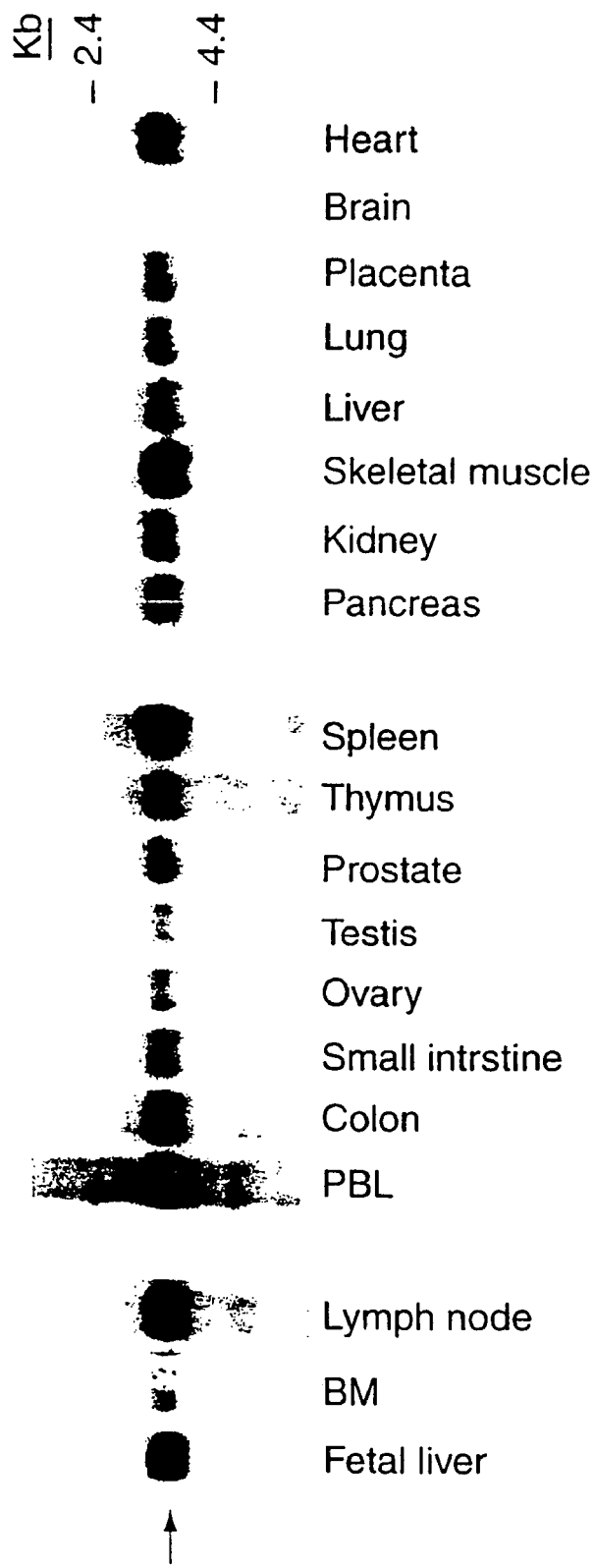
FIG. 8 depicts a northern blot analysis of BAL transcripts in multiple human tissues. BAL transcripts are most abundant in analyzed lymphoid/hematopoietic tissues (spleen, lymph node, fetal liver and peripheral blood) and several non-hematopoietic organs (heart, skeletal muscle and colon).

Although BAL transcripts were detected in the majority of organs on a multiple tissue northern blot, BAL transcripts were most abundant in lymphoid organs (spleen, lymph colon mucosa, node, fetal liver, and peripheral blood) and several additional non-hematopoietic organs (heart, skeletal muscle) (see FIG. 8).

Subcellular Localization of BAL

To determine the subcellular location of the BAL protein, the longer and the shorter BAL cDNAs ($BAL_L$ and $BAL_S$) were cloned into the green fluorescent protein (GFP) expression vector (pEGFP, Clontech) and transiently transfected in NIH3T3 fibroblasts. These fibroblasts were then examined by fluorescence microscopy. Fibroblasts were chosen for BAL subcellular localization because the lymphoma cell lines have scant cytoplasm, precluding optimal microscopic detection of subcellular structures. $BAL_S$ was found to localize to the nucleus (confirmed with western blotting of cellular subfractions) whereas $BAL_L$ localized in both the nucleus and the perinuclear cytoplasm. These data indicate that in NIH 3T3 cells, BAL does not interact directly with the cytoskeletal network, demonstrating that BAL may either influence cellular migration in an indirect manner, or may traffic between the cytoplasm and the nucleus and directly modulate cell migration via cytoskeleton interactions following specific signals.

BAL Promotes Homotypic Aggregation

In additional experiments, aggressive lymphoma cell lines were transfected with pRc-CMV-$BAL_L$ constructs and evaluated for changes in morphology. pRc-CMV-$BAL_L$ transfectants exhibited markedly increased homotypic aggregation, indicating that BAL enhances the adhesion of these cells. These observations are of particular interest because BAL was upregulated in DLB-CL tumors in SCID mice (see FIG. 6) and was significantly more abundant in primary DLB-CLs and the adherent DLB-CL cell line than in DLB-CL suspension cell lines (see FIG. 5).

Mapping of the BAL Locus

Figure 9:
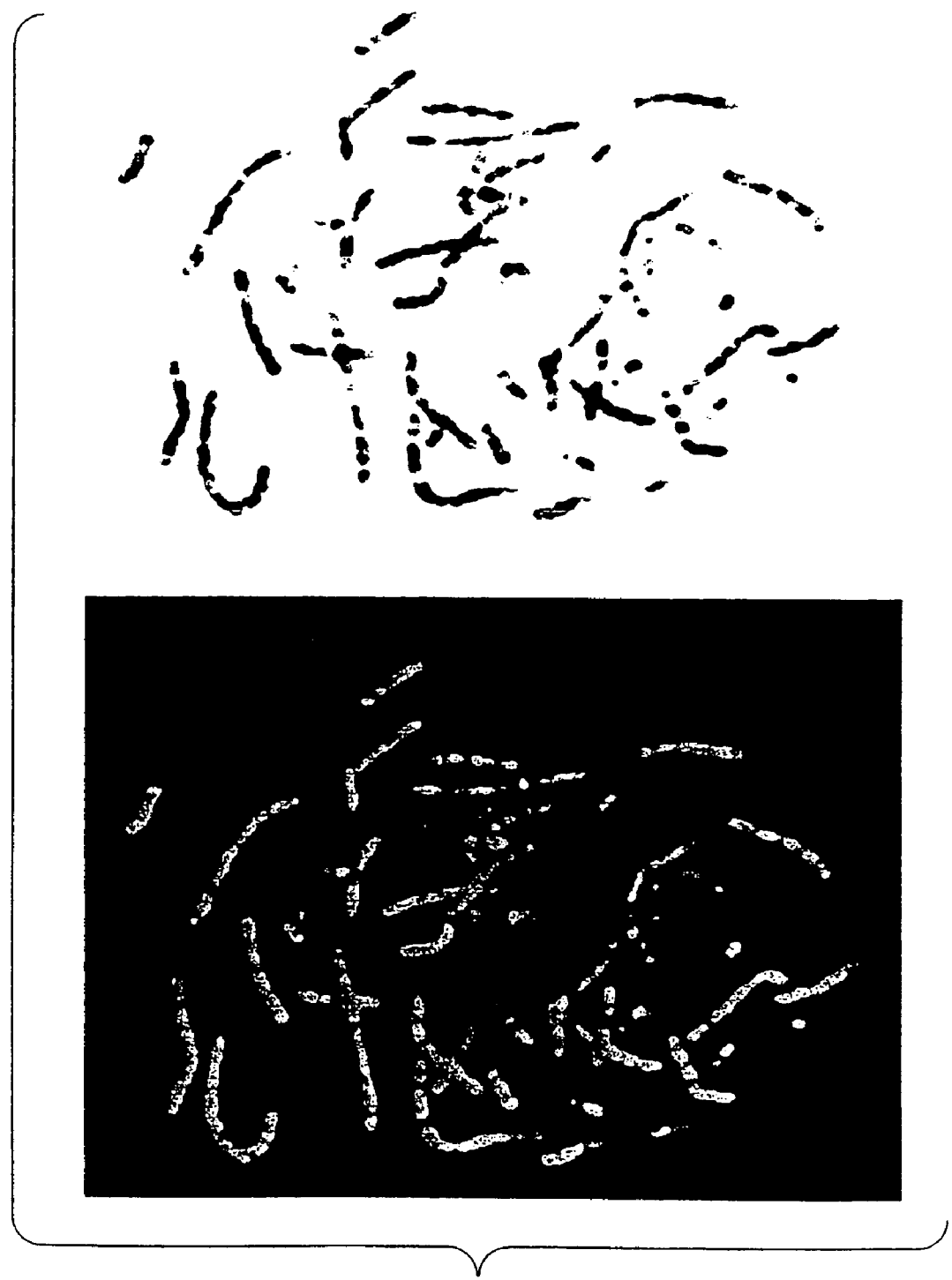
FIG. 9 depicts FISH analysis of a normal human metaphase with genomic PAC clones encompassing the BAL locus. The top panel shows the Giemsa-banded metaphase. In the FISH panel (lower), the green signals represent the BAL-PAC clones hybridized to the two normal chromosome 3q21.

To map the BAL locus, a BAL cDNA probe was used to screen a human genomic DNA PAC library (RPC11). Genomic BAL-positive PAC clones were used to perform FISH (fluorescence in situ hybridization) on normal human metaphases. In complementary experiments, a somatic cell hybrid panel was analyzed for BAL sequences. The BAL locus was mapped to chromosome 3q21 (see FIG. 9), an area of known abnormalities in multiple hematologic malignancies, including DLB-CL and other aggressive B-cell lymphomas (Cabanillas F et al. (1988) *Cancer Res.*, 48:5557-5564; Schouten H. et al. (1990) *Blood*, 75:1841; Monni O. et al. (1998), *Genes, Chrom. & Cancer*, 21:298-307; and (Mitelman F. et al. (1997) *Nat. Genet*, 15:417-474).

Analysis of the Human BAL Molecules

A BLASTP 2.0.6 search using an e-value threshold for inclusion of 0.001 and a word length of 854 letters (Altschul et al. (1990) *J. Mol. Biol.* 215:403) of the protein sequence of human BAL revealed that human BAL is similar to the histone macro-H2A.1 protein (Accession Number Q02874). The human BAL protein is 26% identical to the histone macro-H2A.1 protein (Accession Number Q02874) over amino acid residues 319-485 and 22% identical over amino acid residues 160-288.

A BLASTN 2.0.5 search using an e-value threshold for inclusion of 9e-09, score 61) and a word length of 3244 letters (Altschul et al. (1990) *J. Mol. Biol.* 215:403) of the nucleotide sequence of human BAL revealed that BAL is similar to the Soares pregnant uterus NbHPU Homo sapiens cDNA clone 502921 (Accession Number AA151346). The human BAL nucleic acid molecule is 98% identical to the Soares pregnant uterus NbHPU Homo sapiens cDNA clone 502921 (Accession Number AA151346) over nucleotides 2528 to 3132.

A BLASTP 2.0.6 search using an e-value threshold for inclusion of 0.001 and a word length of 866 letters (Altschul et al. (1990) J. Mol. Biol. 215:403) of the protein sequence of murine BAL revealed that the murine BAL is similar to the histone macro-H2A.1 protein (Accession Number Q02874). The murine BAL protein is 26% identical to the histone macro-H2A.1 protein (Accession Number Q02874) over amino acid residues 261-450 and 24% identical over amino acid residues 74-250.

A BLASTN 2.0.5 search using an e-value threshold for inclusion of 1e-08, score 60) (Altschul et al. (1990) *J. Mol. Biol.* 215:403) of the nucleotide sequence of murine BAL revealed that BAL is similar to the Soares 2NbMT *Mus musculus* cDNA clone 1446050 (Accession Number AI157103). The murine BAL nucleic acid molecule is 99% identical to the Soares 2NbMT Mus musculus cDNA clone 1446050 (Accession Number AI157103) over nucleotides 2295 to 2739.

The human BAL protein was aligned with the murine BAL protein using the ALIGN program (version 2.0), a PAM120 weight residue table, a gap length penalty of 12 and a gap penalty of 2. The results showed a 61.5% identity between the two sequences (see FIG. 3).

The human BAL nucleic acid molecule was aligned with the murine BAL nucleic acid molecule using the ALIGN program (version 2.0), a PAM120 weight residue table, a gap length penalty of 16 and a gap penalty of 4. The results showed a 71.7% identity between the two sequences (see FIG. 4).

Figure 7:
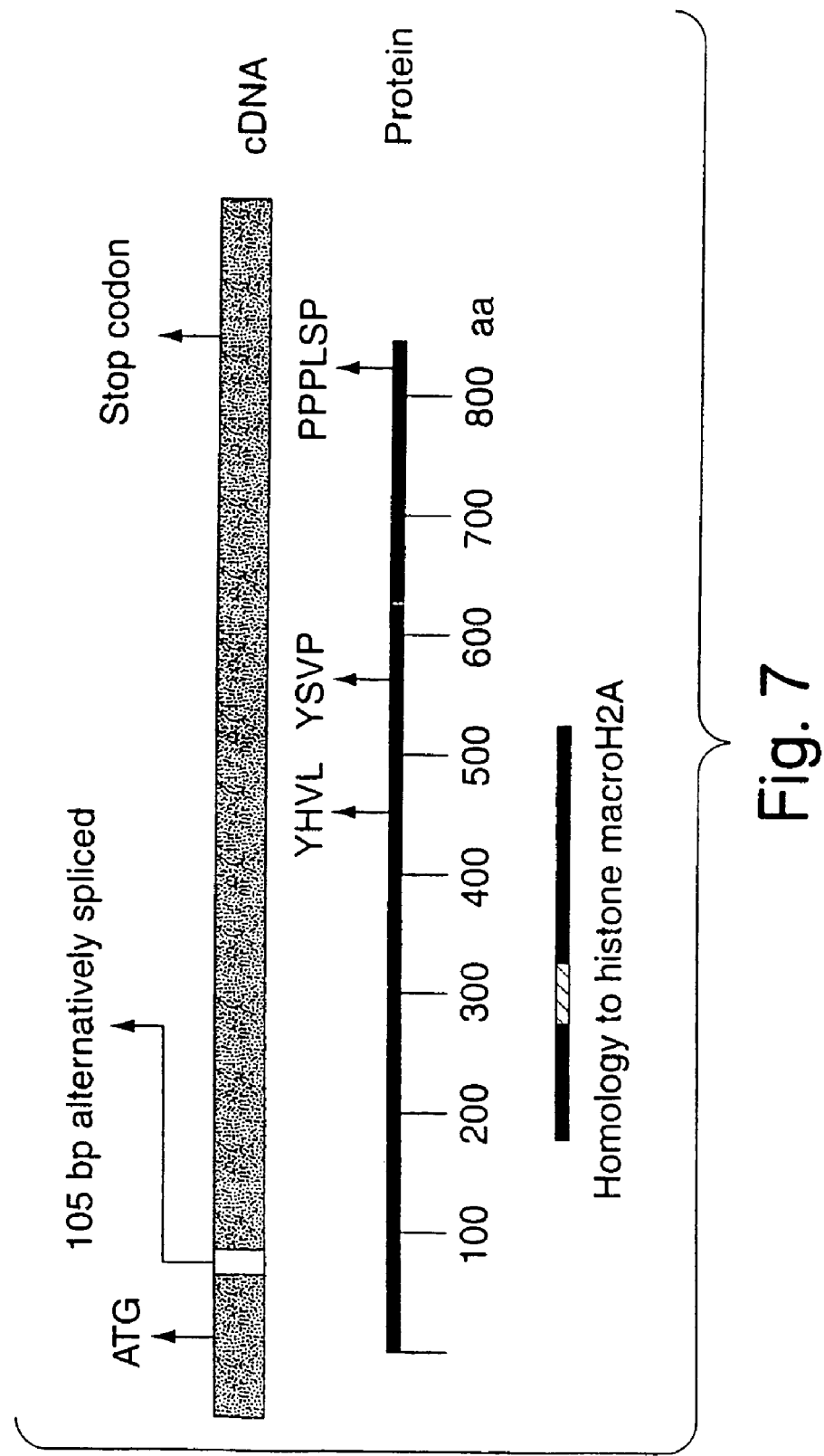
FIG. 7 depicts a diagrammatic representation of BAL cDNA and protein structure. Two alternatively spliced BAL cDNAs of 3243 bp ($BAL_L$, long) and 3138 bp ($BAL_S$, short) encode previously uncharacterized 854 aa and 819 aa proteins. The alternatively spliced region and the start and stop codons are indicated in BAL cDNA. The region of partial homology to the non-histone region of histone macroH2A and the potential CRK/CRK-1 binding sites (YHVL, YSVP) and proline-rich region are also highlighted.

Analysis of the predicted 819 as human BAL protein indicates that specific regions of human BAL have partial homology to two previously characterized domains in otherwise related proteins (FIG. 7). The human BAL N-terminal region (aa 136-256 and 335-447) contains a duplicated domain of unknown function (Pfam at the Washington University in St. Louis website) which is found in the non-histone region of histone Macro H2A, non-30 structural polyproteins of ssRNA viruses or on its own in a family of proteins from bacteria to eukaryotes (Pehrson J. R. et al. (1999) *Nucleic Acids Research* 26:2837-2842). Taken together, these data indicate that this evolutionarily conserved, as yet uncharacterized, domain is involved in an important and ubiquitous cellular process.

The human BAL C-terminal region (aa 508-709), is partially homologous to protein families (myosin heavy chain and cytoskeleton linkers ezrin-radixin-moesin [ERM]) (see FIG. 7) which primarily govern physically integrated cellular functions such as cell migration, motility, and shape, as well as cell/cell and cell/extra-cellular matrix interactions through adhesion molecules. Specifically, BAL is homologous to the rod domain (filament forming properties) of alpha and beta cardiac myosin (Warrick et al. (1987) *Annual Rev. Cell Biol.* 3 :379-421) and to the alpha-helical region of moesin, the most abundant ERM protein in lymphocytes (Bretscher (1999) *Current Biology* 8(12):721-4).

Example 2

Identification of Co-Associating Molecules and Signaling Pathways Relevant to BAL Biological Activity The following experiments are designed to confirm that: (1) BAL is phosphorylated on tyrosine; (2) BAL co-associates with other tyrosine phosphoproteins; (3) BAL specifically co-associates with CRK-L, SHP-2, P13K or ZAP70; and (4) BAL is a major component of signaling pathways in lymphohematopietic cells.

Generation of $BAL_{HA}$ and $BAL_{GRP}$ DLB-CL Transfectants $BAL_S$ and $BAL_L$ cDNAs are cloned into the GFP- and HA-tagged expression vectors (PEGFP, Clontech and pHM6, Boehringer) and transfected into pEGFP-BAL and MH6-BAL into DLB-CL cell lines that express the protein (DHL-7) or lack endogenous BAL expression (DHL-4). Both $BAL_{GFP}$ and $BAL_{HA}$ transfectants are evaluated in order to confirm BAL nuclear and perinuclear cytoplasmic localization in DLB-CLs. To characterize BAL function, $BAL_{HA}$ is preferentially used because its smaller tagged protein is more likely to retain the physiologically relevant binding sites.

Tyrosine Phosphorylation of BAL and Additional Co-associated Proteins

To confirm that BAL itself is tyrosine phosphorylated and that BAL co-associates with additional tyrosine phosphoproteins, BAL is immunoprecipitated from untreated or anti-Ig-treated DHL-7 and DHL-4 pHM6-BAL transfectants using an HA monoclonal antibody. Thereafter, the $BAL_{HA}$ immunoprecipitates are immunoblotted with a phosphotyrosine antibody, 4G10 (Upstate Biotechnology, Inc.). The molecular weights of identified tyrosine phosphoproteins are compared to that of BAL and additional candidate co-associated tyrosine phosphoproteins. In complementary experiments, $BAL_{HA}$ immunoprecipitates are blotted with specific antibodies to potential co-associating tyrosine phosphoproteins such as CRK/CRK-L, SHP-2, P13K, ZAP70 and additional candidates with molecular weights that are similar o those of identified BAL co-associated phosphoproteins. Because it may be easier to isolate co-associated proteins with concentrated highly purified recombinant BAL, the $BAL_{GST}$ fusion protein beads (described above) are also incubated with DHL-7 cell lysates, the BAL complexes are blotted, and resulting blots are probed with a phosphotyrosine antibody (4G10).

Candidate co-associating proteins can further be identified using the yeast two-hybrid system (Matchmaker Two-Hybrid System by Clontech) as described in Frederickson, R. (1998) *Curr. Opin. Biotechnol.*, 9:90-96).

Tumorigenicity of BAL Transfectants

In addition to evaluating the role of BAL in specific signaling cascades, BAL's potential effects on the local growth and distant metastasis of DLB-CL cell lines are further determined in an in vivo murine model. The above-mentioned pRc-CMV brief, parental, vector-only, pRc-CMV-$BAL_S$ and $BAL_L$ DLB-CL transfectants are injected subcutaneously or via tail vein into cohorts of SCID mice. Antisense BAL constructs can also be used because, as described herein, endogenous BAL is upregulated when the suspension DLB-CL cell lines form local tumors in vivo (see FIG. 6). Local tumorigenicity and distant metastasis can be scored at periodic intervals as described in Yakushijin Y. et al. (1998) *Blood,* 91:4282-4291.

Example 3

Figure 10:
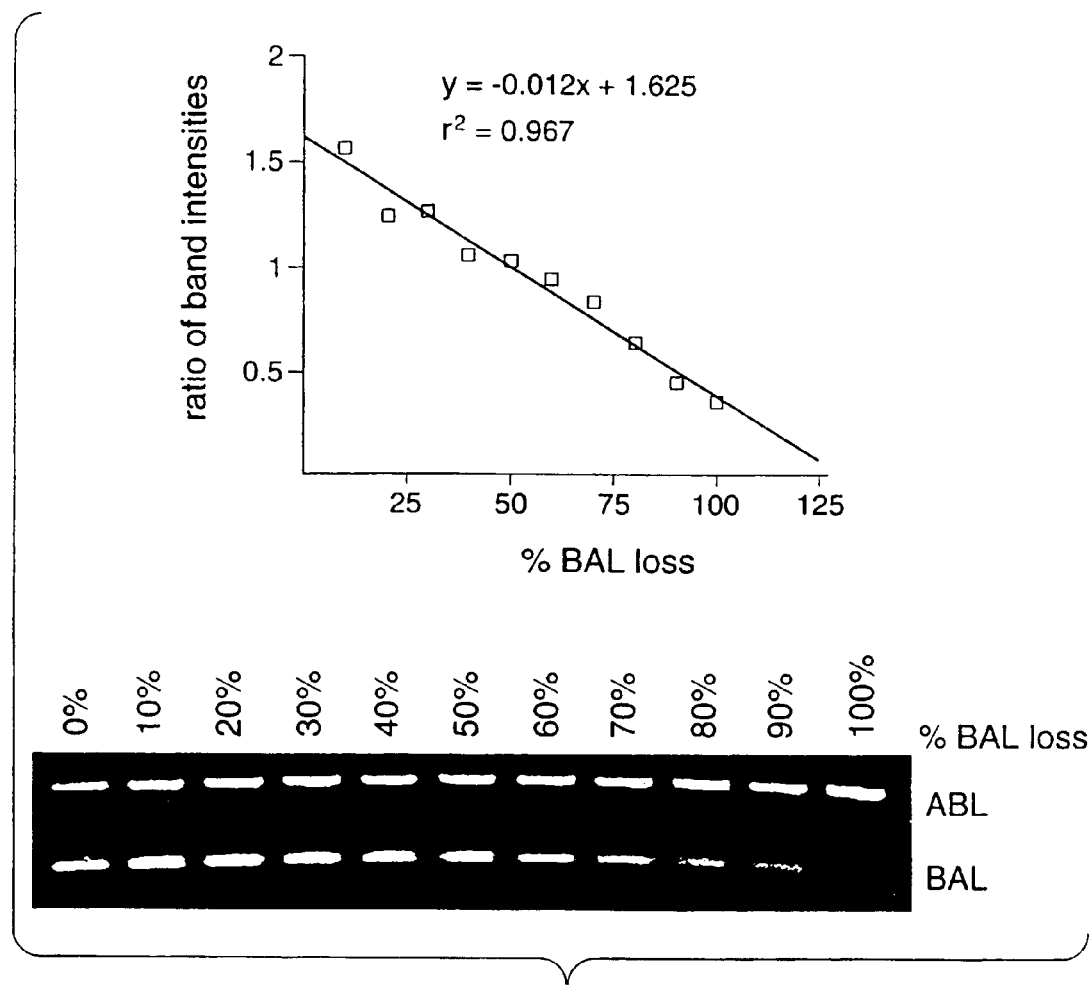
FIG. 10 depicts sensitivity of the BAL semi-quantitative duplex RT-PCR. The abundance of BAL in a given sample was determined by comparing the intensity of co-amplified BAL and control (ABL) PCR products by scanning densitometry. The sensitivity of the duplex PCR was determined by mixing fixed amounts of cDNAs from a BAL negative and a BAL positive DLB-CL cell line to mimic BAL losses of 10%-100% (lower panel). When the ratio of BAL/ABL signals was plotted against the percentage of BAL lost in a given sample, the data yield a straight line and a $r^2$ value of 0.967 (top panel).

Analysis of BAL Expression at RNA and Protein Levels in an Expanded Series of Aggressive NHLs From Well Characterized Uniformly Treated Patients Semi-Quantitative Duplex RT-PCR A semi-quantitative duplex RT-PCR assay (as described in Aguiar, R. et al. (1997) *Blood* 90 (Suppl. 1):491 a and Aguiar, R. et al. (1997) *Leukemia*, 11:233-23 8) was performed to access BAL expression in a large series of primary DLB-CLs. Briefly, the "target sequence" (BAL) was co-amplified with the constitutively expressed "control" ABL gene. The PCR products were size-fractionated, blotted and hybridized with internal BAL and ABL oligonucleotides. Autoradiogram signals were captured using a CCD camera linked to a frame grabber and intensities were quantified using the program NIH Image 1.55 (NIH, Bethesda, Md.) (as described in Aguiar, R. et al. (1997) *Leukemia*, 11:233-238). To establish the sensitivity of the assay, a series of dilutional controls were constructed by mixing fixed amounts of cDNA from the BAL-negative and BAL-positive DLB-CL cell lines. These controls mimic BAL losses at each 10% interval up to 100% (see FIG. 10). When the ratio of BAL/ABL signal was plotted against the percentage of BAL present in each of these test samples, it yielded a straight line and $r^2$ value of 0.967, confirming the sensitivity of the assay (see FIG. 10). The abundance of BAL in a given sample is determined by comparing the ratio of intensity of co-amplified BAL and ABL signals and correlating this ratio with that in the dilutional controls (as described in Aguiar, R. et al. (1997) *Blood* 90 (Suppl. 1):491a and Aguiar, R. et al. (1997) *Leukemia*, 11:233-238).

Figure 11:
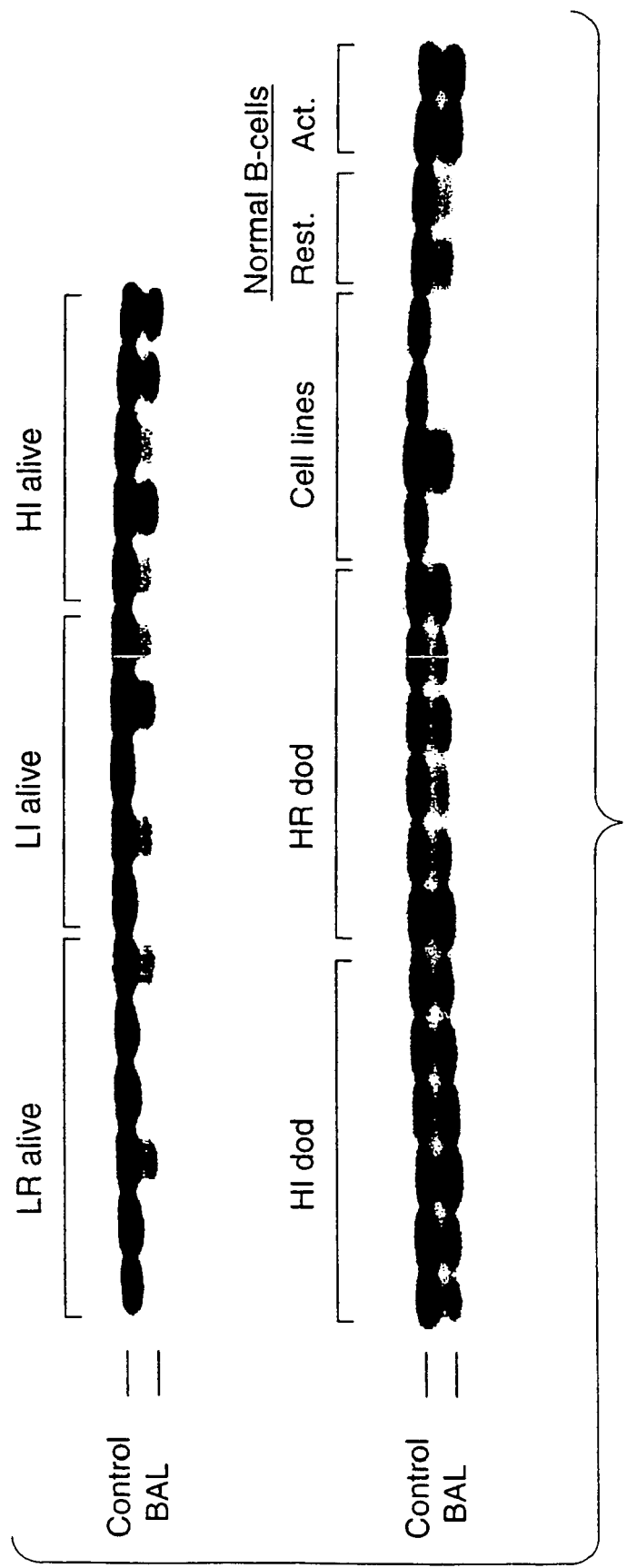
FIG. 11 depicts the results from the duplex PCR experiments.
Figure 12:
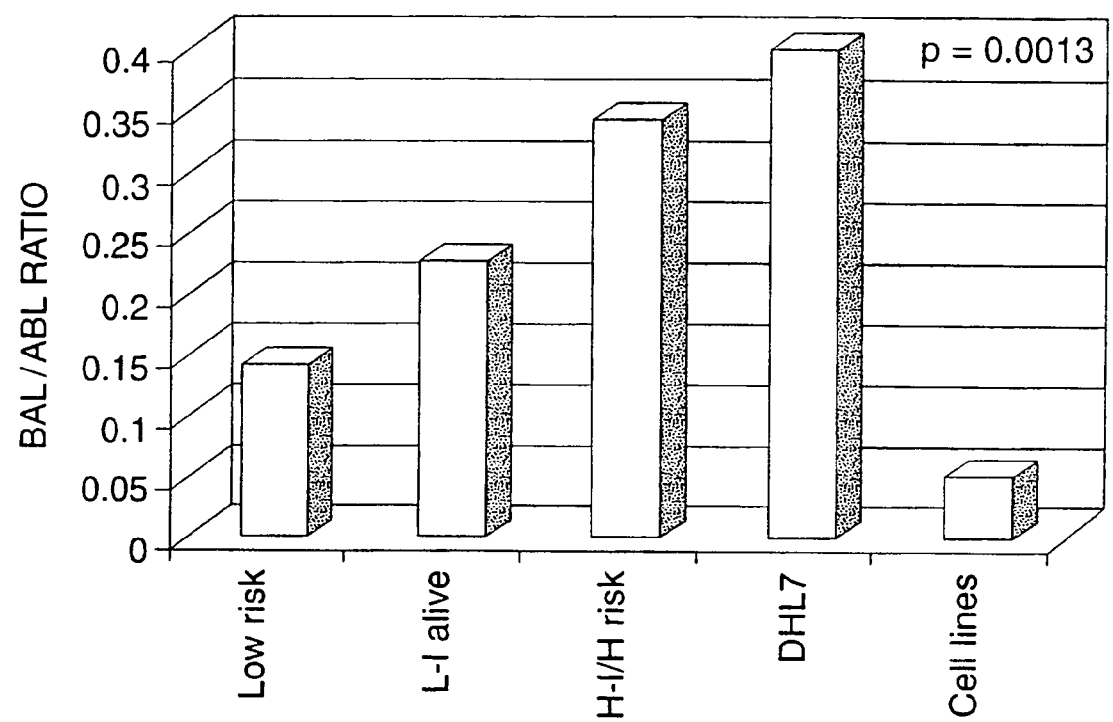
FIG. 12 is a graph depicting BAL expression as determined by the duplex PCR experiments (quantified with scanning densitometry).

To extend the initial observation regarding the risk related expression of BAL in DLBCLs, a larger series of 28 additional primary DLB-CL with well-characterized risk profiles and long term followup were studied (see FIG. 11). In these tumors, BAL expression, as determined by the ratio of the intensity of the two co-amplified cDNAs (quantified with scanning densitometry) correlated closely with the clinical risk profile (see FIG. 12). BAL transcripts were significantly more abundant in high intermediate/high risk primary DLB-CLs than in cured low and low intermediate risk tumors (p=0.0023, FIG. 12).

Development of a BAL Antibody

In order to generate a BAL antibody, the BAL cDNA was cloned into the pGEX expression vector (GST Gene Fusion System, Pharmacia). After sequencing the construct to ensure that the fusion was in frame and that no mutations had been introduced in the BAL sequence, bacterial cultures containing pGEX-BAL were treated with IPTG (isopropyl-1-Thio-b-D-Galactopyearanoside) and the GST-Bal fusion protein was induced and affinity-purified on gluthathione-S-agarose beads. Balb-c mice are immunized with the affinity-purified GST-BAL protein and their spleens harvested for generation of BAL monoclonal antibodies. Monoclonal antibodies are initially screened for reactivity with pGEX-BAL and not with pGEX alone using ELISA. Positive hybridoma supernatants are then screened against immunoblotted parental and BAL DLB-CL transfectants for reactivity with the appropriate-sized BAL protein.

Immunoperixidase Staining of Primary DLB-CLs for BAL

Immunoperoxidase staining of primary tumor specimens from a large series of well-characterized DLB-CL patients, can also be performed using the BAL monoclonal antibody produced as described above.

Example 4

Evaluation of the Integrity of the BAL Locus in Aggressive NHLs With 3q21 Abnormalities BAL maps to chromosome band 3q21, a region which is frequently associated with non-random abnormalities (gain, loss and translocations) in NHLs (Cabanillas F et al. (1988) *Cancer Res.*, 48:5557-5564); (Schouten H. et al. (1990) *Blood*, 75:1841); (Monni O. et al. (1998), *Genes, Chrom. & Cancer*, 21:298-307); and (Mitelman F. et al. (1997) *Nat. Genet*, 15:417-474). To determine whether BAL is the target of the described 3q21 abnormalities in aggressive NHLs, the integrity of the BAL locus is assessed in informative samples. The patient's metaphases are initially probed with PAC clones encompassing the BAL locus using the FISH technique (Aguiar, R. et al. (1997) *Blood*, 90:3130-3135; Carapeti, M. et al. (1998) *Blood*, 91:3127-3133; Aguiar, R. et al. (1997) *Genes, Chrom. & Cancer*, 20:408-411). In the case a translocation involving the BAL locus is detected, Southern blotting is used to map the breakpoint in BAL. Thereafter, strategies to clone the translocation partner are used including RACE PCR and, if necessary, construction and screening of patient tumor cDNA libraries with BAL probes (Aguiar, R. et al. (1997) *Blood*, 90:3130-3135 and Carapeti, M. et al. (1998) *Blood*, 91:3127-3133. If loss or gain of DNA material is found with the FISH, Southern blots are performed to confirm these findings and DNA markers flanking the BAL locus are used to delineate the smallest region of loss or gain in the tumor specimens. To define the size of the region of gain or loss of 3q21 in informative samples, candidate 3q21 YAC clones are identified from the Human Genomic Mapping Project databases (www.genome.wi.mit.edu, www.genethon.fr). Southern blot and PCR analysis of these clones' DNA maps BAL to a particular YAC (Aguiar, R. et al. (1997) *Blood* 90 (Suppl. 1):491a). Thereafter, STS markers already anchored to that particular YAC are identified in the relevant databases (www.genome.wi.mit.edu) and used as probes or PCR targets to determine their copy number in informative primary tumors as previously described (Aguiar, R. et al. (1997) *Leukemia*, 1 1:233-238). Using this strategy, the smallest region of loss or gain at 3q21 is defined, and whether BAL is the target for these structural abnormalities is determined.

Example 5

Role of BAL in Modulating Cellular Motility and Migration

Figure 13:
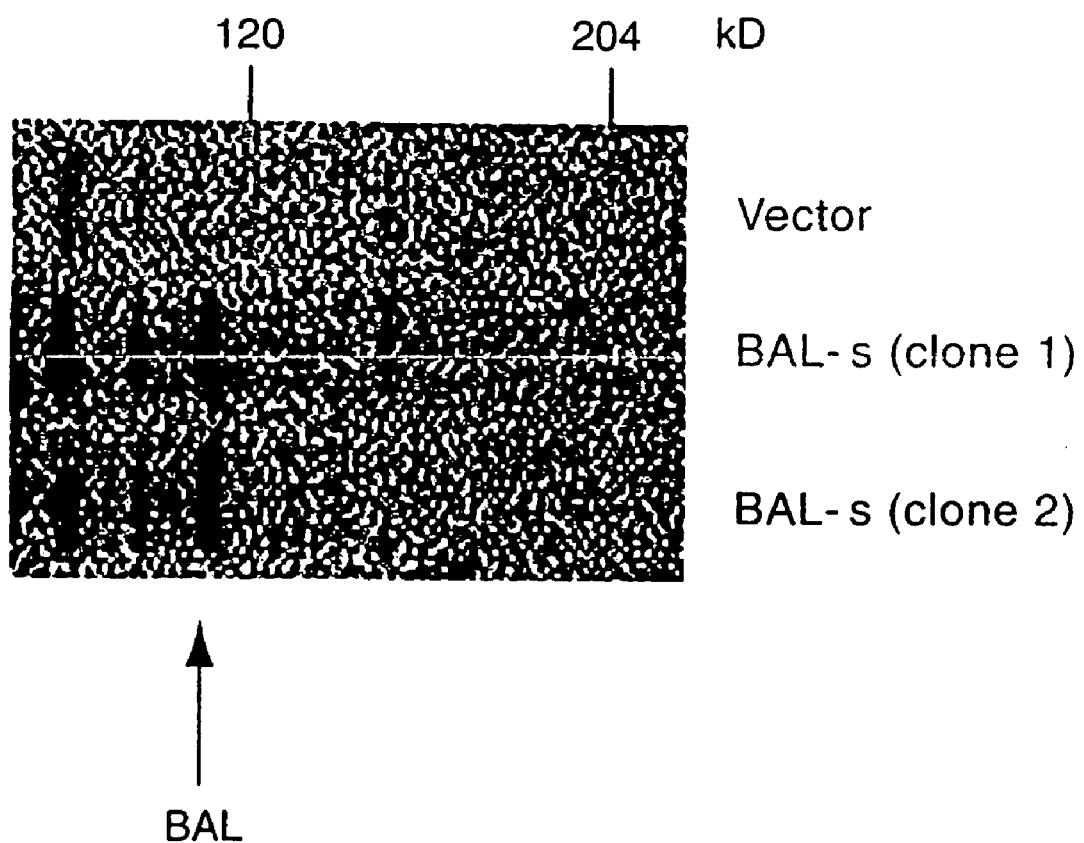
FIG. 13 depicts the results from a western blot analysis of aggressive lymphoma transfectants expressing pEGFP vector only or $pEGFP-BAL_S$.
Figure 14:
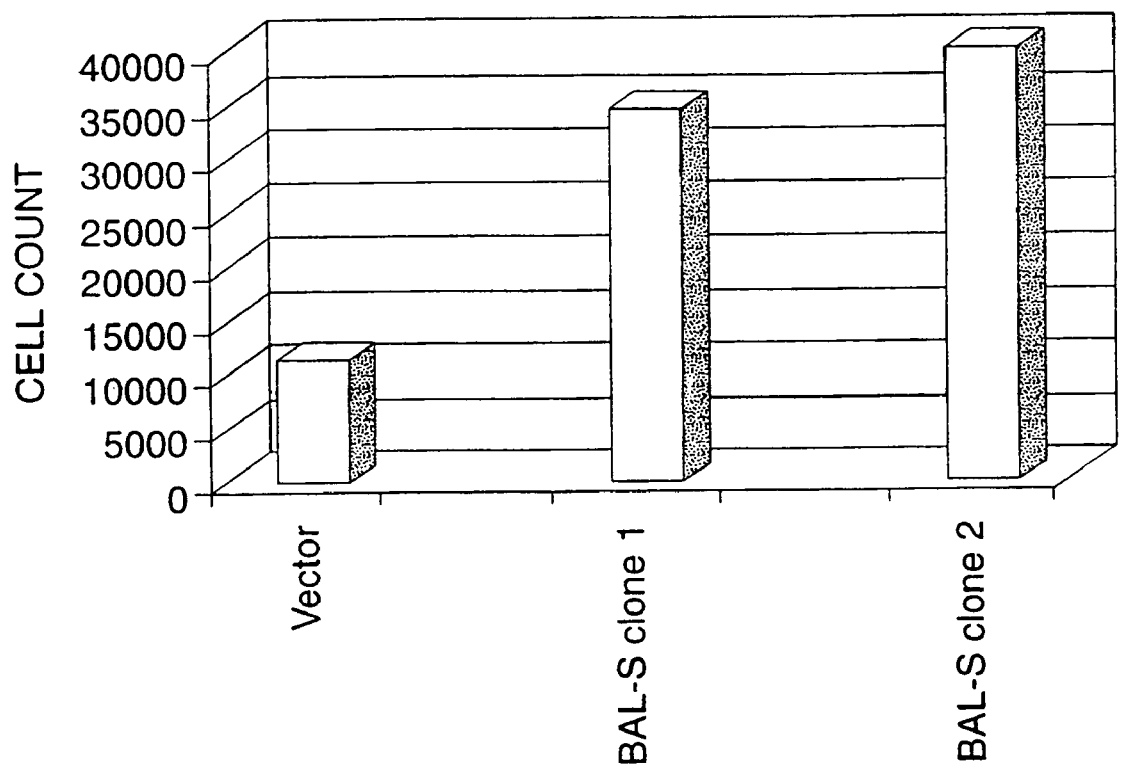
FIG. 14 is a graph depicting the cell migration of pEGFP vector only or $pEGFP-BAL_S$ transfectants.

To investigate the potential role of BAL in modulating cellular motility and migration, $BAL_S$ was cloned into a GFP vector (pEGFP) and an untagged expression vector (pRc-CMV) and pEGFP-$BAL_S$, pRc-CMV BAL, and vector only transfectants were generated in an aggressive lymphoma cell line that constitutively expresses low levels of BAL (see FIG. 13). The effects of BAL overexpression on the migration of these transfectants was investigated using a transwell system. In initial experiments, $BAL_S$-GFP or GFP-only transfectants were plated in the upper chamber and analyzed for migration to the lower chamber in the presence of the hematopoietic chemoattractant factor, stromal derived factor 1-α (SDF-1α) (see FIG. 14). In multiple independent assays, aggressive lymphoma $BAL_S$-GFP transfectants migrated at a 2-4 times higher rate than the GFP-alone transfectants (p<0.01) (see FIG. 14). Similar results were obtained with multiple BAL-$_S$pRcCMV transfectants indicating that the GFP moiety did not affect BAL function or the observed results. Taken together, these data indicate that BAL overexpression increases the migration of an aggressive NHL cell line.

Example 6

Expression of Recombinant BAL Protein in Bacterial Cells

In this example, BAL is expressed as a recombinant glutathione-S-transferase (GST) fusion polypeptide in *E. coli* and the fusion polypeptide is isolated and characterized. Specifically, BAL is fused to GST and this fusion polypeptide is expressed in *E. coli*, e.g., strain PEB199. Expression of the GST-BAL fusion protein in PEB199 is induced with IPTG. The recombinant fusion polypeptide is purified from crude bacterial lysates of the induced PEB199 strain by affinity chromatography on glutathione beads. Using polyacrylamide gel electrophoretic analysis of the polypeptide purified from the bacterial lysates, the molecular weight of the resultant fusion polypeptide is determined.

Example 7

Expression of Recombinant BAL Protein in COS Cells

To express the BAL gene in COS cells, the pcDNA/Amp vector by Invitrogen Corporation (San Diego, Calif.) is used. This vector contains an SV40 origin of replication, an ampicillin resistance gene, an *E. coli* replication origin, a CMV promoter followed by a polylinker region, and an SV40 intron and polyadenylation site. A DNA fragment encoding the entire BAL protein and an HA tag (Wilson et al. (1984) *Cell* 37:767) or a FLAG tag fused in-frame to its 3' end of the fragment is cloned into the polylinker region of the vector, thereby placing the expression of the recombinant protein under the control of the CMV promoter.

To construct the plasmid, the BAL DNA sequence is amplified by PCR using two primers. The 5' primer contains the restriction site of interest followed by approximately twenty nucleotides of the BAL coding sequence starting from the initiation codon; the 3' end sequence contains complementary sequences to the other restriction site of interest, a translation stop codon, the HA tag or FLAG tag and the last 20 nucleotides of the BAL coding sequence. The PCR amplified fragment and the pCDNA/Amp vector are digested with the appropriate restriction enzymes and the vector is dephosphorylated using the CIAP enzyme (New England Biolabs, Beverly, Mass.). Preferably the two restriction sites chosen are different so that the BAL gene is inserted in the correct orientation. The ligation mixture is transformed into *E. coli* cells (strains HB101, DH5a, SURE, available from Stratagene Cloning Systems, La Jolla, Calif., can be used), the transformed culture is plated on ampicillin media plates, and resistant colonies are selected. Plasmid DNA is isolated from transformants and examined by restriction analysis for the presence of the correct fragment.

COS cells are subsequently transfected with the BAL-pcDNA/Amp plasmid DNA using the calcium phosphate or calcium chloride co-precipitation methods, DEAE-dextran-mediated transfection, lipofection, or electroporation. Other suitable methods for transfecting host cells can be found in Sambrook, J., Fritsh, E. F., and Maniatis, T. *Molecular Cloning: A Laboratory Manual. 2nd, ed, Cold Spring Harbor Laboratory*, Cold Spring Harbor Laboratory Press, Cold Spring Harbor, N.Y., 1989. The expression of the BAL polypeptide is detected by radiolabelling ($^{35}$S-methionine or $^{35}$S-cysteine available from NEN, Boston, Mass., can be used) and immunoprecipitation (Harlow, E. and Lane, D. *Antibodies. A Laboratory Manual*, Cold Spring Harbor Laboratory Press, Cold Spring Harbor, N.Y., 1988) using an HA specific monoclonal antibody. Briefly, the cells are labelled for 8 hours with $^{35}$S-methionine (or $^{35}$S-cysteine). The culture media are then collected and the cells are lysed using detergents (RIPA buffer, 150 mM NaCl, 1% NP-40, 0.1% SDS, 0.5% DOC, 50 mM Tris, pH 7.5). Both the cell lysate and the culture media are precipitated with an HA specific monoclonal antibody. Precipitated polypeptides are then analyzed by SDS-PAGE.

Alternatively, DNA containing the BAL coding sequence is cloned directly into the polylinker of the pCDNA/Amp vector using the appropriate restriction sites. The resulting plasmid is transfected into COS cells in the manner described above, and the expression of the BAL polypeptide is detected by radiolabelling and immunoprecipitation using a BAL specific monoclonal antibody.

EQUIVALENTS

Those skilled in the art will recognize, or be able to ascertain using no more than routine experimentation, many equivalents to the specific embodiments of the invention described herein. Such equivalents are intended to be encompassed by the following claims.

What is claimed:

1. An isolated polypeptide selected from the group consisting of:
   a) a polypeptide which is encoded by SEQ ID NO: 1 or 3; and
   b) a polypeptide comprising the amino acid sequence set forth in SEQ ID NO:2.

2. The isolated polypeptide of claim 1, wherein the polypeptide is encoded SEQ ID NO: 1 or 3.

3. An isolated polypeptide selected from the group consisting of:
   a) a polypeptide which is encoded by SEQ ID NO: 4 or 6; and
   b) a polypeptide comprising the amino acid sequence set forth in SEQ ID NO:5.

4. The isolated polypeptide of claim 3, wherein the polypeptide is encoded SEQ ID NO: 4 or 6.

5. The isolated polypeptide of any one of claims 1 and 3, further comprising heterologous amino acid sequences.

6. An isolated polypeptide consisting of the amino acid sequence set forth in SEQ ID NO: 2.

7. An isolated polypeptide consisting of the amino acid sequence set forth in SEQ ID NO: 5.

* * * * *

SEQUENCE LISTING

```
<160> NUMBER OF SEQ ID NOS: 6

<210> SEQ ID NO 1
<211> LENGTH: 3243
<212> TYPE: DNA
<213> ORGANISM: Homo sapiens
<220> FEATURE:
<221> NAME/KEY: CDS
<222> LOCATION: (229)..(2790)

<400> SEQUENCE: 1
gggcttcgtg ttcctgggtg ctgaccgtgc actcccgcc gcccgaggac ttagagctct        60
ggaagtagct ctccagcttc cttcgtactc ggggggccgga cttgtacacc cgcacgagga       120
```

-continued

```
gcggggacgg cgggcgcaga agtgggccac catatctgga aactacagtc tatgctttga    180
agcgcaaaag ggaataaaca tttaaagact cccccgggga cctggagg atg gac ttt     237
                                                    Met Asp Phe
                                                    1 tcc atg gtg gcc gga gca gca gct tac aat gaa aaa tca ggt agg att     285
Ser Met Val Ala Gly Ala Ala Ala Tyr Asn Glu Lys Ser Gly Arg Ile
    5               10                  15 acc tcg ctc tca ctc ttg ttt cag aaa gtc ttt gct cag atc ttt cct     333
Thr Ser Leu Ser Leu Leu Phe Gln Lys Val Phe Ala Gln Ile Phe Pro
 20              25                  30                  35 cag tgg aga aag ggg aat aca gaa gaa tgt ctc ccc tac aag tgc tca     381
Gln Trp Arg Lys Gly Asn Thr Glu Glu Cys Leu Pro Tyr Lys Cys Ser
             40                  45                  50 gag act ggt gct ctt gga gaa aac tat agt tgg caa att ccc att aac     429
Glu Thr Gly Ala Leu Gly Glu Asn Tyr Ser Trp Gln Ile Pro Ile Asn
         55                  60                  65 cac aat gac ttc aaa att tta aaa aat aat gag cgt cag ctg tgt gaa     477
His Asn Asp Phe Lys Ile Leu Lys Asn Asn Glu Arg Gln Leu Cys Glu
     70                  75                  80 gtc ctc cag aat aag ttt ggc tgt atc tct acc ctg gtc tct cca gtt     525
Val Leu Gln Asn Lys Phe Gly Cys Ile Ser Thr Leu Val Ser Pro Val
 85                  90                  95 cag gaa ggc aac agc aaa tct ctg caa gtg ttc aga aaa atg ctg act     573
Gln Glu Gly Asn Ser Lys Ser Leu Gln Val Phe Arg Lys Met Leu Thr
100                 105                 110                 115 cct agg ata gag tta tca gtc tgg aaa gat gac ctc acc aca cat gct     621
Pro Arg Ile Glu Leu Ser Val Trp Lys Asp Asp Leu Thr Thr His Ala
                120                 125                 130 gtt gat gct gtg gtg aat gca gcc aat gaa gat ctt ctg cat ggg gga     669
Val Asp Ala Val Val Asn Ala Ala Asn Glu Asp Leu Leu His Gly Gly
            135                 140                 145 ggc ctg gcc ctg gcc ctg gta aaa gct ggt gga ttt gaa atc caa gaa     717
Gly Leu Ala Leu Ala Leu Val Lys Ala Gly Gly Phe Glu Ile Gln Glu
        150                 155                 160 gag agc aaa cag ttt gtt gcc aga tat ggt aaa gtg tca gct ggt gag     765
Glu Ser Lys Gln Phe Val Ala Arg Tyr Gly Lys Val Ser Ala Gly Glu
165                 170                 175 ata gct gtc acg gga gca ggg agg ctt ccc tgc aaa cag atc atc cat     813
Ile Ala Val Thr Gly Ala Gly Arg Leu Pro Cys Lys Gln Ile Ile His
180                 185                 190                 195 gct gtt ggg cct cgg tgg atg gaa tgg gat aaa cag gga tgt act gga     861
Ala Val Gly Pro Arg Trp Met Glu Trp Asp Lys Gln Gly Cys Thr Gly
                200                 205                 210 aag ctg cag agg gcc att gta agt att ctg aat tat gtc atc tat aaa     909
Lys Leu Gln Arg Ala Ile Val Ser Ile Leu Asn Tyr Val Ile Tyr Lys
            215                 220                 225 aat act cac att aag aca gta gca att cca gcc ttg agc tct ggg att     957
Asn Thr His Ile Lys Thr Val Ala Ile Pro Ala Leu Ser Ser Gly Ile
        230                 235                 240 ttt cag ttc cct ctg aat ttg tgt aca aag act att gta gag act atc    1005
Phe Gln Phe Pro Leu Asn Leu Cys Thr Lys Thr Ile Val Glu Thr Ile
245                 250                 255 cgg gtt agt ttg caa ggg aag cca atg atg agt aat ttg aaa gaa att    1053
Arg Val Ser Leu Gln Gly Lys Pro Met Met Ser Asn Leu Lys Glu Ile
260                 265                 270                 275 cac ctg gtg agc aat gag gac cct act gtt gct gcc ttt aaa gct gct    1101
His Leu Val Ser Asn Glu Asp Pro Thr Val Ala Ala Phe Lys Ala Ala
                280                 285                 290
```

```
tca gaa ttc atc cta ggg aag agt gag ctg gga caa gaa acc acc cct    1149
Ser Glu Phe Ile Leu Gly Lys Ser Glu Leu Gly Gln Glu Thr Thr Pro
            295                 300                 305 tct ttc aat gca atg gtc gtg aac aac ctg acc ctc cag att gtc cag    1197
Ser Phe Asn Ala Met Val Val Asn Asn Leu Thr Leu Gln Ile Val Gln
        310                 315                 320 ggc cac att gaa tgg cag acg gca gat gta att gtt aat tct gta aac    1245
Gly His Ile Glu Trp Gln Thr Ala Asp Val Ile Val Asn Ser Val Asn
    325                 330                 335 cca cat gat att aca gtt gga cct gtg gca aag tca att cta caa caa    1293
Pro His Asp Ile Thr Val Gly Pro Val Ala Lys Ser Ile Leu Gln Gln
340                 345                 350                 355 gca gga gtt gaa atg aaa tcg gaa ttt ctt gcc aca aag gct aaa cag    1341
Ala Gly Val Glu Met Lys Ser Glu Phe Leu Ala Thr Lys Ala Lys Gln
                360                 365                 370 ttt caa cgg tcc cag ttg gta ctg gtc aca aaa gga ttt aac ttg ttc    1389
Phe Gln Arg Ser Gln Leu Val Leu Val Thr Lys Gly Phe Asn Leu Phe
            375                 380                 385 tgt aaa tat ata tac cat gta ctg tgg cat tca gaa ttt cct aaa cct    1437
Cys Lys Tyr Ile Tyr His Val Leu Trp His Ser Glu Phe Pro Lys Pro
        390                 395                 400 cag ata tta aaa cat gca atg aag gag tgt ttg gaa aaa tgc att gag    1485
Gln Ile Leu Lys His Ala Met Lys Glu Cys Leu Glu Lys Cys Ile Glu
    405                 410                 415 caa aat ata act tcc att tcc ttt cct gcc ctt ggg act gga aac atg    1533
Gln Asn Ile Thr Ser Ile Ser Phe Pro Ala Leu Gly Thr Gly Asn Met
420                 425                 430                 435 gaa ata aag aag gaa aca gca gca gag att ttg ttt gat gaa gtt tta    1581
Glu Ile Lys Lys Glu Thr Ala Ala Glu Ile Leu Phe Asp Glu Val Leu
                440                 445                 450 aca ttt gcc aaa gac cat gta aaa cac cag tta act gta aaa ttt gtg    1629
Thr Phe Ala Lys Asp His Val Lys His Gln Leu Thr Val Lys Phe Val
            455                 460                 465 atc ttt cca aca gat ttg gag ata tat aag gct ttc agt tct gaa atg    1677
Ile Phe Pro Thr Asp Leu Glu Ile Tyr Lys Ala Phe Ser Ser Glu Met
        470                 475                 480 gca aag agg tcc aag atg ctg agt ttg aac aat tac agt gtc ccc cag    1725
Ala Lys Arg Ser Lys Met Leu Ser Leu Asn Asn Tyr Ser Val Pro Gln
    485                 490                 495 tca acc aga gag gag aaa aga gaa aat ggg ctt gaa gct aga tct cct    1773
Ser Thr Arg Glu Glu Lys Arg Glu Asn Gly Leu Glu Ala Arg Ser Pro
500                 505                 510                 515 gcc atc aat ctg atg gga ttc aac gtg gaa gag atg tat gag gcc cac    1821
Ala Ile Asn Leu Met Gly Phe Asn Val Glu Glu Met Tyr Glu Ala His
                520                 525                 530 gca tgg atc caa aga atc ctg agt ctc cag aac cac cac atc att gag    1869
Ala Trp Ile Gln Arg Ile Leu Ser Leu Gln Asn His His Ile Ile Glu
            535                 540                 545 aat aat cat att ctg tac ctt ggg aga aag gaa cat gac att ttg tct    1917
Asn Asn His Ile Leu Tyr Leu Gly Arg Lys Glu His Asp Ile Leu Ser
        550                 555                 560 cag ctt cag aaa act tca agt gtc tcc atc aca gaa att atc agc cca    1965
Gln Leu Gln Lys Thr Ser Ser Val Ser Ile Thr Glu Ile Ile Ser Pro
    565                 570                 575 gga agg aca gag tta gag att gaa gga gcc cgg gct gac ctc att gag    2013
Gly Arg Thr Glu Leu Glu Ile Glu Gly Ala Arg Ala Asp Leu Ile Glu
580                 585                 590                 595 gtg gtt atg aac att gaa gat atg ctt tgt aaa gta cag gag gaa atg    2061
Val Val Met Asn Ile Glu Asp Met Leu Cys Lys Val Gln Glu Glu Met
                600                 605                 610
```

```
gca agg aaa aag gag cga ggc ctt tgg cgc tcg tta gga cag tgg act    2109
Ala Arg Lys Lys Glu Arg Gly Leu Trp Arg Ser Leu Gly Gln Trp Thr
            615                 620                 625 att cag caa caa aaa acc caa gac gaa atg aaa gaa aat atc ata ttt    2157
Ile Gln Gln Gln Lys Thr Gln Asp Glu Met Lys Glu Asn Ile Ile Phe
                630                 635                 640 ctg aaa tgt cct gtg cct cca act caa gag ctt cta gat caa aag aaa    2205
Leu Lys Cys Pro Val Pro Pro Thr Gln Glu Leu Leu Asp Gln Lys Lys
645                 650                 655 cag ttt gaa aaa tgt ggt ttg cag gtt cta aag gtg gag aag ata gac    2253
Gln Phe Glu Lys Cys Gly Leu Gln Val Leu Lys Val Glu Lys Ile Asp
660                 665                 670                 675 aat gag gtc ctt atg gct gcc ttt caa aga aag aag aaa atg atg gaa    2301
Asn Glu Val Leu Met Ala Ala Phe Gln Arg Lys Lys Lys Met Met Glu
                680                 685                 690 gaa aaa ctg cac agg caa cct gtg agc cat agg ctg ttt cag caa gtc    2349
Glu Lys Leu His Arg Gln Pro Val Ser His Arg Leu Phe Gln Gln Val
            695                 700                 705 cca tac cag ttc tgc aat gtg gta tgc aga gtt ggc ttt caa aga atg    2397
Pro Tyr Gln Phe Cys Asn Val Val Cys Arg Val Gly Phe Gln Arg Met
        710                 715                 720 tac tcg aca cct tgc gat cca aaa tac gga gct ggc ata tac ttc acc    2445
Tyr Ser Thr Pro Cys Asp Pro Lys Tyr Gly Ala Gly Ile Tyr Phe Thr
725                 730                 735 aag aac ctc aaa aac ctg gca gag aag gcc aag aaa atc tct gct gca    2493
Lys Asn Leu Lys Asn Leu Ala Glu Lys Ala Lys Lys Ile Ser Ala Ala
740                 745                 750                 755 gat aag ctg atc tat gtg ttt gag gct gaa gta ctc aca ggc ttc ttc    2541
Asp Lys Leu Ile Tyr Val Phe Glu Ala Glu Val Leu Thr Gly Phe Phe
                760                 765                 770 tgc cag gga cat ccg tta aat att gtt ccc cca cca ctg agt cct gga    2589
Cys Gln Gly His Pro Leu Asn Ile Val Pro Pro Pro Leu Ser Pro Gly
            775                 780                 785 gct ata gat ggt cat gac agt gtg gtt gac aat gtc tcc agc cct gaa    2637
Ala Ile Asp Gly His Asp Ser Val Val Asp Asn Val Ser Ser Pro Glu
        790                 795                 800 acc ttt gtt att ttt agt ggc atg cag gct ata cct cag tat ttg tgg    2685
Thr Phe Val Ile Phe Ser Gly Met Gln Ala Ile Pro Gln Tyr Leu Trp
805                 810                 815 aca tgc acc cag gaa tat gta cag tca caa gat tac tca tca gga cca    2733
Thr Cys Thr Gln Glu Tyr Val Gln Ser Gln Asp Tyr Ser Ser Gly Pro
820                 825                 830                 835 atg aga ccc ttt gca cag cat cct tgg agg gga ttc gca agt ggc agc    2781
Met Arg Pro Phe Ala Gln His Pro Trp Arg Gly Phe Ala Ser Gly Ser
                840                 845                 850 cct gtt gat taatctctac atcattttaa cagctggtat ggccttacct            2830
Pro Val Asp tgggtgaact aaccaaataa tgaccatcga tggctcaaag agtggcttga atatatccca   2890
tgggttatct gtatggactg actgggttat tgaaaggact agccacatac tagcatctta   2950
gtgcctttat ctgtctttat gtcttgggt tggggtaggt agataccaaa tgaaacactt    3010
tcaggacctt ccttcctctt gcagttgttc tttaatctcc tttactagag gagataaata   3070
ttttgcatat aatgaagaaa ttttctagt atataacgca ggccttttat tttctaaaat    3130
gatgatagta taaaaatgtt aggataacag aatgatttta gattttccag agaatattat   3190
aaagtgcttt aggtatgaaa ataaatcatc tttgtctgat taaaaaaaaa aaa          3243
```

<210> SEQ ID NO 2
<211> LENGTH: 854
<212> TYPE: PRT
<213> ORGANISM: Homo sapiens

<400> SEQUENCE: 2

Met Asp Phe Ser Met Val Ala Gly Ala Ala Tyr Asn Glu Lys Ser
1               5                   10                  15

Gly Arg Ile Thr Ser Leu Ser Leu Leu Phe Gln Lys Val Phe Ala Gln
            20                  25                  30

Ile Phe Pro Gln Trp Arg Lys Gly Asn Thr Glu Glu Cys Leu Pro Tyr
        35                  40                  45

Lys Cys Ser Glu Thr Gly Ala Leu Gly Glu Asn Tyr Ser Trp Gln Ile
    50                  55                  60

Pro Ile Asn His Asn Asp Phe Lys Ile Leu Lys Asn Asn Glu Arg Gln
65                  70                  75                  80

Leu Cys Glu Val Leu Gln Asn Lys Phe Gly Cys Ile Ser Thr Leu Val
                85                  90                  95

Ser Pro Val Gln Glu Gly Asn Ser Lys Ser Leu Gln Val Phe Arg Lys
            100                 105                 110

Met Leu Thr Pro Arg Ile Glu Leu Ser Val Trp Lys Asp Asp Leu Thr
        115                 120                 125

Thr His Ala Val Asp Ala Val Asn Ala Ala Asn Glu Asp Leu Leu
    130                 135                 140

His Gly Gly Leu Ala Leu Ala Leu Val Lys Ala Gly Gly Phe Glu
145                 150                 155                 160

Ile Gln Glu Glu Ser Lys Gln Phe Val Ala Arg Tyr Gly Lys Val Ser
                165                 170                 175

Ala Gly Glu Ile Ala Val Thr Gly Ala Gly Arg Leu Pro Cys Lys Gln
            180                 185                 190

Ile Ile His Ala Val Gly Pro Arg Trp Met Glu Trp Asp Lys Gln Gly
        195                 200                 205

Cys Thr Gly Lys Leu Gln Arg Ala Ile Val Ser Ile Leu Asn Tyr Val
    210                 215                 220

Ile Tyr Lys Asn Thr His Ile Lys Thr Val Ala Ile Pro Ala Leu Ser
225                 230                 235                 240

Ser Gly Ile Phe Gln Phe Pro Leu Asn Leu Cys Thr Lys Thr Ile Val
                245                 250                 255

Glu Thr Ile Arg Val Ser Leu Gln Gly Lys Pro Met Met Ser Asn Leu
            260                 265                 270

Lys Glu Ile His Leu Val Ser Asn Glu Asp Pro Thr Val Ala Ala Phe
        275                 280                 285

Lys Ala Ala Ser Glu Phe Ile Leu Gly Lys Ser Glu Leu Gly Gln Glu
    290                 295                 300

Thr Thr Pro Ser Phe Asn Ala Met Val Val Asn Asn Leu Thr Leu Gln
305                 310                 315                 320

Ile Val Gln Gly His Ile Glu Trp Gln Thr Ala Asp Val Ile Val Asn
                325                 330                 335

Ser Val Asn Pro His Asp Ile Thr Val Gly Pro Val Ala Lys Ser Ile
            340                 345                 350

Leu Gln Gln Ala Gly Val Glu Met Lys Ser Glu Phe Leu Ala Thr Lys
        355                 360                 365

Ala Lys Gln Phe Gln Arg Ser Gln Leu Val Leu Val Thr Lys Gly Phe
    370                 375                 380

-continued

```
Asn Leu Phe Cys Lys Tyr Ile Tyr His Val Leu Trp His Ser Glu Phe
385                 390                 395                 400

Pro Lys Pro Gln Ile Leu Lys His Ala Met Lys Glu Cys Leu Glu Lys
            405                 410                 415

Cys Ile Glu Gln Asn Ile Thr Ser Ile Ser Phe Pro Ala Leu Gly Thr
        420                 425                 430

Gly Asn Met Glu Ile Lys Lys Glu Thr Ala Ala Glu Ile Leu Phe Asp
    435                 440                 445

Glu Val Leu Thr Phe Ala Lys Asp His Val Lys His Gln Leu Thr Val
450                 455                 460

Lys Phe Val Ile Phe Pro Thr Asp Leu Glu Ile Tyr Lys Ala Phe Ser
465                 470                 475                 480

Ser Glu Met Ala Lys Arg Ser Lys Met Leu Ser Leu Asn Asn Tyr Ser
            485                 490                 495

Val Pro Gln Ser Thr Arg Glu Glu Lys Arg Glu Asn Gly Leu Glu Ala
        500                 505                 510

Arg Ser Pro Ala Ile Asn Leu Met Gly Phe Asn Val Glu Glu Met Tyr
    515                 520                 525

Glu Ala His Ala Trp Ile Gln Arg Ile Leu Ser Leu Gln Asn His His
530                 535                 540

Ile Ile Glu Asn Asn His Ile Leu Tyr Leu Gly Arg Lys Glu His Asp
545                 550                 555                 560

Ile Leu Ser Gln Leu Gln Lys Thr Ser Ser Val Ser Ile Thr Glu Ile
            565                 570                 575

Ile Ser Pro Gly Arg Thr Glu Leu Glu Ile Glu Gly Ala Arg Ala Asp
        580                 585                 590

Leu Ile Glu Val Val Met Asn Ile Glu Asp Met Leu Cys Lys Val Gln
    595                 600                 605

Glu Glu Met Ala Arg Lys Lys Glu Arg Gly Leu Trp Arg Ser Leu Gly
610                 615                 620

Gln Trp Thr Ile Gln Gln Lys Thr Gln Asp Glu Met Lys Glu Asn
625                 630                 635                 640

Ile Ile Phe Leu Lys Cys Pro Val Pro Thr Gln Glu Leu Leu Asp
            645                 650                 655

Gln Lys Lys Gln Phe Glu Lys Cys Gly Leu Gln Val Leu Lys Val Glu
        660                 665                 670

Lys Ile Asp Asn Glu Val Leu Met Ala Ala Phe Gln Arg Lys Lys Lys
    675                 680                 685

Met Met Glu Glu Lys Leu His Arg Gln Pro Val Ser His Arg Leu Phe
690                 695                 700

Gln Gln Val Pro Tyr Gln Phe Cys Asn Val Val Cys Arg Val Gly Phe
705                 710                 715                 720

Gln Arg Met Tyr Ser Thr Pro Cys Asp Pro Lys Tyr Gly Ala Gly Ile
            725                 730                 735

Tyr Phe Thr Lys Asn Leu Lys Asn Leu Ala Glu Lys Ala Lys Lys Ile
        740                 745                 750

Ser Ala Ala Asp Lys Leu Ile Tyr Val Phe Glu Ala Glu Val Leu Thr
    755                 760                 765

Gly Phe Phe Cys Gln Gly His Pro Leu Asn Ile Val Pro Pro Pro Leu
770                 775                 780

Ser Pro Gly Ala Ile Asp Gly His Asp Ser Val Val Asp Asn Val Ser
785                 790                 795                 800

Ser Pro Glu Thr Phe Val Ile Phe Ser Gly Met Gln Ala Ile Pro Gln
```

-continued

```
                      805                 810                 815
    Tyr Leu Trp Thr Cys Thr Gln Glu Tyr Val Gln Ser Gln Asp Tyr Ser
                820                 825                 830

Ser Gly Pro Met Arg Pro Phe Ala Gln His Pro Trp Arg Gly Phe Ala
            835                 840                 845

Ser Gly Ser Pro Val Asp
            850

<210> SEQ ID NO 3
<211> LENGTH: 2562
<212> TYPE: DNA
<213> ORGANISM: Homo sapiens
<220> FEATURE:
<221> NAME/KEY: CDS
<222> LOCATION: (1)..(2562)

<400> SEQUENCE: 3 atg gac ttt tcc atg gtg gcc gga gca gca gct tac aat gaa aaa tca        48
Met Asp Phe Ser Met Val Ala Gly Ala Ala Ala Tyr Asn Glu Lys Ser
  1               5                  10                  15 ggt agg att acc tcg ctc tca ctc ttg ttt cag aaa gtc ttt gct cag        96
Gly Arg Ile Thr Ser Leu Ser Leu Leu Phe Gln Lys Val Phe Ala Gln
             20                  25                  30 atc ttt cct cag tgg aga aag ggg aat aca gaa gaa tgt ctc ccc tac       144
Ile Phe Pro Gln Trp Arg Lys Gly Asn Thr Glu Glu Cys Leu Pro Tyr
         35                  40                  45 aag tgc tca gag act ggt gct ctt gga gaa aac tat agt tgg caa att       192
Lys Cys Ser Glu Thr Gly Ala Leu Gly Glu Asn Tyr Ser Trp Gln Ile
     50                  55                  60 ccc att aac cac aat gac ttc aaa att tta aaa aat aat gag cgt cag       240
Pro Ile Asn His Asn Asp Phe Lys Ile Leu Lys Asn Asn Glu Arg Gln
 65                  70                  75                  80 ctg tgt gaa gtc ctc cag aat aag ttt ggc tgt atc tct acc ctg gtc       288
Leu Cys Glu Val Leu Gln Asn Lys Phe Gly Cys Ile Ser Thr Leu Val
                 85                  90                  95 tct cca gtt cag gaa ggc aac agc aaa tct ctg caa gtg ttc aga aaa       336
Ser Pro Val Gln Glu Gly Asn Ser Lys Ser Leu Gln Val Phe Arg Lys
            100                 105                 110 atg ctg act cct agg ata gag tta tca gtc tgg aaa gat gac ctc acc       384
Met Leu Thr Pro Arg Ile Glu Leu Ser Val Trp Lys Asp Asp Leu Thr
        115                 120                 125 aca cat gct gtt gat gct gtg gtg aat gca gcc aat gaa gat ctt ctg       432
Thr His Ala Val Asp Ala Val Val Asn Ala Ala Asn Glu Asp Leu Leu
    130                 135                 140 cat ggg gga ggc ctg gcc ctg gcc ctg gta aaa gct ggt gga ttt gaa       480
His Gly Gly Gly Leu Ala Leu Ala Leu Val Lys Ala Gly Gly Phe Glu
145                 150                 155                 160 atc caa gaa gag agc aaa cag ttt gtt gcc aga tat ggt aaa gtg tca       528
Ile Gln Glu Glu Ser Lys Gln Phe Val Ala Arg Tyr Gly Lys Val Ser
                165                 170                 175 gct ggt gag ata gct gtc acg gga gca ggg agg ctt ccc tgc aaa cag       576
Ala Gly Glu Ile Ala Val Thr Gly Ala Gly Arg Leu Pro Cys Lys Gln
            180                 185                 190 atc atc cat gct gtt ggg cct cgg tgg atg gaa tgg gat aaa cag gga       624
Ile Ile His Ala Val Gly Pro Arg Trp Met Glu Trp Asp Lys Gln Gly
        195                 200                 205 tgt act gga aag ctg cag agg gcc att gta agt att ctg aat tat gtc       672
Cys Thr Gly Lys Leu Gln Arg Ala Ile Val Ser Ile Leu Asn Tyr Val
    210                 215                 220 atc tat aaa aat act cac att aag aca gta gca att cca gcc ttg agc       720
```

```
                                                                -continued

Ile Tyr Lys Asn Thr His Ile Lys Thr Val Ala Ile Pro Ala Leu Ser
225                 230                 235                 240 tct ggg att ttt cag ttc cct ctg aat ttg tgt aca aag act att gta           768
Ser Gly Ile Phe Gln Phe Pro Leu Asn Leu Cys Thr Lys Thr Ile Val
                245                 250                 255 gag act atc cgg gtt agt ttg caa ggg aag cca atg atg agt aat ttg           816
Glu Thr Ile Arg Val Ser Leu Gln Gly Lys Pro Met Met Ser Asn Leu
260                 265                 270 aaa gaa att cac ctg gtg agc aat gag gac cct act gtt gct gcc ttt           864
Lys Glu Ile His Leu Val Ser Asn Glu Asp Pro Thr Val Ala Ala Phe
            275                 280                 285 aaa gct gct tca gaa ttc atc cta ggg aag agt gag ctg gga caa gaa           912
Lys Ala Ala Ser Glu Phe Ile Leu Gly Lys Ser Glu Leu Gly Gln Glu
        290                 295                 300 acc acc cct tct ttc aat gca atg gtc gtg aac aac ctg acc ctc cag           960
Thr Thr Pro Ser Phe Asn Ala Met Val Val Asn Asn Leu Thr Leu Gln
305                 310                 315                 320 att gtc cag ggc cac att gaa tgg cag acg gca gat gta att gtt aat          1008
Ile Val Gln Gly His Ile Glu Trp Gln Thr Ala Asp Val Ile Val Asn
                325                 330                 335 tct gta aac cca cat gat att aca gtt gga cct gtg gca aag tca att          1056
Ser Val Asn Pro His Asp Ile Thr Val Gly Pro Val Ala Lys Ser Ile
                340                 345                 350 cta caa caa gca gga gtt gaa atg aaa tcg gaa ttt ctt gcc aca aag          1104
Leu Gln Gln Ala Gly Val Glu Met Lys Ser Glu Phe Leu Ala Thr Lys
            355                 360                 365 gct aaa cag ttt caa cgg tcc cag ttg gta ctg gtc aca aaa gga ttt          1152
Ala Lys Gln Phe Gln Arg Ser Gln Leu Val Leu Val Thr Lys Gly Phe
370                 375                 380 aac ttg ttc tgt aaa tat ata tac cat gta ctg tgg cat tca gaa ttt          1200
Asn Leu Phe Cys Lys Tyr Ile Tyr His Val Leu Trp His Ser Glu Phe
385                 390                 395                 400 cct aaa cct cag ata tta aaa cat gca atg aag gag tgt ttg gaa aaa          1248
Pro Lys Pro Gln Ile Leu Lys His Ala Met Lys Glu Cys Leu Glu Lys
                405                 410                 415 tgc att gag caa aat ata act tcc att tcc ttt cct gcc ctt ggg act          1296
Cys Ile Glu Gln Asn Ile Thr Ser Ile Ser Phe Pro Ala Leu Gly Thr
                420                 425                 430 gga aac atg gaa ata aag aag gaa aca gca gca gag att ttg ttt gat          1344
Gly Asn Met Glu Ile Lys Lys Glu Thr Ala Ala Glu Ile Leu Phe Asp
            435                 440                 445 gaa gtt tta aca ttt gcc aaa gac cat gta aaa cac cag tta act gta          1392
Glu Val Leu Thr Phe Ala Lys Asp His Val Lys His Gln Leu Thr Val
        450                 455                 460 aaa ttt gtg atc ttt cca aca gat ttg gag ata tat aag gct ttc agt          1440
Lys Phe Val Ile Phe Pro Thr Asp Leu Glu Ile Tyr Lys Ala Phe Ser
465                 470                 475                 480 tct gaa atg gca aag agg tcc aag atg ctg agt ttg aac aat tac agt          1488
Ser Glu Met Ala Lys Arg Ser Lys Met Leu Ser Leu Asn Asn Tyr Ser
                485                 490                 495 gtc ccc cag tca acc aga gag gag aaa aga gaa aat ggg ctt gaa gct          1536
Val Pro Gln Ser Thr Arg Glu Glu Lys Arg Glu Asn Gly Leu Glu Ala
                500                 505                 510 aga tct cct gcc atc aat ctg atg gga ttc aac gtg gaa gag atg tat          1584
Arg Ser Pro Ala Ile Asn Leu Met Gly Phe Asn Val Glu Glu Met Tyr
            515                 520                 525 gag gcc cac gca tgg atc caa aga atc ctg agt ctc cag aac cac cac          1632
Glu Ala His Ala Trp Ile Gln Arg Ile Leu Ser Leu Gln Asn His His
        530                 535                 540
```

```
atc att gag aat aat cat att ctg tac ctt ggg aga aag gaa cat gac       1680
Ile Ile Glu Asn Asn His Ile Leu Tyr Leu Gly Arg Lys Glu His Asp
545                 550                 555                 560 att ttg tct cag ctt cag aaa act tca agt gtc tcc atc aca gaa att       1728
Ile Leu Ser Gln Leu Gln Lys Thr Ser Ser Val Ser Ile Thr Glu Ile
                565                 570                 575 atc agc cca gga agg aca gag tta gag att gaa gga gcc cgg gct gac       1776
Ile Ser Pro Gly Arg Thr Glu Leu Glu Ile Glu Gly Ala Arg Ala Asp
            580                 585                 590 ctc att gag gtg gtt atg aac att gaa gat atg ctt tgt aaa gta cag       1824
Leu Ile Glu Val Val Met Asn Ile Glu Asp Met Leu Cys Lys Val Gln
        595                 600                 605 gag gaa atg gca agg aaa aag gag cga ggc ctt tgg cgc tcg tta gga       1872
Glu Glu Met Ala Arg Lys Lys Glu Arg Gly Leu Trp Arg Ser Leu Gly
610                 615                 620 cag tgg act att cag caa caa aaa acc caa gac gaa atg aaa gaa aat       1920
Gln Trp Thr Ile Gln Gln Gln Lys Thr Gln Asp Glu Met Lys Glu Asn
625                 630                 635                 640 atc ata ttt ctg aaa tgt cct gtg cct cca act caa gag ctt cta gat       1968
Ile Ile Phe Leu Lys Cys Pro Val Pro Pro Thr Gln Glu Leu Leu Asp
                645                 650                 655 caa aag aaa cag ttt gaa aaa tgt ggt ttg cag gtt cta aag gtg gag       2016
Gln Lys Lys Gln Phe Glu Lys Cys Gly Leu Gln Val Leu Lys Val Glu
            660                 665                 670 aag ata gac aat gag gtc ctt atg gct gcc ttt caa aga aag aag aaa       2064
Lys Ile Asp Asn Glu Val Leu Met Ala Ala Phe Gln Arg Lys Lys Lys
        675                 680                 685 atg atg gaa gaa aaa ctg cac agg caa cct gtg agc cat agg ctg ttt       2112
Met Met Glu Glu Lys Leu His Arg Gln Pro Val Ser His Arg Leu Phe
690                 695                 700 cag caa gtc cca tac cag ttc tgc aat gtg gta tgc aga gtt ggc ttt       2160
Gln Gln Val Pro Tyr Gln Phe Cys Asn Val Val Cys Arg Val Gly Phe
705                 710                 715                 720 caa aga atg tac tcg aca cct tgc gat cca aaa tac gga gct ggc ata       2208
Gln Arg Met Tyr Ser Thr Pro Cys Asp Pro Lys Tyr Gly Ala Gly Ile
                725                 730                 735 tac ttc acc aag aac ctc aaa aac ctg gca gag aag gcc aag aaa atc       2256
Tyr Phe Thr Lys Asn Leu Lys Asn Leu Ala Glu Lys Ala Lys Lys Ile
            740                 745                 750 tct gct gca gat aag ctg atc tat gtg ttt gag gct gaa gta ctc aca       2304
Ser Ala Ala Asp Lys Leu Ile Tyr Val Phe Glu Ala Glu Val Leu Thr
        755                 760                 765 ggc ttc ttc tgc cag gga cat ccg tta aat att gtt ccc cca cca ctg       2352
Gly Phe Phe Cys Gln Gly His Pro Leu Asn Ile Val Pro Pro Pro Leu
770                 775                 780 agt cct gga gct ata gat ggt cat gac agt gtg gtt gac aat gtc tcc       2400
Ser Pro Gly Ala Ile Asp Gly His Asp Ser Val Val Asp Asn Val Ser
785                 790                 795                 800 agc cct gaa acc ttt gtt att ttt agt ggc atg cag gct ata cct cag       2448
Ser Pro Glu Thr Phe Val Ile Phe Ser Gly Met Gln Ala Ile Pro Gln
                805                 810                 815 tat ttg tgg aca tgc acc cag gaa tat gta cag tca caa gat tac tca       2496
Tyr Leu Trp Thr Cys Thr Gln Glu Tyr Val Gln Ser Gln Asp Tyr Ser
            820                 825                 830 tca gga cca atg aga ccc ttt gca cag cat cct tgg agg gga ttc gca       2544
Ser Gly Pro Met Arg Pro Phe Ala Gln His Pro Trp Arg Gly Phe Ala
        835                 840                 845 agt ggc agc cct gtt gat                                               2562
Ser Gly Ser Pro Val Asp
850
```

```
<210> SEQ ID NO 4
<211> LENGTH: 3024
<212> TYPE: DNA
<213> ORGANISM: Murinae gen. sp.
<220> FEATURE:
<221> NAME/KEY: CDS
<222> LOCATION: (171)..(2648)

<400> SEQUENCE: 4
aggaacggaa gtttggcggg aacccggatt cccaggttca ggcctctcaa gggtggagcg      60
gaatagaggg aaacaggcca ccatctcctc gatctacaga ctacacttgg aaacacaaac    120
aaatataaat atctgaagac ccacgtggga cctgaagaat ggcctattac atg gat      176
                                                          Met Asp
                                                            1 aca tgg gcg gca gct ccc gcc gaa aga cca gcc aac aat tct ctt gaa      224
Thr Trp Ala Ala Ala Pro Ala Glu Arg Pro Ala Asn Asn Ser Leu Glu
        5                  10                  15 gaa cat tat aga tgg caa att ccc att aaa cac aat gtc ttc gaa att      272
Glu His Tyr Arg Trp Gln Ile Pro Ile Lys His Asn Val Phe Glu Ile
 20                  25                  30 tta aag agc aat gag agt cag cta tgt gaa gtc ctc caa aat aag ttt      320
Leu Lys Ser Asn Glu Ser Gln Leu Cys Glu Val Leu Gln Asn Lys Phe
 35                  40                  45                  50 gga tgc atc tct acc ctg agc tgt cca act cta gca ggg agc agc tct      368
Gly Cys Ile Ser Thr Leu Ser Cys Pro Thr Leu Ala Gly Ser Ser Ser
             55                  60                  65 cct gct cag aga gtc ttc aga agg acc ctg atc cct ggg ata gag tta      416
Pro Ala Gln Arg Val Phe Arg Arg Thr Leu Ile Pro Gly Ile Glu Leu
         70                  75                  80 tct gtc tgg aag gat gac ctt acc aga cac gtt gtt gat gct gtg gtg      464
Ser Val Trp Lys Asp Asp Leu Thr Arg His Val Val Asp Ala Val Val
     85                  90                  95 aac gca gcc aat gaa aac ctt ttg cat gga agt ggc ctg gcc gga agc      512
Asn Ala Ala Asn Glu Asn Leu Leu His Gly Ser Gly Leu Ala Gly Ser
100                 105                 110 ttg gtg aaa act ggt ggc ttt gaa atc caa gaa gag agc aaa aga atc      560
Leu Val Lys Thr Gly Gly Phe Glu Ile Gln Glu Glu Ser Lys Arg Ile
115                 120                 125                 130 att gcc aac gtt ggt aaa atc tca gtt ggt gga atc gct atc acc ggt      608
Ile Ala Asn Val Gly Lys Ile Ser Val Gly Gly Ile Ala Ile Thr Gly
                135                 140                 145 gcg ggg aga ctt cct tgc cat ttg att atc cat gcg gtt gga cct cgg      656
Ala Gly Arg Leu Pro Cys His Leu Ile Ile His Ala Val Gly Pro Arg
            150                 155                 160 tgg aca gtt acg aac agc cag aca gct atc gaa tta ctg aaa ttt gcc      704
Trp Thr Val Thr Asn Ser Gln Thr Ala Ile Glu Leu Leu Lys Phe Ala
        165                 170                 175 att agg aac att cta gat tat gtc acc aaa tat gat cta cgc att aag      752
Ile Arg Asn Ile Leu Asp Tyr Val Thr Lys Tyr Asp Leu Arg Ile Lys
    180                 185                 190 aca gta gca att cca gcc ctg agc tct gga att ttc cag ttc cct ctg      800
Thr Val Ala Ile Pro Ala Leu Ser Ser Gly Ile Phe Gln Phe Pro Leu
195                 200                 205                 210 gat ttg tgt aca agc ata att tta gaa act atc cgg ctt tat ttc caa      848
Asp Leu Cys Thr Ser Ile Ile Leu Glu Thr Ile Arg Leu Tyr Phe Gln
                215                 220                 225 gac aag caa atg ttc ggt aat ttg aga gag att cat ctg gtg agc aat      896
Asp Lys Gln Met Phe Gly Asn Leu Arg Glu Ile His Leu Val Ser Asn
            230                 235                 240
```

```
gag gac ccc act gtt gcg tcc ttt aaa tcc gcc tca gaa agc atc cta      944
Glu Asp Pro Thr Val Ala Ser Phe Lys Ser Ala Ser Glu Ser Ile Leu
        245                 250                 255 ggg agg gac ctg agc tct tgg ggg ggt cca gaa act gac cct gct tcc      992
Gly Arg Asp Leu Ser Ser Trp Gly Gly Pro Glu Thr Asp Pro Ala Ser
260                 265                 270 acc atg act ctt cgc atc ggc cgg ggc ctg act ctc cag att gtc caa     1040
Thr Met Thr Leu Arg Ile Gly Arg Gly Leu Thr Leu Gln Ile Val Gln
275                 280                 285                 290 ggc tgt att gaa atg caa aca aca gat gta att ggt aat tct gga tac     1088
Gly Cys Ile Glu Met Gln Thr Thr Asp Val Ile Gly Asn Ser Gly Tyr
                295                 300                 305 atg cag gat ttt aaa tca gga cga gtg gca cag tcg att ctt aga caa     1136
Met Gln Asp Phe Lys Ser Gly Arg Val Ala Gln Ser Ile Leu Arg Gln
            310                 315                 320 gca ggg gtt gaa atg gaa aag gaa ctt gac aag gtt aac ctg tcc aca     1184
Ala Gly Val Glu Met Glu Lys Glu Leu Asp Lys Val Asn Leu Ser Thr
        325                 330                 335 gat tat caa gag gtg tgg gtc aca aaa gga ttt aaa ttg tcc tgt cag     1232
Asp Tyr Gln Glu Val Trp Val Thr Lys Gly Phe Lys Leu Ser Cys Gln
340                 345                 350 tat gtc ttc cat gtg gca tgg cat tcc caa atc aac aaa tac cag ata     1280
Tyr Val Phe His Val Ala Trp His Ser Gln Ile Asn Lys Tyr Gln Ile
355                 360                 365                 370 ttg aaa gat gca atg aag tcc tgt cta gaa aaa tgc ctt aaa cca gat     1328
Leu Lys Asp Ala Met Lys Ser Cys Leu Glu Lys Cys Leu Lys Pro Asp
                375                 380                 385 ata aat tcc att tcc ttt cct gct ctc ggg aca gga ttg atg gat ttg     1376
Ile Asn Ser Ile Ser Phe Pro Ala Leu Gly Thr Gly Leu Met Asp Leu
            390                 395                 400 aag aag agt aca gca gct cag ata atg ttt gag gaa gtt ttt gca ttt     1424
Lys Lys Ser Thr Ala Ala Gln Ile Met Phe Glu Glu Val Phe Ala Phe
        405                 410                 415 gct aaa gag cac aag gaa aaa acg cta act gta aag att gtg atc ttt     1472
Ala Lys Glu His Lys Glu Lys Thr Leu Thr Val Lys Ile Val Ile Phe
420                 425                 430 cca gta gat gtg gag acg tac aag att ttt tat gct gaa atg aca aaa     1520
Pro Val Asp Val Glu Thr Tyr Lys Ile Phe Tyr Ala Glu Met Thr Lys
435                 440                 445                 450 agg tcc aac gag ctg aat ctc agc ggt aat agt ggt gct tta gcc ctg     1568
Arg Ser Asn Glu Leu Asn Leu Ser Gly Asn Ser Gly Ala Leu Ala Leu
                455                 460                 465 cag tgg tcc agt ggg gag caa aga aga ggc ggc ctt gaa gct gga tct     1616
Gln Trp Ser Ser Gly Glu Gln Arg Arg Gly Gly Leu Glu Ala Gly Ser
            470                 475                 480 cct gcc atc aat ctc atg ggt gta aaa gtg gga gag atg tgt gag gcc     1664
Pro Ala Ile Asn Leu Met Gly Val Lys Val Gly Glu Met Cys Glu Ala
        485                 490                 495 cag gaa tgg att gaa agg ttg ctg gtc tcc ctg gac cac cac atc att     1712
Gln Glu Trp Ile Glu Arg Leu Leu Val Ser Leu Asp His His Ile Ile
500                 505                 510 gag aat aat cat att ctc tat ctt ggg aaa aaa gag cac gac gtg ctg     1760
Glu Asn Asn His Ile Leu Tyr Leu Gly Lys Lys Glu His Asp Val Leu
515                 520                 525                 530 tct gag ctc cag acc agc aca aga gtc tcc att tca gag act gtc agt     1808
Ser Glu Leu Gln Thr Ser Thr Arg Val Ser Ile Ser Glu Thr Val Ser
                535                 540                 545 cca aga acg gcc act ttg gag att aaa ggt ccc cag gct gac ctc att     1856
Pro Arg Thr Ala Thr Leu Glu Ile Lys Gly Pro Gln Ala Asp Leu Ile
```

-continued

```
              550              555              560
gac gca gtt atg agg att gaa tgt atg ctg tgt gac gtt cag gaa gaa     1904
Asp Ala Val Met Arg Ile Glu Cys Met Leu Cys Asp Val Gln Glu Glu
        565              570              575 gtg gca gga aaa agg gag aaa aat ctt tgg agc ttg tca gga cag ggg     1952
Val Ala Gly Lys Arg Glu Lys Asn Leu Trp Ser Leu Ser Gly Gln Gly
580              585              590 acc aac cag caa gaa aaa ctg gat aaa atg gaa gaa tcg tac aca ttt     2000
Thr Asn Gln Gln Glu Lys Leu Asp Lys Met Glu Glu Ser Tyr Thr Phe
595              600              605              610 caa cga tac cca gca tca tta act cag gaa ctt cag gac cga aag aaa     2048
Gln Arg Tyr Pro Ala Ser Leu Thr Gln Glu Leu Gln Asp Arg Lys Lys
            615              620              625 cag ttt gaa aag tgt ggc ttg tgg gtt gtg cag gtg gag cag ata gac     2096
Gln Phe Glu Lys Cys Gly Leu Trp Val Val Gln Val Glu Gln Ile Asp
        630              635              640 aat aag gtg ctg ctg gct gcc ttc caa gag aag aag aaa atg atg gaa     2144
Asn Lys Val Leu Leu Ala Ala Phe Gln Glu Lys Lys Lys Met Met Glu
        645              650              655 gag agg acg cca aag gga tct ggg agc caa agg ttg ttt cag cag gtc     2192
Glu Arg Thr Pro Lys Gly Ser Gly Ser Gln Arg Leu Phe Gln Gln Val
    660              665              670 cca cat cag ttc tgc aat acg gtg tgc aga gtc ggc ttc cac aga atg     2240
Pro His Gln Phe Cys Asn Thr Val Cys Arg Val Gly Phe His Arg Met
675              680              685              690 tat tcg aca tcc tat aac cca gtt tat gga gcc ggc ata tat ttc acc     2288
Tyr Ser Thr Ser Tyr Asn Pro Val Tyr Gly Ala Gly Ile Tyr Phe Thr
            695              700              705 aag agc ctc aaa aat cta gca gac aag gtc aag aaa acc tca agc aca     2336
Lys Ser Leu Lys Asn Leu Ala Asp Lys Val Lys Lys Thr Ser Ser Thr
        710              715              720 gac aag cta atc tat gtg ttt gag gca gaa gta ctc aca ggg tcc ttc     2384
Asp Lys Leu Ile Tyr Val Phe Glu Ala Glu Val Leu Thr Gly Ser Phe
    725              730              735 tgt cag ggt aat tcc tca aat atc atc cct cca cca ttg agt cct ggg     2432
Cys Gln Gly Asn Ser Ser Asn Ile Ile Pro Pro Pro Leu Ser Pro Gly
740              745              750 gcc tta gat gtc aat gac agc gta gtt gac aat gtt tcc agc cct gaa     2480
Ala Leu Asp Val Asn Asp Ser Val Val Asp Asn Val Ser Ser Pro Glu
755              760              765              770 acc att gtt gtt ttt aat ggc atg cag gcc atg ccc ctg tac ttg tgg     2528
Thr Ile Val Val Phe Asn Gly Met Gln Ala Met Pro Leu Tyr Leu Trp
            775              780              785 act tgc aca cag gat agg aca ttc tca cag cat ccg atg tgg tca cag     2576
Thr Cys Thr Gln Asp Arg Thr Phe Ser Gln His Pro Met Trp Ser Gln
        790              795              800 gac tac tca tca gga cca gga atg gtc tct tcg ctg cag tcc tgg gaa     2624
Asp Tyr Ser Ser Gly Pro Gly Met Val Ser Ser Leu Gln Ser Trp Glu
    805              810              815 tgg gtc tta aat ggc agc tct gtt tagtgtctac atcagtttaa caagcagaag    2678
Trp Val Leu Asn Gly Ser Ser Val
820              825 gggttgagag aactgacaaa atgataaata acaggttacc tgttcagaat gatggggtca   2738
ctaaaggcac cgaccacaca ctagcatcat agtgcctttg tctttacctc tgggcttgac   2798
tgggcagatg ccagctaaaa cttcctcact gtcttttcta tttgacatct ttcatctcct   2858
ttcctatagg tgcacagcaag aatactttat atagaacaag gatatttttt tcaagcctgt  2918
tattttctaa aatgatagca caaactagga caacaggatg atttcaggtt ttctatataa   2978
```
tttataaagt gctttggata tccaaataaa tcacctttgt ctgagt 3024

<210> SEQ ID NO 5
<211> LENGTH: 826
<212> TYPE: PRT
<213> ORGANISM: Murinae gen. sp.

<400> SEQUENCE: 5

Met Asp Thr Trp Ala Ala Pro Ala Glu Arg Pro Ala Asn Asn Ser
1               5                   10                  15

Leu Glu Glu His Tyr Arg Trp Gln Ile Pro Ile Lys His Asn Val Phe
            20                  25                  30

Glu Ile Leu Lys Ser Asn Glu Ser Gln Leu Cys Glu Val Leu Gln Asn
        35                  40                  45

Lys Phe Gly Cys Ile Ser Thr Leu Ser Cys Pro Thr Leu Ala Gly Ser
    50                  55                  60

Ser Ser Pro Ala Gln Arg Val Phe Arg Arg Thr Leu Ile Pro Gly Ile
65                  70                  75                  80

Glu Leu Ser Val Trp Lys Asp Asp Leu Thr Arg His Val Val Asp Ala
                85                  90                  95

Val Val Asn Ala Ala Asn Glu Asn Leu Leu His Gly Ser Gly Leu Ala
            100                 105                 110

Gly Ser Leu Val Lys Thr Gly Gly Phe Glu Ile Gln Glu Glu Ser Lys
        115                 120                 125

Arg Ile Ile Ala Asn Val Gly Lys Ile Ser Val Gly Gly Ile Ala Ile
    130                 135                 140

Thr Gly Ala Gly Arg Leu Pro Cys His Leu Ile Ile His Ala Val Gly
145                 150                 155                 160

Pro Arg Trp Thr Val Thr Asn Ser Gln Thr Ala Ile Glu Leu Leu Lys
                165                 170                 175

Phe Ala Ile Arg Asn Ile Leu Asp Tyr Val Thr Lys Tyr Asp Leu Arg
            180                 185                 190

Ile Lys Thr Val Ala Ile Pro Ala Leu Ser Ser Gly Ile Phe Gln Phe
        195                 200                 205

Pro Leu Asp Leu Cys Thr Ser Ile Ile Leu Glu Thr Ile Arg Leu Tyr
    210                 215                 220

Phe Gln Asp Lys Gln Met Phe Gly Asn Leu Arg Glu Ile His Leu Val
225                 230                 235                 240

Ser Asn Glu Asp Pro Thr Val Ala Ser Phe Lys Ser Ala Ser Glu Ser
                245                 250                 255

Ile Leu Gly Arg Asp Leu Ser Ser Trp Gly Gly Pro Glu Thr Asp Pro
            260                 265                 270

Ala Ser Thr Met Thr Leu Arg Ile Gly Arg Gly Leu Thr Leu Gln Ile
        275                 280                 285

Val Gln Gly Cys Ile Glu Met Gln Thr Thr Asp Val Ile Gly Asn Ser
    290                 295                 300

Gly Tyr Met Gln Asp Phe Lys Ser Gly Arg Val Ala Gln Ser Ile Leu
305                 310                 315                 320

Arg Gln Ala Gly Val Glu Met Glu Lys Glu Leu Asp Lys Val Asn Leu
                325                 330                 335

Ser Thr Asp Tyr Gln Glu Val Trp Val Thr Lys Gly Phe Lys Leu Ser
            340                 345                 350

Cys Gln Tyr Val Phe His Val Ala Trp His Ser Gln Ile Asn Lys Tyr
        355                 360                 365

```
Gln Ile Leu Lys Asp Ala Met Lys Ser Cys Leu Glu Lys Cys Leu Lys
    370                 375                 380
Pro Asp Ile Asn Ser Ile Ser Phe Pro Ala Leu Gly Thr Gly Leu Met
385                 390                 395                 400
Asp Leu Lys Lys Ser Thr Ala Ala Gln Ile Met Phe Glu Glu Val Phe
                405                 410                 415
Ala Phe Ala Lys Glu His Lys Glu Lys Thr Leu Thr Val Lys Ile Val
            420                 425                 430
Ile Phe Pro Val Asp Val Glu Thr Tyr Lys Ile Phe Tyr Ala Glu Met
        435                 440                 445
Thr Lys Arg Ser Asn Glu Leu Asn Leu Ser Gly Asn Ser Gly Ala Leu
    450                 455                 460
Ala Leu Gln Trp Ser Ser Gly Glu Gln Arg Gly Gly Leu Glu Ala
465                 470                 475                 480
Gly Ser Pro Ala Ile Asn Leu Met Gly Val Lys Val Gly Glu Met Cys
                485                 490                 495
Glu Ala Gln Glu Trp Ile Glu Arg Leu Leu Val Ser Leu Asp His His
            500                 505                 510
Ile Ile Glu Asn Asn His Ile Leu Tyr Leu Gly Lys Lys Glu His Asp
        515                 520                 525
Val Leu Ser Glu Leu Gln Thr Ser Thr Arg Val Ser Ile Ser Glu Thr
    530                 535                 540
Val Ser Pro Arg Thr Ala Thr Leu Glu Ile Lys Gly Pro Gln Ala Asp
545                 550                 555                 560
Leu Ile Asp Ala Val Met Arg Ile Glu Cys Met Leu Cys Asp Val Gln
                565                 570                 575
Glu Glu Val Ala Gly Lys Arg Glu Lys Asn Leu Trp Ser Leu Ser Gly
            580                 585                 590
Gln Gly Thr Asn Gln Gln Glu Lys Leu Asp Lys Met Glu Glu Ser Tyr
        595                 600                 605
Thr Phe Gln Arg Tyr Pro Ala Ser Leu Thr Gln Glu Leu Gln Asp Arg
    610                 615                 620
Lys Lys Gln Phe Glu Lys Cys Gly Leu Trp Val Gln Val Glu Gln
625                 630                 635                 640
Ile Asp Asn Lys Val Leu Leu Ala Ala Phe Gln Glu Lys Lys Met
                645                 650                 655
Met Glu Glu Arg Thr Pro Lys Gly Ser Gly Ser Gln Arg Leu Phe Gln
            660                 665                 670
Gln Val Pro His Gln Phe Cys Asn Thr Val Cys Arg Val Gly Phe His
        675                 680                 685
Arg Met Tyr Ser Thr Ser Tyr Asn Pro Val Tyr Gly Ala Gly Ile Tyr
    690                 695                 700
Phe Thr Lys Ser Leu Lys Asn Leu Ala Asp Lys Val Lys Lys Thr Ser
705                 710                 715                 720
Ser Thr Asp Lys Leu Ile Tyr Val Phe Glu Ala Glu Val Leu Thr Gly
                725                 730                 735
Ser Phe Cys Gln Gly Asn Ser Ser Asn Ile Ile Pro Pro Leu Ser
            740                 745                 750
Pro Gly Ala Leu Asp Val Asn Asp Ser Val Val Asp Asn Val Ser Ser
        755                 760                 765
Pro Glu Thr Ile Val Val Phe Asn Gly Met Gln Ala Met Pro Leu Tyr
    770                 775                 780
```

```
Leu Trp Thr Cys Thr Gln Asp Arg Thr Phe Ser Gln His Pro Met Trp
785                 790                 795                 800

Ser Gln Asp Tyr Ser Ser Gly Pro Gly Met Val Ser Ser Leu Gln Ser
            805                 810                 815

Trp Glu Trp Val Leu Asn Gly Ser Ser Val
        820                 825

<210> SEQ ID NO 6
<211> LENGTH: 2478
<212> TYPE: DNA
<213> ORGANISM: Murinae gen. sp.
<220> FEATURE:
<221> NAME/KEY: CDS
<222> LOCATION: (1)..(2478)

<400> SEQUENCE: 6 atg gat aca tgg gcg gca gct ccc gcc gaa aga cca gcc aac aat tct       48
Met Asp Thr Trp Ala Ala Ala Pro Ala Glu Arg Pro Ala Asn Asn Ser
 1               5                  10                  15 ctt gaa gaa cat tat aga tgg caa att ccc att aaa cac aat gtc ttc       96
Leu Glu Glu His Tyr Arg Trp Gln Ile Pro Ile Lys His Asn Val Phe
             20                  25                  30 gaa att tta aag agc aat gag agt cag cta tgt gaa gtc ctc caa aat      144
Glu Ile Leu Lys Ser Asn Glu Ser Gln Leu Cys Glu Val Leu Gln Asn
         35                  40                  45 aag ttt gga tgc atc tct acc ctg agc tgt cca act cta gca ggg agc      192
Lys Phe Gly Cys Ile Ser Thr Leu Ser Cys Pro Thr Leu Ala Gly Ser
     50                  55                  60 agc tct cct gct cag aga gtc ttc aga agg acc ctg atc cct ggg ata      240
Ser Ser Pro Ala Gln Arg Val Phe Arg Arg Thr Leu Ile Pro Gly Ile
 65                  70                  75                  80 gag tta tct gtc tgg aag gat gac ctt acc aga cac gtt gtt gat gct      288
Glu Leu Ser Val Trp Lys Asp Asp Leu Thr Arg His Val Val Asp Ala
                 85                  90                  95 gtg gtg aac gca gcc aat gaa aac ctt ttg cat gga agt ggc ctg gcc      336
Val Val Asn Ala Ala Asn Glu Asn Leu Leu His Gly Ser Gly Leu Ala
            100                 105                 110 gga agc ttg gtg aaa act ggt ggc ttt gaa atc caa gaa gag agc aaa      384
Gly Ser Leu Val Lys Thr Gly Gly Phe Glu Ile Gln Glu Glu Ser Lys
        115                 120                 125 aga atc att gcc aac gtt ggt aaa atc tca gtt ggt gga atc gct atc      432
Arg Ile Ile Ala Asn Val Gly Lys Ile Ser Val Gly Gly Ile Ala Ile
    130                 135                 140 acc ggt gcg ggg aga ctt cct tgc cat ttg att atc cat gcg gtt gga      480
Thr Gly Ala Gly Arg Leu Pro Cys His Leu Ile Ile His Ala Val Gly
145                 150                 155                 160 cct cgg tgg aca gtt acg aac agc cag aca gct atc gaa tta ctg aaa      528
Pro Arg Trp Thr Val Thr Asn Ser Gln Thr Ala Ile Glu Leu Leu Lys
                165                 170                 175 ttt gcc att agg aac att cta gat tat gtc acc aaa tat gat cta cgc      576
Phe Ala Ile Arg Asn Ile Leu Asp Tyr Val Thr Lys Tyr Asp Leu Arg
            180                 185                 190 att aag aca gta gca att cca gcc ctg agc tct gga att ttc cag ttc      624
Ile Lys Thr Val Ala Ile Pro Ala Leu Ser Ser Gly Ile Phe Gln Phe
        195                 200                 205 cct ctg gat ttg tgt aca agc ata att tta gaa act atc cgg ctt tat      672
Pro Leu Asp Leu Cys Thr Ser Ile Ile Leu Glu Thr Ile Arg Leu Tyr
    210                 215                 220 ttc caa gac aag caa atg ttc ggt aat ttg aga gag att cat ctg gtg      720
Phe Gln Asp Lys Gln Met Phe Gly Asn Leu Arg Glu Ile His Leu Val
225                 230                 235                 240
```

```
agc aat gag gac ccc act gtt gcg tcc ttt aaa tcc gcc tca gaa agc      768
Ser Asn Glu Asp Pro Thr Val Ala Ser Phe Lys Ser Ala Ser Glu Ser
            245                 250                 255 atc cta ggg agg gac ctg agc tct tgg ggg ggt cca gaa act gac cct      816
Ile Leu Gly Arg Asp Leu Ser Ser Trp Gly Gly Pro Glu Thr Asp Pro
        260                 265                 270 gct tcc acc atg act ctt cgc atc ggc cgg ggc ctg act ctc cag att      864
Ala Ser Thr Met Thr Leu Arg Ile Gly Arg Gly Leu Thr Leu Gln Ile
    275                 280                 285 gtc caa ggc tgt att gaa atg caa aca aca gat gta att ggt aat tct      912
Val Gln Gly Cys Ile Glu Met Gln Thr Thr Asp Val Ile Gly Asn Ser
290                 295                 300 gga tac atg cag gat ttt aaa tca gga cga gtg gca cag tcg att ctt      960
Gly Tyr Met Gln Asp Phe Lys Ser Gly Arg Val Ala Gln Ser Ile Leu
305                 310                 315                 320 aga caa gca ggg gtt gaa atg gaa aag gaa ctt gac aag gtt aac ctg     1008
Arg Gln Ala Gly Val Glu Met Glu Lys Glu Leu Asp Lys Val Asn Leu
            325                 330                 335 tcc aca gat tat caa gag gtg tgg gtc aca aaa gga ttt aaa ttg tcc     1056
Ser Thr Asp Tyr Gln Glu Val Trp Val Thr Lys Gly Phe Lys Leu Ser
        340                 345                 350 tgt cag tat gtc ttc cat gtg gca tgg cat tcc caa atc aac aaa tac     1104
Cys Gln Tyr Val Phe His Val Ala Trp His Ser Gln Ile Asn Lys Tyr
    355                 360                 365 cag ata ttg aaa gat gca atg aag tcc tgt cta gaa aaa tgc ctt aaa     1152
Gln Ile Leu Lys Asp Ala Met Lys Ser Cys Leu Glu Lys Cys Leu Lys
370                 375                 380 cca gat ata aat tcc att tcc ttt cct gct ctc ggg aca gga ttg atg     1200
Pro Asp Ile Asn Ser Ile Ser Phe Pro Ala Leu Gly Thr Gly Leu Met
385                 390                 395                 400 gat ttg aag aag agt aca gca gct cag ata atg ttt gag gaa gtt ttt     1248
Asp Leu Lys Lys Ser Thr Ala Ala Gln Ile Met Phe Glu Glu Val Phe
            405                 410                 415 gca ttt gct aaa gag cac aag gaa aaa acg cta act gta aag att gtg     1296
Ala Phe Ala Lys Glu His Lys Glu Lys Thr Leu Thr Val Lys Ile Val
        420                 425                 430 atc ttt cca gta gat gtg gag acg tac aag att ttt tat gct gaa atg     1344
Ile Phe Pro Val Asp Val Glu Thr Tyr Lys Ile Phe Tyr Ala Glu Met
    435                 440                 445 aca aaa agg tcc aac gag ctg aat ctc agc ggt aat agt ggt gct tta     1392
Thr Lys Arg Ser Asn Glu Leu Asn Leu Ser Gly Asn Ser Gly Ala Leu
450                 455                 460 gcc ctg cag tgg tcc agt ggg gag caa aga aga ggc ggc ctt gaa gct     1440
Ala Leu Gln Trp Ser Ser Gly Glu Gln Arg Arg Gly Gly Leu Glu Ala
465                 470                 475                 480 gga tct cct gcc atc aat ctc atg ggt gta aaa gtg gga gag atg tgt     1488
Gly Ser Pro Ala Ile Asn Leu Met Gly Val Lys Val Gly Glu Met Cys
            485                 490                 495 gag gcc cag gaa tgg att gaa agg ttg ctg gtc tcc ctg gac cac cac     1536
Glu Ala Gln Glu Trp Ile Glu Arg Leu Leu Val Ser Leu Asp His His
        500                 505                 510 atc att gag aat aat cat att ctc tat ctt ggg aaa aaa gag cac gac     1584
Ile Ile Glu Asn Asn His Ile Leu Tyr Leu Gly Lys Lys Glu His Asp
    515                 520                 525 gtg ctg tct gag ctc cag acc agc aca aga gtc tcc att tca gag act     1632
Val Leu Ser Glu Leu Gln Thr Ser Thr Arg Val Ser Ile Ser Glu Thr
530                 535                 540 gtc agt cca aga acg gcc act ttg gag att aaa ggt ccc cag gct gac     1680
Val Ser Pro Arg Thr Ala Thr Leu Glu Ile Lys Gly Pro Gln Ala Asp
```

```
                545                 550                 555                 560
ctc att gac gca gtt atg agg att gaa tgt atg ctg tgt gac gtt cag        1728
Leu Ile Asp Ala Val Met Arg Ile Glu Cys Met Leu Cys Asp Val Gln
                    565                 570                 575 gaa gaa gtg gca gga aaa agg gag aaa aat ctt tgg agc ttg tca gga        1776
Glu Glu Val Ala Gly Lys Arg Glu Lys Asn Leu Trp Ser Leu Ser Gly
            580                 585                 590 cag ggg acc aac cag caa gaa aaa ctg gat aaa atg gaa gaa tcg tac        1824
Gln Gly Thr Asn Gln Gln Glu Lys Leu Asp Lys Met Glu Glu Ser Tyr
        595                 600                 605 aca ttt caa cga tac cca gca tca tta act cag gaa ctt cag gac cga        1872
Thr Phe Gln Arg Tyr Pro Ala Ser Leu Thr Gln Glu Leu Gln Asp Arg
    610                 615                 620 aag aaa cag ttt gaa aag tgt ggc ttg tgg gtt gtg cag gtg gag cag        1920
Lys Lys Gln Phe Glu Lys Cys Gly Leu Trp Val Val Gln Val Glu Gln
625                 630                 635                 640 ata gac aat aag gtg ctg ctg gct gcc ttc caa gag aag aag aaa atg        1968
Ile Asp Asn Lys Val Leu Leu Ala Ala Phe Gln Glu Lys Lys Lys Met
                645                 650                 655 atg gaa gag agg acg cca aag gga tct ggg agc caa agg ttg ttt cag        2016
Met Glu Glu Arg Thr Pro Lys Gly Ser Gly Ser Gln Arg Leu Phe Gln
            660                 665                 670 cag gtc cca cat cag ttc tgc aat acg gtg tgc aga gtc ggc ttc cac        2064
Gln Val Pro His Gln Phe Cys Asn Thr Val Cys Arg Val Gly Phe His
        675                 680                 685 aga atg tat tcg aca tcc tat aac cca gtt tat gga gcc ggc ata tat        2112
Arg Met Tyr Ser Thr Ser Tyr Asn Pro Val Tyr Gly Ala Gly Ile Tyr
    690                 695                 700 ttc acc aag agc ctc aaa aat cta gca gac aag gtc aag aaa acc tca        2160
Phe Thr Lys Ser Leu Lys Asn Leu Ala Asp Lys Val Lys Lys Thr Ser
705                 710                 715                 720 agc aca gac aag cta atc tat gtg ttt gag gca gaa gta ctc aca ggg        2208
Ser Thr Asp Lys Leu Ile Tyr Val Phe Glu Ala Glu Val Leu Thr Gly
                725                 730                 735 tcc ttc tgt cag ggt aat tcc tca aat atc atc cct cca cca ttg agt        2256
Ser Phe Cys Gln Gly Asn Ser Ser Asn Ile Ile Pro Pro Pro Leu Ser
            740                 745                 750 cct ggg gcc tta gat gtc aat gac agc gta gtt gac aat gtt tcc agc        2304
Pro Gly Ala Leu Asp Val Asn Asp Ser Val Val Asp Asn Val Ser Ser
        755                 760                 765 cct gaa acc att gtt gtt ttt aat ggc atg cag gcc atg ccc ctg tac        2352
Pro Glu Thr Ile Val Val Phe Asn Gly Met Gln Ala Met Pro Leu Tyr
    770                 775                 780 ttg tgg act tgc aca cag gat agg aca ttc tca cag cat ccg atg tgg        2400
Leu Trp Thr Cys Thr Gln Asp Arg Thr Phe Ser Gln His Pro Met Trp
785                 790                 795                 800 tca cag gac tac tca tca gga cca gga atg gtc tct tcg ctg cag tcc        2448
Ser Gln Asp Tyr Ser Ser Gly Pro Gly Met Val Ser Ser Leu Gln Ser
                805                 810                 815 tgg gaa tgg gtc tta aat ggc agc tct gtt                                2478
Trp Glu Trp Val Leu Asn Gly Ser Ser Val
            820                 825
```